(12) United States Patent
Carson et al.

(10) Patent No.: US 7,531,710 B2
(45) Date of Patent: May 12, 2009

(54) MEDIATED ELECTROCHEMICAL OXIDATION OF INORGANIC MATERIALS

(75) Inventors: Roger W. Carson, Vienna, VA (US); Bruce W. Bremer, Franklin, MA (US)

(73) Assignee: Scimist, Inc., Springfield, VA (US)

( * ) Notice: Subject to any disclaimer, the term of this patent is extended or adjusted under 35 U.S.C. 154(b) by 789 days.

(21) Appl. No.: 10/527,103

(22) PCT Filed: Sep. 10, 2003

(86) PCT No.: PCT/US03/28200
§ 371 (c)(1), (2), (4) Date: Apr. 11, 2005

(87) PCT Pub. No.: WO2004/024634
PCT Pub. Date: Mar. 25, 2004

(65) Prior Publication Data
US 2005/0245784 A1 Nov. 3, 2005

Related U.S. Application Data

(60) Provisional application No. 60/409,202, filed on Sep. 10, 2002.

(51) Int. Cl.
A62D 3/00 (2007.01)
(52) U.S. Cl. ...................... 588/410; 588/900
(58) Field of Classification Search .............. 588/303, 588/320, 405, 410, 900
See application file for complete search history.

(56) References Cited

U.S. PATENT DOCUMENTS

| | | |
|---|---|---|
| 4,013,552 A | 3/1977 | Kreuter |
| 4,069,371 A | 1/1978 | Zito |
| 4,749,519 A | 6/1988 | Koehly et al. |
| 4,752,364 A | 6/1988 | Dhooge |
| 4,874,485 A | 10/1989 | Steele |
| 4,925,643 A | 5/1990 | Steele |
| 4,967,673 A | 11/1990 | Gunn |
| 5,047,224 A | 9/1991 | Dhooge |
| 5,261,336 A | 11/1993 | Williams |
| 5,380,445 A | 1/1995 | Rivard et al. |
| 5,516,972 A | 5/1996 | Farmer |
| 5,707,508 A | 1/1998 | Surma et al. |
| 5,756,874 A | 5/1998 | Steward |
| 5,810,995 A | 9/1998 | Soilleux et al. |
| 5,855,763 A | 1/1999 | Conlin et al. |
| 5,911,868 A | 6/1999 | Balazs et al. |
| 5,919,350 A | 7/1999 | Balazs et al. |
| 5,952,542 A | 9/1999 | Steele |
| 5,968,337 A | 10/1999 | Surma |
| 6,402,932 B1 | 6/2002 | Bremer et al. |

FOREIGN PATENT DOCUMENTS

| | | |
|---|---|---|
| DE | 4113817 | 11/1991 |
| DE | 4205739 | 8/1993 |
| WO | WO97/15356 | 1/1997 |

OTHER PUBLICATIONS

Davidson, L. et al.; *Ruthenium-Mediated Electrochemical Destruction of Organic Wastes*; Platinum Metal Reviews; 1998; vol. 42, No. 3; pp. 90-98 (Ruthenium).
Morrison, R. & Boyd, R. (Editors); *Organic Chemistry*; New York University; Allen & Bacon, Inc.; 1973; (Third Edition); Chapter 1—Structure & Properties; pp. 1-2 (Organic).
Pletcher, D. & Walsh, F.; *Industrial Electrochemistry*; 1990; Chapman & Hall; Chapters 1 & 2; pp. 1-172.
Surma et al.; *Catalyzed Electrochemical Oxidation (CEO) of Rocky Flats Contaminated Combustible Materials*; Mar. 1996; Report prepared for U.S. Department of Energy, Pacific Northwest National Laboratory, Richland, WA; 25 pages.
Steward Tony; *Electrochemical Oxidation of Hazardous Organics*; Sep. 20, 1996; EO Systems, Inc.; 2 pages.
Whaley, S.; *UNR Attacks Hazardous Waste Riddle*; Las Vegas Review-Journal Oct. 21, 1997; 3 pages.
Lewis, R.; *Hawley's Condensed Chemical Dictionary*; Twelfth Edition; 1993; Van Nostrand—Reinhold; 4 pages.
Anonymous; *Chemical Storage Tank Systems—Good Practice Guide (Summary Guidance Document)*; CIRIA Publication WO02; Classic House, 174-180 Old Street, London, EC1V-9BP, England. 43 pages.
Chiba et al.; *Mediated Electrochemical Oxidation as an Alternative to Incineration for Mixed Wastes*; Lawrence Livermore National Laboratory Paper (UCRL-JC-119133) prepared for WM95 Synposia, Tucson, AZ, Mar. 1, 1995 (dated Feb. 1995) (12 pages).

*Primary Examiner*—Edward M Johnson
(74) *Attorney, Agent, or Firm*—James Creighton Wray

(57) ABSTRACT

A mediated electrochemical oxidation process and apparatus for the use of mediated electrochemical oxidation for the oxidation, conversion/recovery, and decontamination of inorganic solids, liquids, and gases where higher oxidation states exist. Inorganic materials are introduced into an apparatus for contacting the inorganic materials with an electrolyte containing the oxidized form of one or more reversible redox couples, at least one of which is produced electrochemically by anodic oxidation at the anode of an electrochemical cell. The oxidized forms of any other redox couples present are produced either by similar anodic oxidation or reaction with the oxidized form of other redox couples present and capable of affecting the required redox reaction. The oxidized species of the redox couples oxidize the inorganic waste molecules and are converted to their reduced form, whereupon they are reoxidized by either of the aforementioned mechanisms and the redox cycle continues.

26 Claims, 7 Drawing Sheets

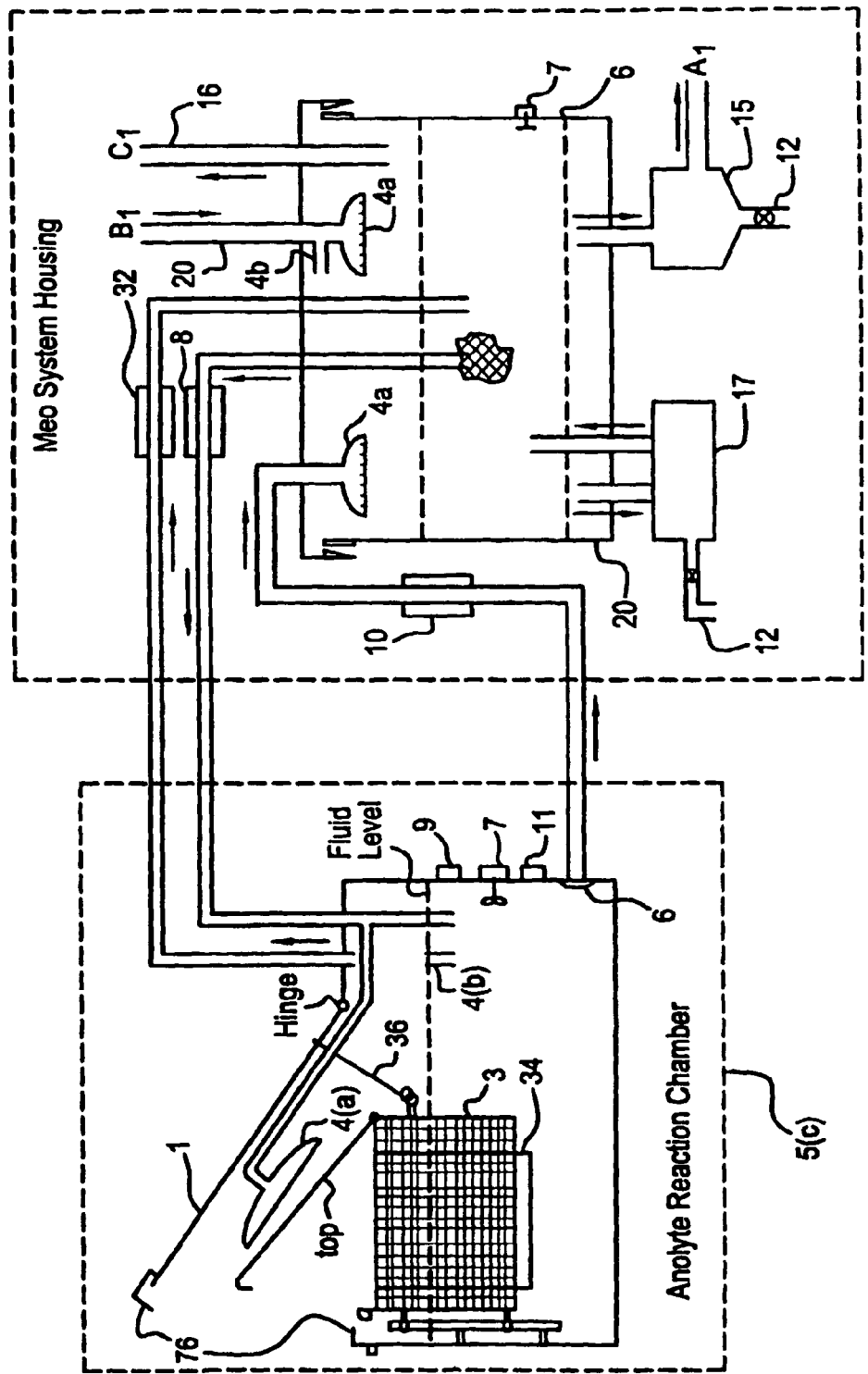

ents for the use of mediated electrochemical oxidation (MEO) for
MEDIATED ELECTROCHEMICAL OXIDATION OF INORGANIC MATERIALS This application claims the benefit of U.S. Provisional Application No. 60/409,202, filed Sep. 10, 2002 and PCT/US03/28200, filed Sep. 10, 2003, which are hereby incorporated by reference in its entirety.

FIELD OF THE INVENTION

This invention relates generally to a process and apparatus for the use of mediated electrochemical oxidation (MEO) for the oxidation, conversion/recovery, and decontamination (such as cleaning equipment and containers, etc.) of all previously defined inorganic solid, liquid, or gas where higher oxidation states exist which includes, but is not limited to, halogenated inorganic compounds (except fluorinated), inorganic pesticides and herbicides, inorganic fertilizers, carbon residues, incinerator residue, inorganic carbon compounds, mineral formations, mining tailings, inorganic salts, metals and metal compounds, etc.; and combined waste (e.g. a mixture of any of the foregoing with each other or other non-inorganic materials) henceforth collectively referred to as inorganic waste.

BACKGROUND OF THE INVENTION

Inorganic waste is a growing problem for today's technological society. The inorganic waste generated by a large segment of our industrial sector is an increasing burden on these companies as well as the whole country in general. Considerable researches in the fields of public health safety and environmental protection have raised the level of concern relative to the impact of these inorganic materials on our society. This has lead to the definition of this waste being expanded in its coverage of materials that must be handled in a controlled manner. The National Institute for Occupational Safety and Health (NIOSH) is responsible for undertaking research and developing recommended health and safety standards. They are joined together with Occupational Safety and Health Administration (OSHA) whose jurisdiction includes promulgation and enforcement activities. NIOSH publishes a *Pocket Guide to Chemical Hazards* which list several hundred substances requiring special handling. An examination of the list shows that approximately 40% of the substances on the list are inorganic vice organic.

Mining processes have produced considerable waste that is stored at the mining sites. The chemical processes that are used to extract minerals from the mining ore have contaminated these sites. Typical of these contaminations are the cyanide used in gold and silver recovery processes. The cyanide contaminates the mining waste and can leach out of the waste and get into water tables expanding the contaminated areas.

The cost of disposing of inorganic waste in the U.S. is a multi-billion dollar per year industry. The capital cost of the equipment required is in the hundreds of millions of dollars. All businesses, industrial companies, and institutions that generate and handle this category of waste must provide safe effective and inexpensive disposal of the waste. In recent years there has been increasing concern over the disposal of inorganic waste. The number of materials that need to be controlled has continued to increase. Furthermore, the handling, transporting, and management of the disposal process have continued to increase in cost. The liability for the consequences of the disposal of these materials is a major concern for those involved in the use of these materials. The liability of the users does not end with the transfer of control of these materials to disposal companies for future problems they may cause.

The concern over the control and safety standards for the chemical industry has lead to a whole family of regulatory Federal Acts. The following list of Federal Acts reflects the broad nature of the problem of inorganic waste:

TSCA (Toxic Substances and Control Act) regulates industrial chemicals.

FIFRA (Federal Insecticide, Fungicide, and Rodenticide Act) requires EPA registration for all pesticides sold in the U.S.

FFDCA (Federal Food, Drug, and Cosmetic Act) regulates the establishment of pesticide tolerances.

EPCRA (Emergence Planning and Community Right-to-Know Act) requires local emergence planning for responses to industrial chemical or pesticide accidents and mandates a national inventory of toxic chemical releases.

CAA (Clean Air Act) establishes criteria and standards for regulating toxic air pollutants.

CWA (Clean Water Act) establishes criteria and standards for pollutants in surface water bodies.

SDWA (Safe Drinking Water Act) establishes enforceable Maximum Contaminant Levels (MCLs) for pesticides and Health Advisories.

RCRA (Resources Conservation and Recovery Act) requires appropriate handling and disposal of hazardous waste.

CERCLA (Comprehensive Environmental Response, Compensation and Liability Act) covers incidents with hazardous materials and mandates the EPA Superfund program to clean up the highest priority sites contaminated by chemicals.

HMTA (Hazardous Materials Transportation Act) ensures the safe and environmentally sound transportation of hazardous materials by all modes of transportation.

FHSA (Federal Hazardous Substances Act), CPSA (Consumer Product Safety Act), and PPPA (Poison Prevention Packaging Act) regulates the safety of consumer products including chemical safety.

OSHA (Occupational Safety and Health Act) regulates toxic chemicals related to occupational safety.

NIOSH (National Institute for Occupational Safety and Health) prepares the *NIOSH Pocket Guide to Chemical Hazards* as a result of their responsibility for undertaking research and developing recommended health and safety standards.

The dominant methodologies used today generally can be categorized as thermal decomposition, long-term storage, or landfills methods.

The most frequently used thermal destruction techniques are various forms of incineration. All of these techniques have the potential to produce volatile compounds that have serious health and environmental consequences. The MEO process used in this patent does not create these conditions.

In the case of long-term storage, this method is viewed as delaying the solving of the problem and in fact actually increases the degree of the problem in the future. The current position argued by EPA is to move in the direction of avoiding the use of the problem waste by using alternatives solutions in lieu of containment. The dumping in landfills has considerable risk for the users of these materials. Therefore, the user community has an immediate need to develop and incorporate improved methods for the handling of all types and form of inorganic wastes. The methodology of this patent provides for the potential use of inorganic compounds and their immediate oxidation using mediated electrochemical oxidation (MEO) thus avoiding waste-handling problems associated with transportation, offsite destruction, or long-term storage.

SUMMARY OF THE INVENTION

This invention relates generally to a process and apparatus for the use of mediated electrochemical oxidation (MEO) for the oxidation, conversion/recovery, and decontamination (such as cleaning equipment and containers, etc.) of all previously defined inorganic solid, liquid, or gas where higher oxidation states exist which includes, but is not limited to, halogenated inorganic compounds (except fluorinated), inorganic pesticides and herbicides, inorganic fertilizers, carbon residues, incinerator ash, inorganic carbon compounds, mineral formations, mining tailings, inorganic salts, metals and metal compounds, etc.); and combined waste (e.g. a mixture of any of the foregoing with each other or other non-inorganic materials) henceforth collectively referred to as inorganic waste. The method and apparatus in this patent has the flexibility to deal with all of the forms of the inorganic waste as identified.

The MEO methodology in this patent converts the inorganic compounds into benign components. The MEO process oxidizes the inorganic compounds to their higher oxidation states. Inorganic compounds in their higher oxidation states are not candidates for this patent process (i.e., silicon dioxide $SiO_2$). Using this MEO methodology and process all previously defined inorganic solid or liquid wastes are decomposed into aqueous solution and in some cases into carbon dioxide, water, and trace amounts of inorganic salts. The process may be operated in three different modes (oxidation, conversion/recovery, and decontamination).

In the first mode (oxidation) the process runs until the inorganic materials are totally decomposed into these benign components as previously mentioned. In the second mode (conversion/recovery) the process is operated such that the inorganic materials are reduced to an intermediate stage or chemical intermediate. In the conversion mode, the chemical intermediates that result are not toxic or hazardous material and may be disposed off in a safe and healthy waste disposal system (e.g., the decomposition of the cyanide in the mining tailing reducing the toxicity of the mining waste). In the recovery mode, the process is operated until an inorganic material is produced that can be used thus turning inorganic waste material into a recovered product. An example of this process would be the recovery of the residual gold in the mining process where the cyanide process only removed 40 to 60 percent of the gold in the mine ore. A second example is the recovery of precious metals from a plating sludge in the bottom of tanks while decomposing the hazardous materials present in the sludge.

The third mode (decontamination) involves contaminated equipment, instruments, glassware, containers (e.g., 50 gallon drums) and materials. In this mode the MEO process oxidizes the inorganic waste that has contaminated them. These items are placed in an anolyte reaction chamber (see FIGS. 1C, 1D, and 1E) and the anolyte containing the oxidizing species is introduced into the chamber. The MEO process cleans the contaminated items rendering them non-toxic and safe to reuse or to dispose off.

The general mediated electrochemical oxidation (MEO) process in this patent involves an anolyte containing one or more redox couples, wherein the oxidized form of at least one redox couple is produced by anodic oxidation at the anode of an electrochemical cell. The oxidized forms of any other redox couples present are produced either by similar anodic oxidation or by reaction with the oxidized form of other redox couples present capable of affecting the required redox reaction. The anodic oxidation in the electrochemical cell is driven by an externally induced electrical potential induced between the anode(s) and cathode(s) of the cell. The oxidized species of the redox couples oxidize the inorganic waste molecules and are themselves converted to their reduced form, whereupon they are reoxidized by either of the aforementioned mechanisms and the redox cycle continues until all oxidizable waste species, including intermediate reaction products, have undergone the desired degree of oxidation. The redox species ions are thus seen to "mediate" the transfer of electrons from the waste molecules to the anode, (i.e., oxidation of the waste).

A membrane in the electrochemical cell separates the anolyte and catholyte, thereby preventing parasitic reduction of the oxidizing species at the cathode. The membrane is ion-selective or semi-permeable (i.e., microporous plastic, ceramic, sintered glass frit, etc.). The preferred MEO process uses the mediator species described in Table I (simple anions redox couple mediators); the Type I isopolyanions (IPA) formed by Mo, W, V, Nb, and Ta, and mixtures thereof; the Type I heteropolyanions (HPA) formed by incorporation into the aforementioned isopolyanions of any of the elements listed in Table II (heteroatoms) either singly or in combinations thereof; any type of heteropolyanion containing at least one heteropolyatom (i.e. element) contained in both Table I and Table II; or combinations of mediator species from any or all of these generic groups.

Simple Anion Redox Couple Mediators

Table I shows the simple anion redox couple mediators used in the preferred MEO process wherein "species" defines the specific ions for each chemical element that have applicability to the MEO process as either the reduced (e.g., $Fe^{+3}$) or oxidizer (e.g., $FeO_4^{-2}$) form of the mediator characteristic element (e.g., Fe), and the "specific redox couple" defines the specific associations of the reduced and oxidized forms of these species (e.g., $Fe^{+3}/FeO_4^{-2}$) that are claimed for the MEO process. Species soluble in the anolyte are shown in Table I in normal print while those that are insoluble are shown in bold underlined print. The characteristics of the MEO Process claimed in this patent are specified in the following paragraphs.

The anolyte contains one or more redox couples which in their oxidized form consist of either single multivalent element anions (e.g., $Ag^{+2}$, $Ce^{+4}$, $Co^{+3}$, $Pb^{+4}$, etc.), insoluble oxides of multivalent elements (e.g., $PbO_2$, $CeO_2$, $PrO_2$, etc.), or simple oxoanions (also called oxyanions) of multivalent elements (e.g., $FeO_4^{-2}$, $NiO_4^{-2}$, $BiO_3^-$, etc.). The redox couples in their oxidized form are called the mediator species. The nonoxygen multivalent element component of the mediator is called the characteristic element of the mediator species. We have chosen to group the simple oxoanions with the simple anion redox couple mediators rather than with the complex (i.e., polyoxometallate (POM)) anion redox couple mediators discussed in the next section and refer to them collectively as simple anion redox couple mediators.

In one embodiment of this process both the oxidized and reduced forms of the redox couple are soluble in the anolyte. The reduced form of the couple is anodically oxidized to the oxidized form at the cell anode(s) whereupon it oxidizes molecules of inorganics either dissolved in or located on waste particle surfaces wetted by the anolyte, with the concomitant reduction of the oxidizing agent to its reduced form, whereupon the MEO process begins again with the reoxidation of this species at the cell anode(s). If other less powerful redox couples of this type (i.e., reduced and oxidized forms soluble in anolyte) are present, they too may undergo direct anodic oxidation or the anodically oxidized more powerful oxidizing agent may oxidize them rather than a waste molecule. The weaker redox couple(s) is selected such that their oxidation potential is sufficient to affect the desired reaction with the waste molecules. The oxidized species of all the redox couples oxidize the inorganic waste molecules and are themselves converted to their reduced form, whereupon they are reoxidized by either of the aforementioned mechanisms and the redox cycle continues until all oxidizable waste species, including intermediate reaction products, have undergone the desired degree of oxidation.

The preferred mode for the MEO process as described in the preceding section is for the redox couple species to be soluble in the anolyte in both the oxidized and reduced forms, however this is not the only mode of operation claimed herein. If the reduced form of the redox couple is soluble in the anolyte (e.g., $Pb^{+2}$) but the oxidized form is not (e.g., $PbO_2$), the following processes are operative. The insoluble oxidizing agent is produced either as a surface layer on the anode by anodic oxidation, or throughout the bulk of the anolyte by reacting with the oxidized form of other redox couples present capable of affecting the required redox reaction, at least one of which is formed by anodic oxidation. The oxidizable waste is either soluble in the anolyte or dispersed therein at a fine particle size, (e.g., emulsion, colloid, etc.) thereby affecting intimate contact with the surface of the insoluble oxidizing agent (e.g., $PbO_2$) particles. Upon reaction of the waste with the oxidizing agent particles, the waste is oxidized and the insoluble oxidizing agent molecules on the anolyte wetted surfaces of the oxidizing agent particles reacting with the waste are reduced to their soluble form and are returned to the bulk anolyte, available for continuing the MEO process by being reoxidized.

In another variant of the MEO process, if the reduced form of the redox couple is insoluble in the anolyte (e.g., $TiO_2$) but the oxidized form is soluble (e.g., $TiO_2^{+2}$), the following processes are operative. The soluble (i.e., oxidized) form of the redox couple is produced by the reaction of the insoluble (i.e., reduced form) redox couple molecules on the anolyte wetted surfaces of the oxidizing agent particles with the soluble oxidized form of other redox couples present capable of affecting the required redox reaction, at least one of which is formed by anodic oxidation and soluble in the anolyte in both the reduced and oxidized forms. The soluble oxidized species so formed are released into the anolyte whereupon they oxidize waste molecules in the manner previously described and are themselves converted to the insoluble form of the redox couple, thereupon returning to the starting point of the redox MEO cycle.

In this invention, when an alkaline anolyte is used, the $CO_2$ resulting from oxidation of the inorganic waste (that contains carbon) reacts with the anolyte to form alkali metal bicarbonates/carbonates. The bicarbonate/carbonate ions circulate within the anolyte where they are reversibly oxidized to percarbonate ions either by anodic oxidation within the electrochemical cell or alternately by reacting with the oxidized form of a more powerful redox couple mediator, when present in the anolyte. The carbonate thus functions exactly as a simple anion redox couple mediator, thereby producing an oxidizing species from the waste oxidation products that it is capable of oxidizing additional inorganic waste.

In this invention, when the inorganic waste contains elements that are identified in Table I they become possible mediated redox couples. The initial anion mediated redox couple(s) contained in the MEO anolyte solution begins the oxidation of the inorganic waste. As the inorganic waste decomposes the potential exists for new mediated species to be released into the anolyte. The new mediator species circulates in the anolyte and passes into the electrochemical cell. The mediator species is converted to the oxidized form of the redox couple by anodic oxidation at the anode of the electrochemical cell. The mediated redox couple oxidizer initially present in the MEO anolyte is raised to the oxidizer form in the mediated redox couple derived from the inorganic waste. The derived mediated redox couple functions exactly as the simple anion redox couple and is capable of oxidizing additional inorganic waste.

The electrolytes used in this patent are from a family of acids, alkali, and neutral salt aqueous solutions (e.g. sulfuric acid, potassium hydroxide, sodium sulfate aqueous solutions, etc.).

A given redox couple or mixture of redox couples (i.e. mediator species) are to be used with different electrolytes.

The electrolyte composition is selected based on demonstrated adequate solubility of the compound containing at least one of the mediator species present in the reduced form (e.g., sulfuric acid may be used with ferric sulfate, etc.).

The concentration of the mediator species containing compounds in the anolyte may range from 0.0005 molar (M) up to the saturation point.

The concentration of electrolyte in the anolyte is governed by its effect upon the solubility of the mediator species containing compounds and by the conductivity of the anolyte solution desired in the electrochemical cell for the given mediator species being used.

The temperature over which the electrochemical cell may be operated ranges from approximately 0° C. to slightly below the boiling point of the electrolytic solution.

The MEO process is operated at ambient atmospheric pressure.

The mediator species are differentiated on the basis of whether they are capable of reacting with the electrolyte to produce free radicals (e.g., $.O_2H$ (perhydroxyl), $.OH$ (hydroxyl), $.SO_4$ (sulfate), $.NO_3$ (nitrate), etc.). Such mediator species are classified herein as "super oxidizers" (SO) and typically exhibit oxidation potentials at least equal to that of the $Ce^{+3}/Ce^{+4}$ redox couple (i.e., 1.7 volts at 1 molar, 25° C. and pH 1).

The electrical potential between the electrodes in the electrochemical cell is based upon the oxidation potential of the most reactive redox couple present in the anolyte and serving as a mediator species, and the ohmic losses within the cell. In the case of certain electrolyte compositions a low level AC voltage is impressed upon the DC voltage to retard the formation of cell performance limiting surface films on the electrode. Within the current density range of interest the electrical potential may be approximately 0.1 to 10.0 volts DC.

Complex Anion Redox Couple Mediators

The preferred characteristic of the oxidizing species in the MEO process is that it be soluble in the aqueous anolyte in both the oxidized and reduced states. The majorities of metal oxides and oxoanion (oxyanion) salts are insoluble, or have poorly defined or limited solution chemistry. The early transition elements, however, are capable of spontaneously forming a class of discrete polymeric structures called polyoxometallate (POMs) which are highly soluble in aqueous solutions over a wide pH range. The polymerization of simple tetrahedral oxoanions of interest herein involves an expansion of the metal, M, coordination number to 6, and the edge and corner linkage of $MO_6$ octahedra. Chromium is limited to a coordination number of 4, restricting the POMs based on $CrO_4$ tetrahedra to the dichromate ion $[Cr_2O_7]^{-2}$ which is included in Table I. Based upon their chemical composition POMs are divided into the two subclasses isopolyanions (IPAs) and heteropolyanions (HPAs), as shown by the following general formulas:

Isopolyanions (IPAs)-$[M_mO_y]^{p-}$ and,

Heteropolyanions (HPAs)-$[X_xM_mO_y]^{q-}$ (m>x)

where the addenda atom, M, is usually Molybdenum (Mo) or Tungsten (W), and less frequently Vanadium (V), Niobium (Nb), or Tantalum (Ta), or mixtures of these elements in their highest ($d^0$) oxidation state. The elements that can function as addenda atoms in IPAs and HPAs appear to be limited to those with both a favorable combination of ionic radius and charge, and the ability to form dn-pn M-O bonds. However, the heteroatoms, X, have no such limitations and can be any of the elements listed in Table II.

There is a vast chemistry of POMs that involves the oxidation/reduction of the addenda atoms and those heteroatoms listed in Table II that exhibit multiple oxidation states. The partial reduction of the addenda, M, atoms in some POMs strictures (i.e., both IPAs and HPAs) produces intensely colored species, generically referred to as "heteropoly blues". Based on structural differences, POMs can be divided into two groups, Type I and Type II. Type I POMs consist of $MO_6$ octahedra each having one terminal oxo oxygen atom while Type II have 2 terminal oxo oxygen atoms. Type II POMs can only accommodate addenda atoms with $d^0$ electronic configurations, whereas Type I, e.g., Keggin ($XM_{12}O_{40}$), Dawson ($X_2M_{18}O_{62}$), hexametalate ($M_6O_{19}$), decatungstate ($W_{10}O_{32}$), etc., can accommodate addenda atoms with $d^0$, $d^1$, and $d^2$ electronic configurations. Therefore, while Type I structures can easily undergo reversible redox reactions, structural limitations preclude this ability in Type II structures. Oxidizing species applicable for the MEO process are therefore Type I POMs (i.e., IPAs and HPAs) where the addenda, M, atoms are W, Mo, V, Nb, Ta, or combinations thereof.

The high negative charges of polyanions often stabilize heteroatoms in unusually high oxidation states, thereby creating a second category of MEO oxidizers in addition to the aforementioned Type I POMs. Any Type I or Type II HPA containing any of the heteroatom elements, X, listed in Table II, that also are listed in Table I as simple anion redox couple mediators, can also function as an oxidizing species in the MEO process.

The anolyte contains one or more complex anion redox couples, each consisting of either the aforementioned Type I POMs containing W, Mo, V, Nb, Ta or combinations thereof as the addenda atoms, or HPAs having as heteroatoms (X) any elements contained in both Tables I and II, and which are soluble in the electrolyte (e.g. sulfuric acid, etc.).

The electrolytes used in this claim are from a family of acids, alkali, and neutral salt aqueous solutions (e.g. sulfuric acid, potassium hydroxide, sodium sulfate aqueous solutions, etc.).

A given POM redox couple or mixture of POM redox couples (i.e., mediator species) may be used with different electrolytes.

The electrolyte composition is selected based on demonstrating adequate solubility of at least one of the compounds containing the POM mediator species in the reduced form and being part of a redox couple of sufficient oxidation potential to affect oxidation of the other mediator species present.

The concentration of the POM mediator species containing compounds in the anolyte may range from 0.0005M (molar) up to the saturation point. The concentration of electrolyte in the anolyte may be governed by its effect upon the solubility of the POM mediator species containing compounds and by the conductivity of the anolyte solution desired in the electrochemical cell for the given POM mediator species being used to allow the desired cell current at the desired cell voltage.

The temperature over which the electrochemical cell may be operated ranges from approximately 0° C. to just below the boiling point of the electrolytic solution. The most frequently used thermal techniques, such as incineration, exceed this temperature range. All of these techniques have the potential to produce volatile compounds that have serious health and environmental consequences.

The MEO process is operated at ambient atmospheric pressure.

The POM mediator species are differentiated on the basis of whether they are capable of reacting with the electrolyte to produce free radicals (e.g., $.O_2H$, $.OH$, $.SO_4$, $.NO_3$). Such mediator species are classified herein as "super oxidizers" (SO) and typically exhibit oxidation potentials at least equal to that of the $Ce^{+3}/Ce^{+4}$ redox couple (i.e., 1.7 volts at 1 molar, 25° C. and pH 1).

The electrical potential between the anode(s) and cathode(s) in the electrochemical cell is based on the oxidation potential of the most reactive POM redox couples present in the anolyte and serving as a mediator species, and the ohmic losses within the cell. Within the current density range of interest the electrical potential may be approximately 0.1 to 10.0 volts DC.

In the case of certain electrolyte compositions, a low level AC voltage is impressed across the electrodes in the electrochemical cell. The AC voltage is used to retard the formation of surface films on the electrodes that would have a performance limiting effect.

Mixed Simple and Complex Anion Redox Couple Mediators

The preferred MEO process for a combination of simple anion redox couple mediators (A) and complex anion redox couple mediators (B) may be mixed together to form the system anolyte. The characteristics of the resulting MEO process is similar to the previous discussions.

The use of multiple oxidizer species in the MEO process has the following potential advantages:
a) The overall waste oxidation rate is increased if the reaction kinetics of anodically oxidizing mediator "A", oxidizing mediator "B" and oxidized mediator "B" oxidizing the inorganic waste is sufficiently rapid such that the combined speed of the three step reaction train is faster than the two step reaction trains of anodically oxidizing mediator "A" or "B", and the oxidized mediators "A" or "B" oxidizing the waste.
b) If the cost of mediator "B" is sufficiently less than that of mediator "A", the used of the above three step reaction train results in lowering the cost of waste oxidation due to the reduced cost associated with the smaller required inventory and process losses of the more expensive mediator "A". An example of this is the use of a silver (II)-peroxysulfate mediator system to reduce the cost associated with a silver (I/II) only MEO process and overcome the slow anodic oxidation kinetics of a sulfate/ peroxysulfate only MEO process.

c) The MEO process is "desensitized" to changes in the types of molecular bonds present in the inorganic waste as the use of multiple mediators, each selectively attacking different types of chemical bonds, results in a highly "nonselective" oxidizing system.

Anolyte Additional Features

In one preferred embodiment of the MEO process in this invention, there are one or more simple anion redox couple mediators in the anolyte aqueous solution. In a preferred embodiment of the MEO process, there are one or more complex anion (i.e., POMs) redox couple mediators in the anolyte aqueous solution. In another preferred embodiment of the MEO process, there are one or more simple anion redox couples and one or more complex anion redox couples in the anolyte aqueous solution.

The MEO process of the present invention uses any oxidizer species listed in Table I that are found in situ in the waste to be oxidized; For example, when the inorganic waste also contains lead compounds that become a source of $Pb^{+2}$ ions under the MEO process conditions within the anolyte, the waste-anolyte mixture may be circulated through an electrochemical cell. The oxidized form of the reversible lead redox couple may be formed either by anodic oxidation within the electrochemical cell or alternately by reacting with the oxidized form of a more powerful redox couple, if present in the anolyte and the latter being anodically oxidized in the electrochemical cell. The lead thus functions exactly as a simple anion redox couple species thereby oxidizing the inorganic waste component leaving only the lead to be disposed of. Adding one or more of any of the anion redox couple mediators described in this patent further enhances the MEO process described above.

In the MEO process of the invention, anion redox couple mediators in the anolyte part of an aqueous electrolyte solution uses an acid, neutral or alkaline solution depending on the temperature and solubility of the specific mediator(s). The anion oxidizers used in the basic MEO process preferably attack specific inorganic molecules. Hydroxyl free radicals preferentially attack inorganic molecules.

Some redox couples having an oxidation potential at least equal to that of the $Ce^{+3}/Ce^{+4}$ redox couple (i.e., 1.7 volts at 1 molar, 25° C. and pH 1), and sometimes requiring heating to above about 50° C. (i.e., but less than the boiling point of the electrolyte) can initiate a second oxidation process wherein the mediator ions in their oxidized form interact with the aqueous anolyte, creating secondary oxidizer free radicals (e.g., $.O_2H$, $.OH$, $.SO_4$, $.NO_3$, etc.) or hydrogen peroxide. Such mediator species in this invention are classified herein as "super oxidizers" (SO) to distinguish them from the "basic oxidizers" incapable of initiating this second oxidation process.

The oxidizer species addressed in this patent are described in Table I (simple anions redox couple mediators): Type I IPAs formed by Mo, W, V, Nb, Ta, or mixtures thereof as addenda atoms; Type I HPAs formed by incorporation into the aforementioned IPAs of any of the elements listed in Table II (heteroatoms) either singly or in combinations thereof; or any HPA containing at least one heteroatom type (i.e., element) contained in both Table I and Table II; or mediator species from any or all of these generic groups.

Each oxidizer anion element has normal valence states (NVS) (i.e., reduced form of redox couple) and higher valence states (HVS) (i.e., oxidized form of redox couple) created by stripping electrons off NVS species when they pass through an electrochemical cell. The MEO process of the present invention uses a broad spectrum of anion oxidizers; these anion oxidizers used in the basic MEO process may be interchanged in the preferred embodiment without changing the equipment.

In preferred embodiments of the MEO process, the basic MEO process is modified by the introduction of additives such as tellurate or periodate ions which serve to overcome the short lifetime of the oxidized form of some redox couples (e.g., $Cu^{+3}$) in the anolyte via the formation of more stable complexes (e.g., $[Cu\,(IO_6)_2]^{-7}$, $[Cu(HTeO_6)_2]^{-7}$). The tellurate and periodate ions can also participate directly in the MEO process as they are the oxidized forms of simple anion redox couple mediators (see Table I) and participate in the oxidation of inorganic waste in the same manner as previously described for this class of oxidizing agents.

Alkaline Electrolytes

In one preferred embodiment, a cost reduction is achieved in the basic MEO process by using an alkaline electrolyte, such as but not limited to aqueous solutions of NaOH or KOH with mediator species wherein the reduced form of said mediator redox couple displays sufficient solubility in said electrolyte to allow the desired oxidation of the inorganic waste to proceed at a practical rate.

The oxidation potential of redox reactions producing hydrogen ions (i.e., both mediator species and inorganic waste molecule reactions) is inversely proportional to the electrolyte pH. Thus, with the proper selection of a redox couple mediator, it is possible, by increasing the electrolyte pH, to minimize the electric potential required to affect the desired oxidation process, thereby reducing the electric power consumed per unit mass of inorganic waste oxidized.

In this invention, when an alkaline anolyte is used, the $CO_2$ resulting from oxidation of the inorganic waste containing carbon reacts with the anolyte to form alkali metal bicarbonates/carbonates. The bicarbonate/carbonate ions circulate within the anolyte where they are reversibly oxidized to percarbonate ions either by anodic oxidation within the electrochemical cell or alternately by reacting with the oxidized form of a more powerful redox couple mediator, when present in the anolyte. The carbonate thus functions exactly as a simple anion redox couple mediator, thereby producing an oxidizing species from the waste oxidation products that it is capable of oxidizing additional inorganic waste.

Additional MEO Electrolyte Features

In one preferred embodiment of this invention, the catholyte and anolyte are discrete entities separated by a membrane, thus they are not constrained to share any common properties such as electrolyte concentration, composition, or pH (i.e., acid, alkali, or neutral). The process operates over the temperature range from approximately 0° C. to slightly below the boiling point of the electrolyte used during the oxidation of the inorganic waste.

MEO Process Augmented by Ultraviolet/Ultrasonic Energy

Decomposition of hydrogen peroxide into free hydroxyl radicals is well known to be promoted by ultraviolet (UV) irradiation. The destruction rate of inorganic waste obtained using the MEO process in this invention, therefore, is increased by UV irradiation of the reaction chamber anolyte to promote formation of additional hydroxyl free radicals. In a preferred embodiment, UV radiation is introduced into the anolyte chamber using a UV source either internal to or adjacent to the anolyte chamber. The UV irradiation decomposes hydrogen peroxide, which is produced by secondary oxidizers generated by the oxidized form of the mediator redox couple, into hydroxyl free radical. The result is an increase in the efficiency of the MEO process since the energy expended in hydrogen peroxide generation is recovered through the oxidation of inorganic materials in the anolyte chamber.

Additionally, ultrasonic energy is introduced into the anolyte chamber. Implosion of the microscopic bubbles formed by the rapidly oscillating pressure waves emanating from the sonic horn generate shock waves capable of producing extremely short lived and localized conditions of 4800° C. and 1000 atmospheres pressure within the anolyte. Under these conditions water molecules decompose into hydrogen atoms and hydroxyl radicals. Upon quenching of the localized thermal spike, the hydroxyl radicals undergo the aforementioned reactions with the inorganic waste or combine with each other to form another hydrogen peroxide molecule which then itself oxidizes additional inorganic waste.

In another preferred embodiment, the destruction rate of non-anolyte soluble inorganic waste is enhanced by affecting a reduction in the dimensions of the individual second (i.e., inorganic waste) phase entities present in the anolyte, thereby increasing the total waste surface area wetted by the anolyte and therefore the amount of waste oxidized per unit time. Immiscible liquids may be dispersed on an extremely fine scale within the aqueous anolyte by the introduction of suitable surfactants or emulsifying agents. Vigorous mechanical mixing such as with a colloid mill or the microscopic scale mixing affected by the aforementioned ultrasonic energy induced microscopic bubble implosion could also be used to affect the desired reduction in size of the individual second phase waste volumes dispersed in the anolyte. The vast majority of solid waste may be converted into a liquid phase, thus becoming treatable as above, using a variety of disruption methodologies. Examples of these methods are mechanical shearing using various rotor-stator homogenizers and ultrasonic devices (i.e., sonicators) where the aforementioned implosion generated shock wave, augmented by the 4800° C. temperature spike, mixes the liquid and solids for better access to the oxidizers.

Since water is a product of the oxidation process it requires no further energy to dispose of in the inorganic waste thus saving energy that would be expended in a thermal based process.

If the amount of water released directly from the inorganic waste and/or formed as a reaction product from the oxidation of hydrogenous waste dilutes the anolyte to an unacceptable level, the anolyte can easily be reconstituted by simply raising the temperature and/or lowering the pressure in an optional evaporation chamber to affect removal of the required amount of water. The soluble constituents of the inorganic waste are rapidly dispersed throughout the anolyte on a molecular scale while the insoluble constituents are dispersed throughout the anolyte as an extremely fine second phase using any of the aforementioned dispersal methodologies, thereby vastly increasing the waste anolyte interfacial contact area beyond that possible with an intact solid configuration and thus increasing the rate at which the inorganic waste is oxidized and the MEO efficiency.

In another preferred embodiment, increasing the surface area exposed to the anolyte enhances the destruction rate of non-anolyte solid inorganic waste. The destruction rate for any given concentration of oxidizer in solution in the anolyte is limited to the area of the solid with which the oxidizer can make contact. The embodiment used for solids contains a mechanism for multiple puncturing of the solid when it is placed in the anolyte reaction chamber basket. The punctures allow the oxidizer to penetrate into the interior of the solid, by-passing difficult to oxidize surface layers, and increase the rate of oxidation.

MEO Process Augmented with Free Radicals

The principals of the oxidation process used in this invention, in which a free radical (e.g., $.O_2H$, $.OH$, $.SO_4$, $.NO_3$,) cleaves and oxidizes inorganic compounds, results in the formation of successively smaller molecular compounds. The intermediate compounds so formed are easily oxidized during sequential reactions.

Inorganic radicals are generated in aqueous solution variants of the MEO process in this invention. Radicals have been derived from carbonate, azide, nitrite, nitrate, phosphate, phosphite, sulphite, sulphate, selenite, thiocyanate, chloride, bromide, iodide and formate ions. The MEO process may generate organic free radicals, such as sulfhydryl. When the MEO process in this invention is applied to inorganic materials they are broken down into compounds that are attacked by the aforementioned inorganic free radicals, which contribute to the oxidation process and increase the efficiency of the MEO process.

These and further and other objects and features of the invention are apparent in the disclosure, which includes the above and ongoing written specification, with the characteristics and drawings.

BRIEF DESCRIPTION OF THE DRAWINGS

FIG. 1A is a representation of a general embodiment of the present invention (with the understanding that not all of the components shown therein must necessarily be employed in all situations) and others may be added as needed for a particular application.

FIG. 1D Remote Anolyte Reaction Chamber is a schematic representation of the anolyte reaction chamber used for separating the anolyte reaction chamber from the basic MEO apparatus. This configuration allows the chamber to be a part of production line or similar use.

FIG. 3 is a representation of a general embodiment of a controller for the present invention (with the understanding that not all of the components shown therein must necessarily be employed in all situations) and others may be added as needed for a particular application.

DETAILED DESCRIPTION OF PREFERRED EMBODIMENTS

According to this present patent, the Mediated Electrochemical Oxidation (MEO) process and apparatus may be used for the destruction, conversion/recovery, and decontamination (such as equipment, containers, etc.) of all previously defined inorganic solid, liquid, and gas wastes. There are a number of embodiments involving the three modes of operation and variations in the anolyte reactions chambers depicted in FIGS. 1B through FIG. 1E. The following section will discuss various embodiments and use one in detail as an illustration.

MEO Chemistry

Mediated Electrochemical Oxidation (MEO) process chemistry described in this patent uses oxidizer species as described in Table I (simple anions redox couple mediators); Type I IPAs formed by Mo, W, V, Nb, Ta, or mixtures thereof as addenda atoms; Type I HPAs formed by incorporation into the aforementioned IPAs of any of the elements listed in Table II (heteroatoms) either singly or in combination thereof; or any HPA containing at least one heteroatom type (i.e., element) contained in both Table I and Table II; or combinations of mediator species from any or all of these generic groups. Since the anolyte and catholyte are completely separated entities, it is not necessary for both systems to contain the same electrolyte. Each electrolyte may, independent of the other, consist of an aqueous solution of acids, typically but not limited to nitric, sulfuric, or phosphoric; alkali, typically but not limited to sodium or potassium hydroxide; or neutral salt typically but not limited to sodium or potassium salts of the aforementioned strong mineral acids.

The MEO Apparatus is unique in that it accommodates the numerous choices of mediator ions and electrolytes by simply draining, flushing, and refilling the system with the mediator/electrolyte system of choice.

Because of redundancy and similarity in the description of the various mediator ions, only the iron and sulfuric acid combination is discussed in detail. However, it is to be understood that the following discussion of the ferric/ferrate, $(Fe^{+3})/(FeO_4^{-2})$ redox couple reaction in sulfuric acid ($HNO_3$) also applies to all the aforementioned oxidizer species and electrolytes described at the beginning of this section. Furthermore, the following discussions of the interaction of ferrate ions with aqueous electrolytes to produce the aforementioned free radicals also applies to all aforementioned mediators having an oxidation potential sufficient to be classified superoxidizers (SO). An SO has an oxidation potential at least equal to that of the redox couple $Ce^{+3}/Ce^{+4}$ which has a potential of approximately 1.7 volts at 1 molar, 25° C. and pH 1.

Figure 1A:
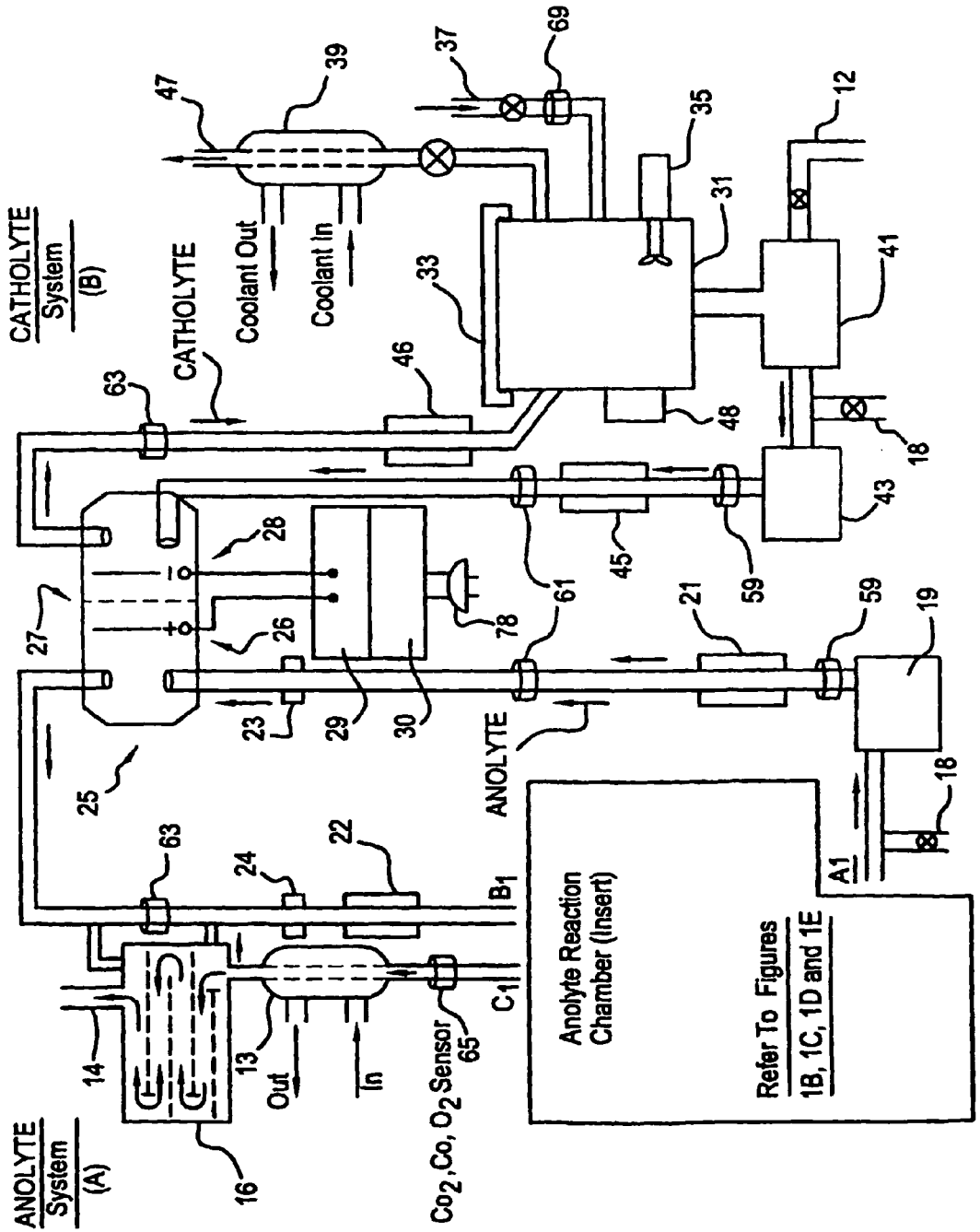
FIG. 1A MEO Apparatus Diagram is a schematic representation of a system for oxidizing inorganic waste materials.

FIG. 1A shows a MEO Apparatus in a schematic representation for oxidizing inorganic waste. At the anode of the electrochemical cell 25 Fe(III) ions ($Fe^{+3}$, ferric) are oxidized to Fe(VI) ions ($FeO_4^{-2}$, ferrate),

$$Fe^{+3} + 4H_2O \rightarrow FeO_4^{-2} + 8H^+ + 3e^-$$

If the anolyte temperature is sufficiently high, typically above 50° C., the Fe(VI) species may undergo a redox reaction with the water in the aqueous anolyte. The oxidation of water proceeds by a sequence of reactions producing a variety of intermediate reaction products, some of which react with each other. A few of these intermediate reaction products are highly reactive free radicals including, but not limited to the hydroxyl (.OH) and hydrogen peroxy or perhydroxyl (.HO₂) radicals. Additionally, the mediated oxidizer species ions may interact with anions present in the acid or neutral salt electrolyte (e.g., $NO_3^-$, $SO_4^{-2}$, or $PO_4^{-3}$, etc.) to produce free radicals typified by, but not limited to .O₂H, .OH, .SO₄, .NO₃, or the anions may undergo direct oxidation at the anode of the cell. The population of hydroxyl free radicals may be increased by ultraviolet irradiation of the anolyte (see ultraviolet source 11) in the reaction chambers 5(a,b,c) and buffer tank 20 to cleave the hydrogen peroxide molecules, and intermediate reaction products, into two such radicals. Free radical populations may also be increased by ultrasonic vibration (see ultrasonic source 9) induced by the aforementioned implosion generated shock wave, augmented by the 4800° C. temperature and 1000 atmospheres pressure spikes.

These secondary oxidation species are capable of oxidizing inorganic materials and thus act in consort with Fe(VI) ions to oxidize the inorganic materials.

The mediator oxidizing species reacts in the anolyte to produce the secondary oxidizer species (free radicals). The free radical generated reacts with and oxidizes a reductant. The reductants are strong reducing agents and they reduce the halogenated inorganics which results in their dehalogenation. The reduced halogens remain in solution as halogen ions. The remaining inorganic molecules are oxidized. The chlorine remains in solution and the remaining inorganic molecules are further decomposed into ions in solution. A resin column to avoid any release into the atmosphere may be used to remove the chlorine. The oxidizing species is chosen from Table 1 so as to avoid the forming of precipitates such as silver chloride. An example of a suitable oxidizer from Table I would be the selection of the iron oxidizer being discussed in the foregoing paragraphs.

The oxidizers react with the inorganic waste to produce ions in solution. These processes occur in the anolyte on the anode side of the system in the reaction chambers 5(a,b,c,d), buffer tank 20, and throughout the anolyte system when in solution. Addition of ferric ions to non-iron-based MEO systems are also proposed as this has the potential for increasing the overall rate of inorganic waste oxidation compared to the non-iron MEO system alone. Again it is to be understood this discussion of the ferric/ferrate redox couple also applies to all the aforementioned oxidizer species described at the beginning of this section) An example is considering the two step process, the first step of which is to electrochemically form a $FeO_4^{-2}$ ion. In the second step the $FeO_4^{-2}$ ion oxidizes a mediator ion, from its reduced form (e.g., sulfate) to its oxidized form (e.g., peroxysulfate), faster than by the direct anodic oxidation of the sulfate ion itself. Thus there is an overall increase in the rate of inorganic waste destruction.

Membrane 27 separates the anode and the cathode chambers in the electrochemical cell 25. Hydrogen ions ($H^+$) or hydronium ions ($H_3O^+$) travel through the membrane 27 due to the electrical potential from the dc power supply 29 applied between the anode(s) 26 and cathodes(s) 28. In the catholyte the hydrogen ions are reduced to hydrogen gas $$2H^+ + 2e^- \rightarrow H_2$$

The hydrogen ions ($H^+$) or hydronium ions ($H_3O^+$) will evolve as hydrogen gas at the cathode. The hydrogen gas is diluted with the air from the air sparge and released to the atmosphere or the evolved hydrogen gas can be fed to devices that use hydrogen as a fuel such as the fuel cells. The hydrogen may undergo purification prior to use (e.g., palladium diffusion, etc.) and/or solid state storage (e.g., adsorption in zirconium, etc.).

In some cases oxygen is evolved at the anode due to the over voltage necessary to create the oxidation species of some of the mediator ions. The efficiency of these mediators is somewhat less under those conditions. The evolved oxygen can be fed to the devices that use hydrogen as a fuel such as the fuel cells. Using the evolved oxygen to enrich the air above its nominal oxygen content of 20.9 percent increases the efficiency of fuel cells deriving their oxygen supply from ambient air.

The overall MEO process may be operated in three different modes (oxidation, conversion/recovery, and decontamination). In the first mode (oxidation) the process runs until the inorganic materials are totally decomposed into their higher oxidation level. In the second mode (conversion/recovery) the process is operated such that the inorganic materials are oxidized to an intermediate stage or a chemical intermediate. In the conversion mode, the chemical intermediate that results are not toxic or hazardous material and may be disposed of in a safe and healthy waste disposal system In the recovery mode, the process is operated until an inorganic material is produced that can be used, thus turning inorganic waste material into a recovered product.

The third mode (decontamination) involves contaminated equipment, instruments, glassware, containers (such as 50 gallon drums) and materials (e.g., clothing, rags, absorbents, etc.). In this mode the MEO process oxidizes the inorganics that have contaminated them. These items are placed in an anolyte reaction chamber (see FIG. 1C) or these items act as an anolyte reaction chamber (see FIG. 1E) and the electrolyte containing the oxidizing species is introduced into the chamber. The MEO process cleans the contaminated items rendering them non-toxic and safe to reuse or dispose of them. In this mode the MEO process is used to decontaminate these items and clean them for future use, or disposal has been affected (resulting in decontamination) or modified to stop the process at a point where the oxidation of the inorganics is incomplete but the resulting intermediate materials are benign and do not need further treatment (resulting in decontamination).

In modes one and three the inorganic waste is converted to inorganic compounds in solution or as a precipitate, which may be extracted by the inorganic compound removal and treatment system 15.

The MEO process will proceed until complete oxidation of the inorganic waste on contaminated equipment, instruments, glassware, containers (such as 50 gallon drums) and materials (e.g., clothing, rags, absorbents, etc.).

The MEO process may proceed until complete oxidation of the inorganic waste has been affected or modified to stop the process at a point where the oxidation of the inorganic waste is incomplete but: a) the inorganic materials are converted into benign materials and do not need further treatment; b) the inorganic materials may be used in the form they have been oxidized to and thus would be recovered for future use as an intermediate chemical product.

The entireties of U.S. Pat. Nos. 4,686,019; 4,749,519; 4,874,485; 4,925,643; 5,364,508; 5,516,972; 5,745,835; 5,756,874; 5,810,995; 5,855,763; 5,911,868; 5,919,350; 5,952,542; and 6,096,283 are incorporated herein by reference for their relevant teachings.

Each of the following patent(s)/co-pending applications are incorporated herein by reference in their entireties:
U.S. Pat. No. 6,402,932 issued Jun. 11, 2002.
U.S. application Ser. No. 10/263,810 filed Oct. 4, 2002.
U.S. application Ser. No. 10/127,604 filed Apr. 23, 2002.
U.S. Provisional Application Ser. No. 60/409,202 filed Sep. 10, 2002.
U.S. Provisional Application Ser. No. 60/477,162 filed Jun. 10, 2003.
U.S. Provisional Application Ser. No. 60/477,162 filed Jun. 10, 2003.
PCT/US03/02151 based on U.S. Provisional Application Ser. No. 60/350,352 filed Jan. 24, 2002.
PCT/US03/02152 based on U.S. Provisional Application Ser. No. 60/350,377 filed Jan. 24, 2002.
PCT/US03/02153 based on U.S. Provisional Application Ser. No. 60/350,378 filed Jan. 24, 2002.
PCT/US03/13051 based on U.S. Provisional Application Ser. No. 60/375,430 filed Apr. 26, 2002.
PCT/US03/04065 filed Feb. 12, 2003.
PCT/US02/33732 based on U.S. Provisional Application Ser. No. 60/330,436 filed Oct. 22, 2001.
PCT/US02/32040 based on U.S. Provisional Application Ser. No. 60/327,306 filed Oct. 9, 2001.
PCT/US03/23491 based on U.S. Provisional Application Ser. No. 60/398,808 filed Jul. 29, 2003.

MEO Apparatus

A schematic drawing of the MEO apparatus shown in FIG. 1A MEO Apparatus Diagram illustrates the application of the MEO process to the oxidation of inorganic waste. The MEO apparatus is composed of two separate closed-loop systems containing an electrolyte solution composed of anolyte and catholyte solutions. The anolyte and catholyte solutions are contained in the anolyte (A) system and the catholyte (B) system, respectively. These two systems are discussed in detail in the following paragraphs.

There are numerous combinations of five anolyte reaction chambers and three modes of operation.

Anolite System (A)

The bulk of the anolyte resides in the anolyte reaction chambers 5(a,b,c,d) and the buffer tank 20. The anolyte portion of the electrolyte solution contains for example $Fe^{+3}$/$FeO_4^{-2}$ redox couple anions and secondary oxidizing species (e.g., free radicals, $H_2O_2$, etc.).

Referring to FIG. 1A, the inorganic waste may be a liquid, solid, gas, a mixture of solids, liquids, and gases, or combined waste. FIGS. 1B through 1F provide preferred embodiments of the anolyte reaction chambers 5a through 5e and buffer tank 20.

Figure 1B:
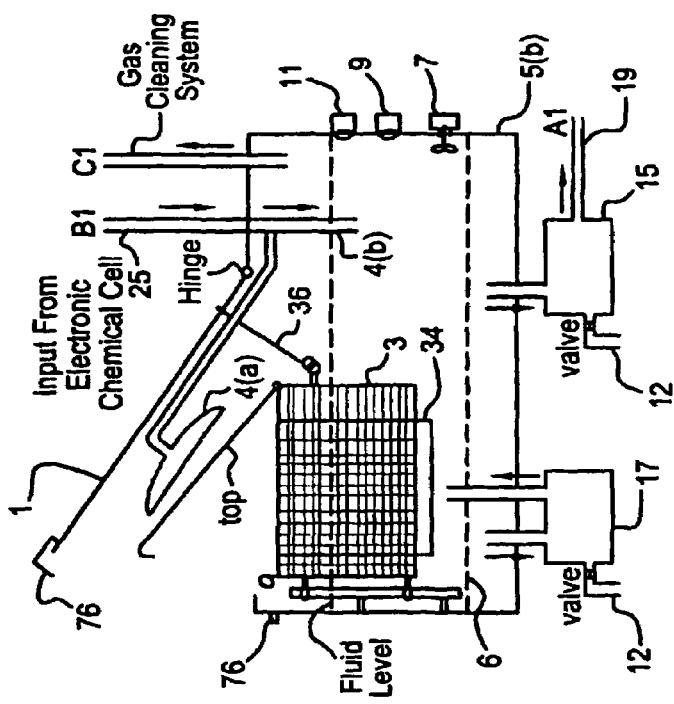
FIG. 1B Anolyte Reaction Chamber for Liquids, Mixtures, Small Particulate and with Continuous Feed is a schematic representation of the anolyte reaction chamber used for inorganic fluids, and mixtures which include small particulate. This chamber accommodates a continuous feed of these materials into the chamber.

The anolyte reaction chamber 5a in FIG. 1B is designed for liquids, small particulate and continuous feed operations. The inorganic waste is introduced into the anolyte reaction chamber 5a through the input pump 10 connected to the source of the inorganic waste to be oxidized. The inorganic waste is pumped into the chamber 5a, which contains the anolyte used to oxidize that inorganic waste. The apparatus continuously circulates the anolyte portion of the electrolyte directly from the electrochemical cell 25 through the anolyte reaction chamber 5a to maximize the concentration of oxidizing species contacting the waste. The anolyte is introduced into the anolyte reaction chamber 5a through the spray head 4(*a*) and stream head 4(*b*). The two heads are designed to increase the exposure of the inorganic waste to the anolyte by enhancing the mixing in the anolyte reaction chamber 5a. Introducing the anolyte into the anolyte reaction chamber 5a as a spray onto the anolyte surface promotes contact with (i.e., oxidation of) any immiscible organic surface layers present. A filter 6 is located at the base of the reaction chamber 5a to limit the size of the solid particles to approximately 1 mm in diameter (i.e., smaller than the minimum dimension of the anolyte flow path in the electrochemical cell 25) thereby preventing solid particles large enough to clog the electrochemical cell 25 flow paths from exiting the anolyte reaction chamber 5a. Contact of the oxidizing species with incomplete oxidation products that are gaseous at the conditions within the anolyte reaction chamber 5a may be further enhanced by using conventional techniques for promoting gas/liquid contact (e.g., ultrasonic vibration 9, mechanical mixing 7). An ultraviolet source 11 is introduced into the anolyte reaction chamber 5a to decompose the hydrogen peroxide formed by the MEO process into free hydroxyl radicals.

Figure 1C:
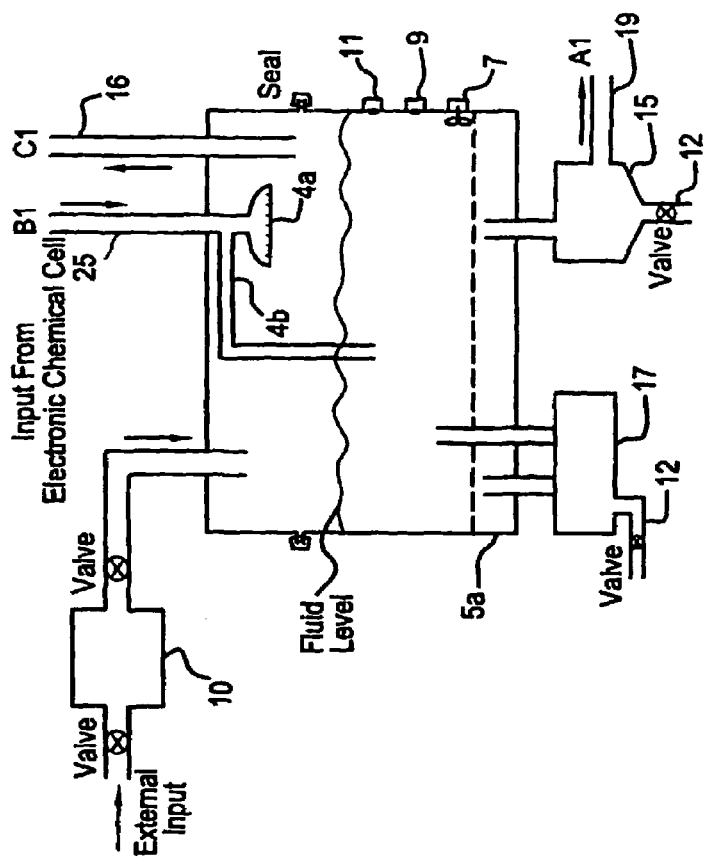
FIG. 1C Anolyte Reaction Chamber for Solids, Mixtures, and Larger Particulate and with Batch Operation is a schematic representation of the anolyte reaction chamber used for solids, and mixtures that include large particulate. This chamber may be used for batch mode processing of inorganic wastes.

The anolyte reaction chamber 5b in FIG. 1C is designed for solids, mixtures and batch operations. The hinged lid 1 is lifted, and the top of the basket 3 is opened. The inorganic waste is introduced into the basket 3 in the reaction chamber 5b where the solid waste remains while the liquid portion of the waste flows into the anolyte. The basket top is closed and the basket 3 is lowered by a lever 36 connected to the lid 1 into the anolyte such that all its contents are held submerged in the anolyte throughout the oxidization process. Lid 1 has a seal around the opening and it is locked before operation begins.

A mechanical device (penetrator 34) is incorporated into the basket 3 that create multiple perforations in the outer layers of the solid inorganic waste so that the anolyte can penetrate into the waste. This penetration speeds up the oxidation of the solid inorganic waste by increasing the surface area exposed to the anolyte oxidizer, and allowing said oxidizer immediate access to portions of the aforementioned waste that are encased in (i.e., protected by) more difficult to oxidize surrounding outer layers.

The apparatus continuously circulates the anolyte portion of the electrolyte directly from the electrochemical cell 25 through the anolyte reaction chamber 5b to maximize the concentration of oxidizing species contacting the waste. The anolyte enters the anolyte reaction chamber 5b and is injected through two nozzles; one a spray head 4(*a*) to distribute the anolyte throughout the anolyte reaction chamber 5b, and the second is a stream head 4(*b*) to promote circulation and turbulence in the anolyte in the anolyte reaction chamber 5b. Introducing the anolyte into the anolyte reaction chamber 5b as a spray onto the anolyte surface promotes contact with (i.e., oxidation of) any immiscible organic surface layers present. A filter 6 is located at the base of the reaction chamber 5b to limit the size of the solid particles to approximately 1 mm in diameter (i.e., smaller than the minimum dimension of the anolyte flow path in the electrochemical cell 25) thereby preventing solid particles large enough to clog the electrochemical cell 25 flow paths from exiting the anolyte reaction chamber 5b. Contact of the oxidizing species with incomplete oxidation products that are gaseous at the conditions within the reaction chamber 5b may be further enhanced by using conventional techniques for promoting gas/liquid contact (e.g., ultrasonic vibration 9, mechanical mixing 7). An ultraviolet source 11 is introduced into the anolyte reaction chamber 5b to decompose the hydrogen peroxide formed by the MEO process into free hydroxyl radicals.

The anolyte reaction chamber 5c in FIG. 1D is designed to use an anolyte reaction chamber that is exterior to the basic MEO apparatus. Typical of this configuration is an apparatus that is similar to an ultrasonic bath. The anolyte reaction chamber 5c may be integrated into a production process to be used to oxidize inorganics as a part of the process. The anolyte reaction chamber 5c may be connected to the basic MEO apparatus through tubing and a pumping system. The anolyte is pumped from the buffer tank 20 in the basic MEO apparatus by the pump 8 where it is introduced into the anolyte reaction chamber 5c through spray head 4(*a*) as a spray onto the anolyte surface thereby promoting contact with (i.e., oxidation of) any immiscible inorganic surface layers present in addition to reacting with (i.e., oxidizing) the inorganic waste dissolved, suspended or submerged within the anolyte in the reaction chamber 5c. The inlet to pump 8 is protected by an in-line screen filter 6 which prevents solid particles large enough to clog the spray head 4(*a*) from exiting the buffer tank 20. Contact of the oxidizing species with incomplete oxidation products that are gaseous at the conditions within the anolyte reaction chamber 5c may be further enhanced by using conventional techniques for promoting gas/liquid contact (e.g., ultrasonic vibration 9, mechanical mixing 7). An ultraviolet source 11 is introduced into the anolyte reaction chamber 5c to decompose the hydrogen peroxide formed by the MEO process into free hydroxyl radicals. The input pump 10 pumps the anolyte and inorganic waste liquid in the anolyte reaction chamber 5c back to the buffer tank in the basic MEO apparatus through a return tube protected by an in-line screen filter 6 which prevents solid particles large enough to clog the spray head 4(*a*) from exiting the reaction chamber 5c. A third tube is connected to the anolyte reaction chamber 5c to pump out any gas that is present from the original contents or from the MEO process. The gas is pumped by the air pump 32. The return gas tube is submerged in the buffer tank 20 in the basic MEO system so as to oxidize any volatile organic compounds in the gas to $CO_2$ before release to the gas cleaning system 16. Contact of the oxidizing species with incomplete oxidation products that are gaseous at the conditions within the anolyte reaction chamber 5c may be further enhanced by using conventional techniques for promoting gas/liquid contact (e.g., ultrasonic vibration 9, mechanical mixing 7). The apparatus continuously circulates the anolyte portion of the electrolyte directly from the electrochemical cell 25 through the buffer tank 20 to maximize the concentration of oxidizing species contacting the waste.

The hinged lid 1 is lifted, and the top of the basket 3 is opened. The inorganic waste is introduced into the wastebasket 3 in the anolyte reaction chamber 5c where the solid waste remains while the liquid portion of the waste flows into the anolyte. The basket 3 top and the lid 1 are closed and lid 1 has a seal around the opening and it is locked before operation begins. With basket 3 lid closed, the basket 3 is lowered into the anolyte so that all its contents are held submerged in the anolyte throughout the oxidization process.

A mechanical device (penetrator 34) may be incorporated into the basket 3 in the anolyte reaction chamber 5c that creates multiple perforations in the outer portion of the solid inorganic waste so that the anolyte can rapidly penetrate into the interior of the waste. The penetrator 34 serves the same purpose it does in the anolyte reaction chamber 5b described in the foregoing section. A filter 6 is located at the base of the buffer tank 20 to limit the size of the solid particles to approximately 1 mm in diameter (i.e., smaller than the minimum dimension of the anolyte flow path in the electrochemical cell 25) thereby preventing solid particles large enough to clog the electrochemical cell 25 flow paths from exiting the buffer tank (20).

Figure 1E:
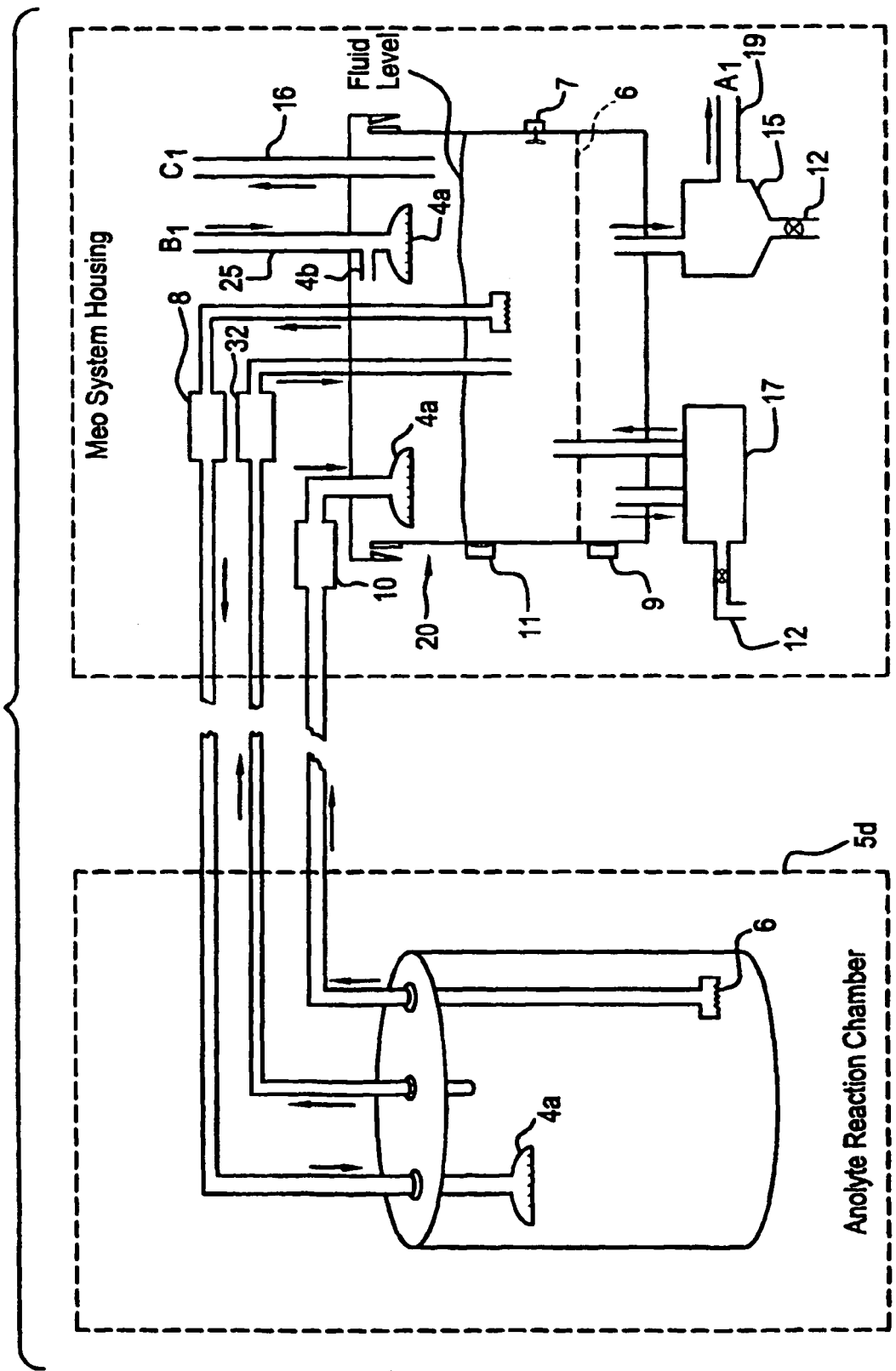
FIG. 1E Contaminated Equipment Used as the Anolyte Reaction Chamber Exterior is a schematic representation of a contaminated container serving the role of the anolyte reaction chamber that is not a part of the MEO apparatus. Typical of such contaminated containers are storage tanks for liquids and metallurgical plating baths. This configuration is used to decontaminate items and clean them for future use or disposal.

The anolyte reaction chamber 5d in FIG. 1E is designed to use a closed container exterior to the basic apparatus as the anolyte reaction chamber 5d. FIG. 1E illustrates one example of an exterior container, which in this case is a metal vessel, such as a 50 gallon drum containing inorganic waste. The drum may be connected to the basic MEO apparatus through tubing and a pumping system. The anolyte is pumped by the pump 8 from the buffer tank 20 in the basic MEO apparatus into the anolyte reaction chamber 5d where it reacts with the contents and oxidizes the inorganic waste. The anolyte stream is oscillated within the anolyte reaction chamber 5d to allow for thorough mixing and for cleaning of the walls of the anolyte reaction chamber 5d. The input pump 10 pumps the anolyte and inorganic waste liquid in the anolyte reaction chamber 5d back to the buffer tank in the basic MEO apparatus through a return tube protected by an in-line screen filter 6 which prevents solid particles large enough to clog the spray head 4(a) from exiting the anolyte reaction chamber 5d. A third tube is connected to the anolyte reaction chamber 5d through the air pump 32 to pump out any gas that is present from the original contents or from the MEO process. The return gas tube is submerged below the anolyte level in the buffer tank 20 in the basic MEO system so as to oxidize any volatile organic compounds in the gas to $CO_2$ before release to the gas cleaning system 16.

The anolyte from the electrochemical cell 25 is introduced into the buffer tank 20 through the spray head 4(a) and stream head 4(b). The two heads are designed to increase the exposure of the inorganic waste to the anolyte by enhancing the mixing in the anolyte reaction chambers. Introducing the anolyte into the buffer tank 20 as a spray onto the anolyte surface promotes contact with (i.e., oxidation of) any immiscible inorganic surface layers present.

The MEO apparatus continuously circulates the anolyte portion of the electrolyte directly from the electrochemical cell 25 into the buffer tank 20 to maximize the concentration of oxidizing species contacting the waste. A filter 6 is located at the base of the buffer tank to limit the size of the solid particles to approximately 1 mm in diameter (i.e., smaller than the minimum dimension of the anolyte flow path in the electrochemical cell 25). Contact of the oxidizing species with incomplete oxidation products that are gaseous at the conditions within the buffer tank 20 may be enhanced by using conventional techniques for promoting gas/liquid contact (e.g., ultrasonic vibration 9, mechanical mixing 7). An ultraviolet source 11 is introduced into the buffer tank 20 to decompose the hydrogen peroxide formed by the MEO process into free hydroxyl radicals.

All surfaces of the apparatus in contact with the anolyte are composed of stainless steel, glass, or nonreactive polymers (e.g., PTFE, PTFE lined tubing, etc), PTFE coated metallic tubing, glazed ceramic, glazed metallic, metal oxides, and glazed composite from metallurgic isostatic pressing. These materials provide an electrolyte containment boundary to protect the components of the MEO apparatus from being oxidized by the electrolyte.

The anolyte circulation system contains a pump 19 and a removal and treatment system 15 (e.g., filter, centrifuge, hydrocyclone, etc.) to remove any insoluble inorganic compounds that form as a result of mediator or electrolyte ions reacting with anions of or containing halogens, sulfur, phosphorous, nitrogen, etc. that may be present in the waste stream thus preventing formation of unstable compounds (e.g., perchlorates, etc.). The anolyte is then returned to the electrochemical cell 25, where the oxidizing species are regenerated, which completes the circulation in the anolyte system (A).

The residue of the inorganic compounds is flushed out of the treatment system 15 during periodic maintenance if necessary. If warranted, the insoluble inorganic compounds are converted to water-soluble compounds using any one of several chemical or electrochemical processes.

Waste is added to the reaction chambers 5(a,b,c,d) either continuously or in the batch mode depending on the anolyte reaction configuration chosen.

The MEO system apparatus incorporates two methods that may control the rate of destruction of inorganic waste and control the order of which inorganic molecular bonds are broken. In the first method the anolyte temperature is initially at or below the operating temperature and subsequently increased by the thermal controls 21 and 22 until the desired operating temperature for the specific waste stream is obtained. In the second method the inorganic waste is introduced into the apparatus, with the concentration of electrochemically generated oxidizing species in the anolyte being limited to some predetermined value, between zero and the maximum desired operating concentration, for the waste stream by controlling of the electric current in the electrochemical cell 25 with the dc power supply 29 and subsequently increased to the desired operating concentration. These two methods can be used in combination.

The electrolyte is composed of an aqueous solution of mediator species and electrolytes appropriate for the species selected and is operated within the temperature range from approximately 0° C. to slightly below the boiling point of the electrolytic solution, usually less than 100° C., at a temperature or temperature profile most conducive to the desired waste destruction rate (e.g., most rapid, most economical, etc.). The acid, alkaline, or neutral salt electrolyte used is determined by the conditions in which the species may exist.

Considerable attention has been paid to halogens, especially chlorine and their deleterious interactions with silver mediator ions, however this is of much less concern or importance to this invention. The wide range of properties (e.g., oxidation potential, solubility of compounds, cost, etc.) of the mediator species claimed in this patent allows selection of a single or mixture of mediators either avoiding formation of insoluble compounds, easily recovering the mediator from the precipitated materials, or being sufficiently inexpensive so as to allow the simple disposal of the insoluble compounds as waste, while still maintaining the capability to oxidize the inorganic waste economically.

The waste destruction process may be monitored by several electrochemical and physical methods. First, various cell voltages (e.g., open circuit, anode vs. reference electrode, ion specific electrode, etc.) yield information about the ratio of oxidized to reduced mediator ion concentrations which may be correlated with the amount of reducing agent (i.e., inorganic waste) either dissolved in or wetted by the anolyte. Second, if a color change accompanies the transition of the mediator species between it's oxidized and reduced states (e.g., heteropoly blues, etc.), the rate of decay of the color associated with the oxidized state, under zero current conditions, could be used as a gross indication of the amount of reducing agent (i.e., oxidizable waste) present. If no color change occurs in the mediator, it may be possible to select another mediator to simply serve as the oxidization potential equivalent of a pH indicator. Such an indicator is required to have an oxidation potential between that of the working mediator and the inorganic species, and a color change associated with the oxidization state transition.

The anolyte is circulated into the reaction chambers 5(a,b,c,d) through the electrochemical cell 25 by pump 19 on the anode 26 side of the membrane 27. A membrane 27 in the electrochemical cell 25 separates the anolyte portion and catholyte portion of the electrolyte.

Small thermal control units 21 and 22 are connected to the flow stream to heat or cool the anolyte to the selected temperature range. The heat exchanger 23 can be located immediately upstream from the electrochemical cell 25 to lower the anolyte temperature within the cell to the desired level. Another heat exchanger 24 can be located immediately upstream of the anolyte reaction chamber inlet to control the anolyte temperature in the reaction chamber to within the desired temperature range to affect the desired chemical reactions at the desired rates.

The electrochemical cell 25 is energized by a DC power supply 29, which is powered by the AC power supply 30. The DC power supply 29 is low voltage high current supply usually operating in the range, for example 0.1 v to 10 v DC, but not limited to that range. The AC power supply 30 operates off a typical 110 v AC line for the smaller units and 240 v AC for the larger units.

The oxidizer species population produced by electrochemical generation (i.e., anodic oxidation) of the oxidized form of the redox couples referenced herein can be enhanced by conducting the process at low temperatures, thereby reducing the rate at which thermally activated parasitic reactions consume the oxidizer.

Reaction products resulting from the oxidation processes occurring in the anolyte system (A) that are gaseous at the anolyte operating temperature and pressure are discharged to the condenser 13. The more easily condensed products of incomplete oxidation are separated in the condenser 13 from the anolyte off-gas stream and are returned to the anolyte reaction chamber 5(a,b,c) or the buffer tank 20 for further oxidation. The non-condensable incomplete oxidation products are reduced to acceptable levels for atmospheric release by a gas cleaning system 16. The gas cleaning system 16 is not a necessary component of the MEO apparatus for the oxidation of most types of inorganic waste.

If the gas cleaning system 16 is incorporated into the MEO apparatus, the anolyte off-gas is contacted in a counter current flow gas scrubbing system in the off-gas cleaning system 16 wherein the noncondensibles from the condenser 13 are introduced into the lower portion of the column through a flow distribution system of the gas cleaning system 16 and a small side stream of freshly oxidized mediator ions in the anolyte direct from the electrochemical cell 25 is introduced into the upper portion of the column. This results in the gas phase continuously reacting with the oxidizing mediator species as it rises up the column past the down flowing anolyte. Under these conditions the gas about to exit the top of the column may have the lowest concentration of oxidizable species and also be in contact with the anolyte having the highest concentration of oxidizer species thereby promoting reduction of any air pollutants present down to levels acceptable for release to the atmosphere. Gas-liquid contact within the column may be promoted by a number of well established methods (e.g., packed column, pulsed flow, ultrasonic mixing, etc,) that does not result in any meaningful backpressure within the anolyte flow system. Anolyte exiting the bottom of the countercurrent scrubbing column is discharged into the anolyte reaction chamber 5(a,b,c) or buffer tank 20 and mixed with the remainder of the anolyte. Unique waste compositions may result in the generation of unusual gaseous products that could more easily be removed by more traditional air pollution technologies. Such methodologies could be used in series with the afore-described system as a polishing process treating the gaseous discharge from the countercurrent column, or if advantageous, instead of it. Benign inorganic and organic gases and water vapor are vented 14 out of the system.

An optional inorganic compound removal and treatment system 15 is used should there be more than trace amount of halogens, or other precipitate forming anions present in the inorganic waste being processed, thereby precluding formation of unstable oxycompounds (e.g., perchlorates, etc.).

The MEO process proceeds until complete oxidation of the inorganic waste has been affected or may be modified to stop the process at a point where the oxidation of the inorganic waste is incomplete. The reason for stopping the process is that: a) the inorganic materials are benign and do not need further treatment; or b) the inorganic materials may be used in the form they have been oxidized and thus would be recovered for that purpose. The inorganic compounds recovery system 17 is used to perform this process.

Catholyte System (B)

The bulk of the catholyte is resident in the catholyte reservoir 31. The catholyte portion of the electrolyte is circulated by pump 43 through the electrochemical cell 25 on the cathode 28 side of the membrane 27. The catholyte portion of the electrolyte flows into a catholyte reservoir 31. All surfaces of the apparatus in contact with the catholyte are composed of acid and alkaline resistant materials.

Small thermal control units 45 and 46 are connected to the catholyte flow stream to heat or cool the catholyte to the selected temperature range.

External air is introduced through an air sparge 37 into the catholyte reservoir 31. In the case where nitrogen compounds (such as nitrates) are used in the catholyte, the oxygen contained in the air oxidizes any nitrous acid and the small amounts of nitrogen oxides ($NO_x$), produced by the cathode reactions. Contact of the oxidizing gas with nitrogen compounds (nitrous acid) may be enhanced by using conventional techniques for promoting gas/liquid contact such as ultrasonic vibration 48, mechanical mixing 35, etc.

Systems using non-nitric acid catholytes may also require air sparging to dilute and remove off-gas such as hydrogen. An off-gas cleaning system 39 is used to remove any unwanted gas products (e.g. $NO_2$, etc.). The cleaned gas stream, combined with the unreacted components of the air introduced into the system is discharged through the atmospheric vent 47.

Optional anolyte recovery system 41 is positioned on the catholyte side. Some mediator oxidizer ions may cross the membrane 27 and this option is available if it is necessary to remove them through the anolyte recovery system 41 to maintain process efficiency or cell operability, or their economic worth necessitates their recovery. Operating the electrochemical cell 25 at higher than normal membrane 27 current densities (i.e., above about 0.5 amps/cm$^2$) increases the rate of waste destruction, but also results in increased mediator ion transport through the membrane into the catholyte. It may be economically advantageous for the electrochemical cell 25 to be operated in this mode. It is advantageous whenever the replacement cost of the mediator species or removal/recovery costs are less than the cost benefits of increasing the waste throughput (i.e., oxidation rate) of the electrochemical cell 25. Increasing the capitol cost of expanding the size of the electrochemical cell 25 can be avoided by using this operational option.

MEO Controller

Figure 3:
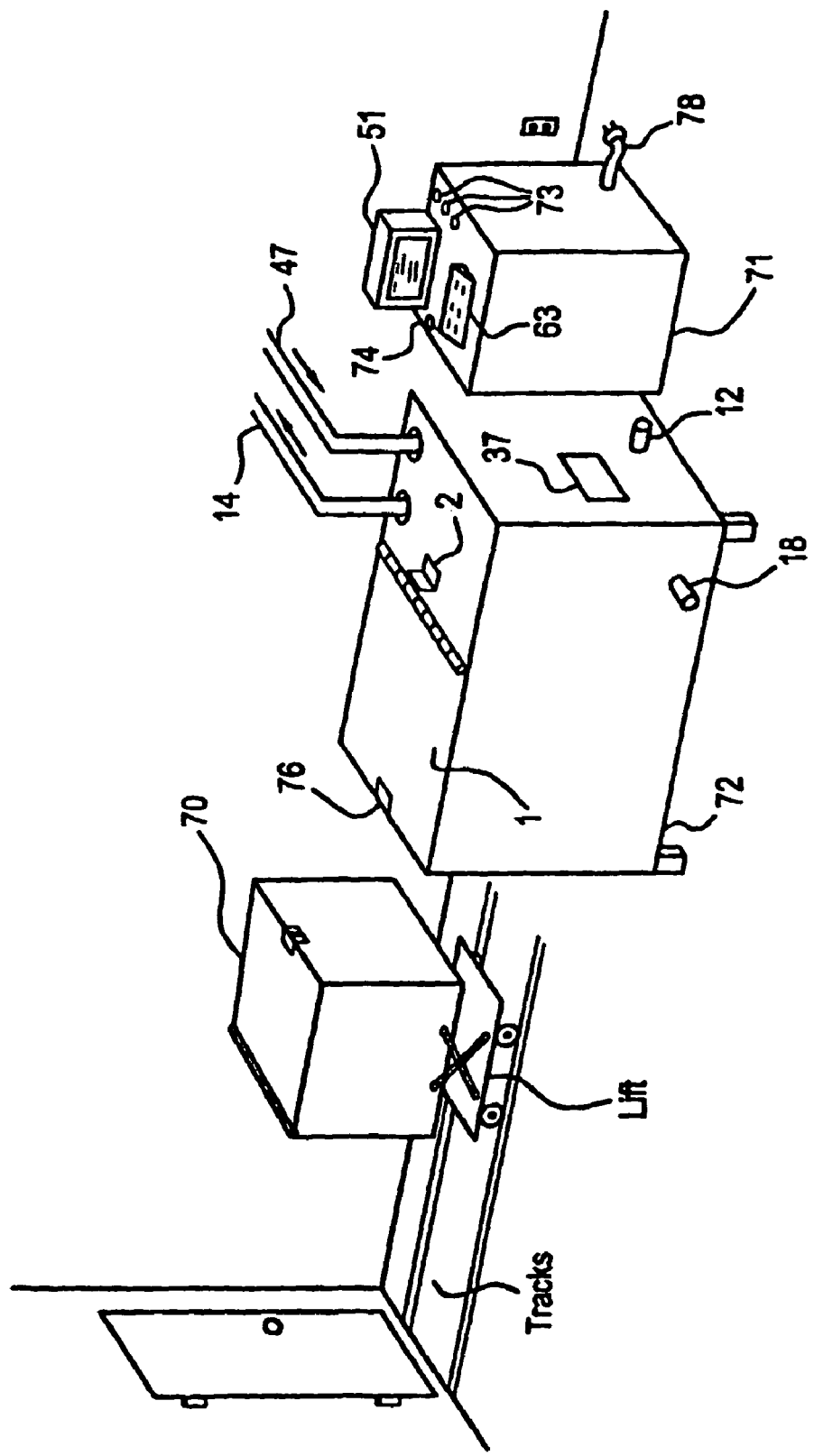
FIG. 3 MEO Controller for System Model 5.c is a schematic representation of the MEO electrical and electronic systems.

An operator runs the MEO Apparatus (FIG. 1A) by using the MEO Controller depicted in FIG. 3 MEO Controller for System Model 5.d. The controller 49 with microprocessor is connected to a monitor 51 and a keyboard 53. The operator inputs commands to the controller 49 through the keyboard 53 responding to the information displayed on the monitor 51. The controller 49 runs a program that sequences the steps for the operation of the MEO apparatus. The program has pre-programmed sequences of standard operations that the operator may follow or may choose his own sequences of operations. The controller 49 allows the operator to select his own sequences within limits that assure a safe and reliable operation. The controller 49 sends digital commands that regulates the electrical power (AC 30 and DC 29) to the various components in the MEO apparatus; pumps 19 and 43, mixers 7 and 35, thermal controls 21, 22, 45, 46, ultraviolet sources 11, ultrasonic sources 9 and 48, vent 14, air sparge 37, and electrochemical cell 25. The controller receives component response and status from the components. The controller sends digital commands to the sensors to access sensor information through sensor responses. The sensors in the MEO apparatus provide digital information on the state of the various components. Sensors measure flow rate 59, temperature 61, pH 63, venting 65, degree of oxidation 67, air sparge sensor 69, etc. The controller 49 receives status information on the electrical potential (voltmeter 57) across the electrochemical cell, or individual cells if a multi-cell configuration, and between the anode(s) and reference electrodes internal to the cell(s) 25 and the current (ammeter 55) flowing between the electrodes within each cell.

Example System Model

A preferred embodiment, MEO System Model 5.c (shown in FIG. 2 MEO System Model 5.c) is sized for use for a small to mid-size application for the oxidation of inorganic waste associated with an industrial process such as a metallurgical cleaning system. This section uses the specific combination of buffer tank 20 (FIG. 1D) and operation mode number one to illustrate a typical MEO apparatus covered by this patent. This embodiment depicts a configuration using the system apparatus presented in FIGS. 1A and 1D. Other preferred embodiments (representing FIGS. 1B, 1C, and 1E have differences in the external configuration and size but are essentially the same in internal function and components as depicted in FIGS. 1A and 1D. The preferred embodiment in FIG. 2 comprises a housing 72 constructed of metal or high strength plastic surrounding the electrochemical cell 25, the electrolyte and the foraminous basket 3. The AC power is provided to the AC power supply 30 by the power cord 78. A monitor screen 51 is incorporated into the housing 72 for displaying information about the system and about the waste being treated. Additionally, a control keyboard 53 is incorporated into the housing 72 for inputting information into the system. The monitor screen 51 and the control keyboard 53 may be attached to the system without incorporating them into the housing 72. In a preferred embodiment, status lights 73 are incorporated into the housing 72 for displaying information about the status of the treatment of the inorganic waste material. An air sparge 37 is incorporated into the housing 72 to allow air to be introduced into the catholyte reservoir 31 below the surface of the catholyte. In addition, a vent 14 is incorporated into the housing 72 to allow for release from the anolyte reaction chamber 5a via the gas cleaning system 16 housed within any benign inorganic and organic gases. In a preferred embodiment, the housing includes means for cleaning out the MEO waste treatment system, including a flush(s) 18 and drain(s) 12 through which the anolyte and catholyte pass. The preferred embodiment further comprises an atmospheric vent 47 facilitating the releases of gases into the atmosphere from the catholyte reservoir 31 via the gas cleaning system 39. Other preferred embodiment systems are similar in nature but are scaled up in size to handle a larger capacity of waste, such as incinerator replacement units.

The system has a control keyboard 53 for input of commands and data. The On/Off button 74 is used to turn the apparatus power on and off. There is a monitor screen 51 to display the systems operation and functions. Below the keyboard 53 and monitor screen 51 are the status lights 73 for on, off, and standby.

The external anolyte reaction chamber 5c may accept inorganic waste and is connected to the buffer tank 20 as depicted in FIGS. 1D.

In the buffer tank 20 is the aqueous acid, alkali, or neutral salt electrolyte and mediated oxidizer species solution in which the oxidized form of the mediator redox couple initially may be present or may be generated electrochemically after introduction of the waste and application of DC power 29 to the electrochemical cell 25. Similarly, the contaminated waste may be introduced into the anolyte reaction chamber 5c when the anolyte is at or below room temperature, operating temperature or some optimum intermediate temperature. DC power supply 29 provides direct current to an electrochemical cell 25. Pump 19 circulates the anolyte portion of the electrolyte and the inorganic waste material is rapidly oxidized at temperatures below 100° C. and at ambient pressure. An in-line filter 6 prevents solid particles large enough to clog the electrochemical cell 25 flow paths from exiting the buffer tank 20. The oxidation process continues to break the materials down into smaller and smaller molecules until the products are at their higher oxidation level. Any residue is pacified in the form of a salt and may be periodically removed through the Inorganic Compound Removal and Treatment System 15 and drain outlets 12. The basic design of the MEO apparatus permits the user to change the type of electrolyte without having to alter the equipment in the apparatus. The changing of the electrolyte is accomplished by using the drain(s) 12 and flush(s) 18 or by opening the buffer tank 20 and catholyte reservoir 31 to introduce the electrolyte(s). The ability to change the type of electrolyte(s) allows the user to tailor the MEO process to differing waste properties. The catholyte reservoir 31 has a screwed top 33 (shown in FIG. 1A), which allow access to the reservoir 31 for cleaning and maintenance by service personnel.

The MEO process advantageous properties, of low power consumption and very low loses of the mediated oxidizer species and electrolyte, provide an option for the device to be operated at a low power level during the day to achieve a slow rate of destruction of the inorganic waste throughout the day. While the MEO apparatus is in this mode, inorganic waste is added as it is generated throughout the day and the unit placed in full activation during off production hours.

The compactness (and scalability) of the device makes it ideal for small and mid-size applications, as well as making it suitable for use with high volume inputs of industrial processes activities. The process operates at low temperature and ambient atmospheric pressure and does not generate toxic compounds during the oxidation of the inorganic waste, making the process indoors compatible. The system is scalable to a unit large enough for a major industrial application. The benign oxidation gas products from the anolyte system A are vented out the vent 14. The off-gas products from the catholyte system B is vented through the atmospheric air vent 47 as shown.

Steps of the Operation of the MEO System Model 5.c

Figure 4:
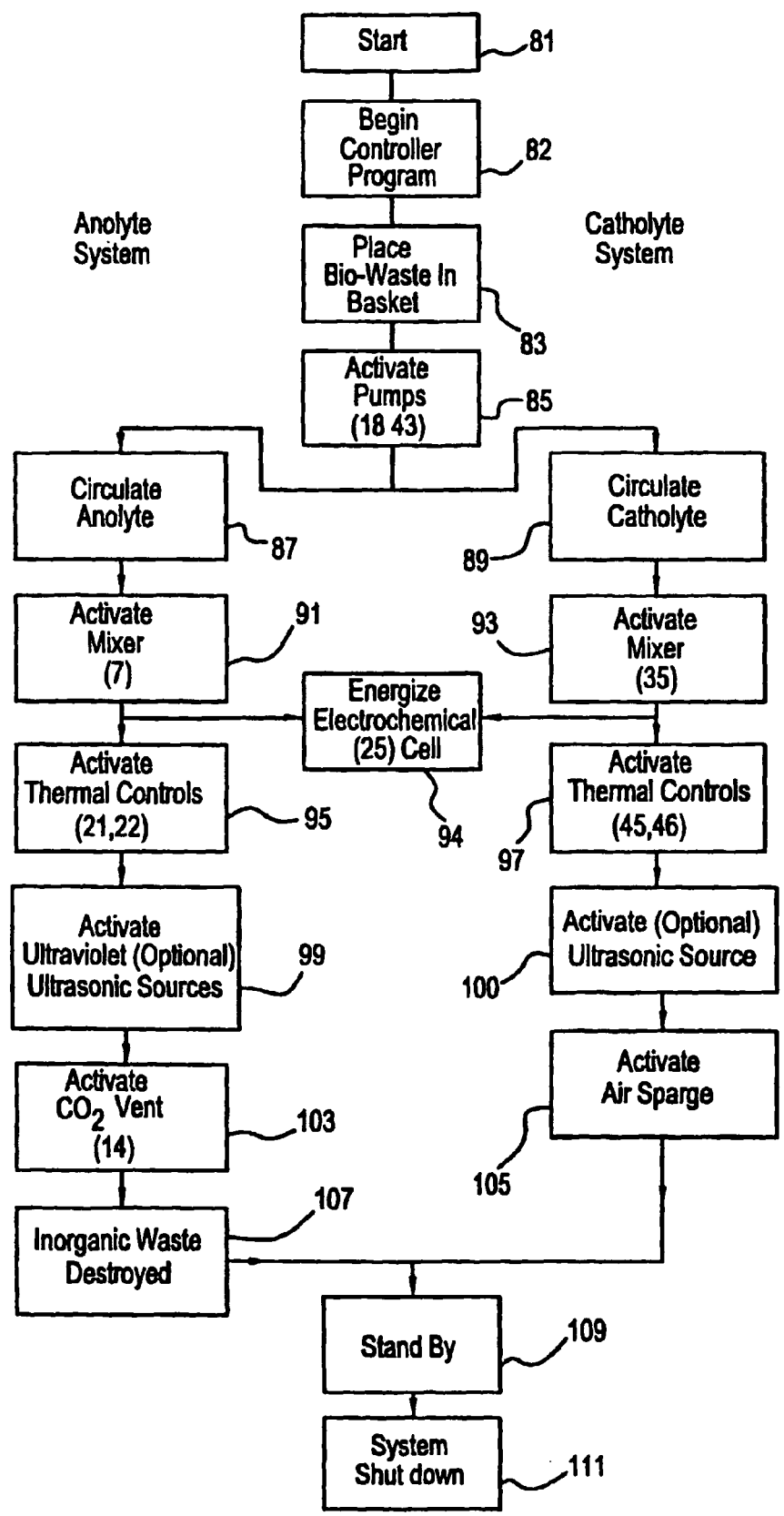
FIG. 4 MEO System Model 5.c Operational Steps is a schematic representation of the generalized steps of the process used in the MEO apparatus (with the understanding that not all of the components shown therein must necessarily be employed in all situations) and others may be added as needed for a particular application.

The steps of the operation of the MEO process are depicted in FIG. 4 MEO System Model 5.c Operational Steps. These operational steps are presented to illustrate the operation of one of the MEO apparatus' from the four configurations previously discussed for oxidizing the various types of inorganic waste. When other anolyte reaction chambers 5(*a,b,d*) configurations are used the series of steps would be similar to the ones for FIG. 1D.

This MEO apparatus is contained in the housing 72. The MEO system is started 81 by the operator engaging the 'ON' button 74 on the control keyboard 53. The system controller 49, which contains a microprocessor, runs the program that controls the entire sequence of operations 82. The monitor screen 51 displays the steps of the process in the proper sequence. The status lights 73 on the panel provide the status of the MEO apparatus (e.g. on, off, ready, standby).

The container contaminated with inorganic waste is connected into the buffer tank 20 as depicted in FIG. 1D.

The pumps 19 and 43 begin circulation 85 of the anolyte 87 and catholyte 89, respectively. As soon as the electrolyte circulation is established throughout the system, the mixers 7 and 35 begin to operate 91 and 93. Depending upon waste characteristics (e.g., reaction kinetics, heat of reaction, etc.) it may be desirable to introduce the waste into a room temperature or cooler anolyte system with little or none of the mediator redox couple in the oxidized form. Once flow is established the thermal controls units 21, 22, 45, and 46 are turned on 95/97, initiating predetermined anodic oxidation and electrolyte heating programs.

The electrochemical cell 25 is energized 94 (by electrochemical cell commands 56) to apply the correct voltage and current as is monitored by the voltmeter 57 and ammeter 55 determined by the controller program. By using programmed electrical power levels and electrolyte temperature it is possible to maintain a predetermined waste destruction rate profile such as a relatively constant reaction rate as the more reactive waste components are oxidized, thus resulting in the remaining waste becoming less and less reactive, thereby requiring more and more vigorous oxidizing conditions.

The ultrasonic sources 9 and 48 and ultraviolet systems 11 are activated 99 and 101 in the buffer tank 20 and catholyte reservoir 31 respectively, if those options are chosen in the controller program.

The vent 14 is activated 103 to release benign inorganic and organic gases from the inorganic waste oxidation process in the anolyte reaction chambers 5*c*. Air sparge 37 draws air 105 into the catholyte reservoir 31, and the air is discharged out the atmospheric vent 47. The progress of the destruction process may be monitored in the controller (oxidation sensor 67) by various cell voltages and currents 55, 57 (e.g., open circuit, anode vs. reference electrode, ion specific electrodes, etc,) as well as monitoring anolyte off-gas (using the sensor 65) composition for $CO_2$, CO and oxygen content.

When the oxidation sensors 65 and 67 determine that the desired degree of waste destruction has been obtained 107, the system goes to standby 109. The system operator executes system shutdown 111 using the controller keyboard 53.

EXAMPLES

The following examples illustrate the application of the process and the apparatus.

Example (1)

Oxidation of Inorganic Compounds

Numerous inorganic products have been oxidized in the MEO System Apparatus.

The MEO process was applied to both gold and platinum foils. The mediator redox couple used in the anolyte was the $Fe^{+3}/FeO_4^{-2}$ couple. A sulfuric based electrolyte was used in both the anolyte and catholyte. The mediator oxidized the gold and platinum and dissolved them into solution in the anolyte.

Example (2)

Efficient and Environmentally Safe Products

The MEO process produces ions in solution, and trace inorganic salts all of which are considered benign for introduction into the environment by regulatory agencies. The halogen ions produced by the dehalogenation of the halogenated inorganics are removed from the anolyte solution by a resin column. The cost of using the MEO process in this invention is competitive with both the incineration and landfill methodologies. The MEO process is uniquely suited for oxidation of inorganic waste because water is actually a source of secondary oxidizing species, rather than parasitic reactions competing for the mediator oxidizing species. Furthermore, the energy that must be provided in the MEO process to heat the waste stream water component from ambient to the electrolyte operating temperature (i.e., 80° C. maximum temperature increase) is trivial compared to the water enthalpy increase required in autoclave or incineration based processes.

Example (3)

Benign In-door Operation

The system is unique relative to earlier art, since it is built to operate in an indoor environment, such as a production or assembly line, where it must be compatible with people working in close proximity to the system. The system is suitable for indoor use in spaces inhabited by personnel as well as for industrial workspaces similar to an incinerator building. Since the process operates at ambient pressure and below 100° C., the MEO process is much safer to operate than competing thermal processes. The critical attribute of a hazardous material is its boiling point since it becomes a gas at that point and much harder to control. A review of the NIOSH hazardous materials list shows that 75% of the materials have boiling points above 100° C. Furthermore, it relatively easy to keep the potential off-gas to at least room temperature (usually 70° C.) where the number of materials drops to 10%.

Example (4)

Inheritantly Safe Operation

The system is built to require limited operating skill. The system controller is programmed to guide the operator through the normal operating cycle as well as the various options available. The system is accessible during its operating cycle so that additional inorganic waste may be added to waste in process, while remaining compatible with the room environment. When new inorganic waste is to be added to the system during operation the operator selects that option. The system controller recycles the system operational steps back to step 83. It deactivates steps 85, 87, 89, 91, 93, 94, 95, 97, 99, 101 and maintains steps 103 and 105 in their active mode. The controller releases the locking latch 76 and the operator adds additional inorganic waste. After he has completed the addition he selects the restart option. The system recycles back through these steps to continue the processing of the waste.

Example (5)

Chemical Reactions are Safe

The system is built to operate with materials that are safe to handle in the environment in which it is to be used. The inorganic waste contains little or no substances that react with our choice of electrolytes to produce volatile compounds that offer a problem in the room environment. The system may operate at temperatures from approximately 0° C. to slightly less than the boiling point of the electrolyte (i.e., usually less then 100° C.) and at ambient atmospheric pressure, which adds to the indoor compatibility.

Example (6)

A Green Machine

The simplicity of the new system built for use with inorganic waste produces a system more economical to operate and cleaner to use than existing waste treatments. The system is truly a 'green machine' in the sense of an environmentally benign system.

Example (7)

System Flexibility

The system is built so that the composition of the electrolyte may be changed to adapt the system to a given composition of the inorganic waste stream. Different compositions of inorganic waste stream can be processed by the same system by either using the same electrolyte or replacing the mediator and electrolyte (either or both the catholyte and anolyte) more suitable for the alternative inorganic waste. The system is configured with ports to flush and drain the anolyte and catholyte separately.

Example (8)

System By-Products are Safe

The system flexibility provides for the introduction of more then one mediator ion resulting in marked improvement in the efficiency of the electrolyte. Furthermore, the wide choice of mediators listed in Table I or available as POMs, and electrolytes in this patent, desensitizes the system to the formation of precipitates in solution (i.e. allows increased ease in preventing formation of unstable oxy compounds).

While the invention has been described with reference to specific embodiments, modifications and variations of the invention may be constructed without departing from the scope of the invention, which is defined in the following characteristics and features.

The invention provides the following new characteristics and features:

1. A process for treating and oxidizing inorganic waste materials comprising disposing an electrolyte in an electrochemical cell, separating the electrolyte into an anolyte portion and a catholyte portion with an ion-selective membrane or semi-permeable membrane applying a direct current voltage between the anolyte portion and the catholyte portion, placing the inorganic waste materials in the anolyte portion, and oxidizing the inorganic waste materials in the anolyte portion with a mediated electrochemical oxidation (MEO) process, wherein the anolyte portion further comprises a mediator in aqueous solution and the electrolyte is an acid, neutral or alkaline aqueous solution.

2. The process of paragraph 1, wherein:
   a. the anolyte portion further comprises one or more simple anions mediator ion species selected from the group described in Table I in the aqueous solution and the electrolyte is an acid, neutral or alkaline solution;
   b. The oxidizing species are selected from one or more Type I isopolyanions (i.e., complex anion redox couple mediators) containing tungsten, molybdenum, vanadium, niobium, tantalum, or combinations thereof as addenda atoms in aqueous solution and the electrolyte is an acid, neutral or alkaline aqueous solution;
   c. The oxidizing species are selected from one or more Type I heteropolyanions formed by incorporation into the aforementioned isopolyanions, as heteroatoms, any of the elements listed in Table II, either singly or in combination thereof in the aqueous solutions and the electrolyte is an acid, neutral, or alkaline aqueous solution;
   d. The oxidizing species are selected from one or more of any heteropolyanions containing at least one heteroatom type (i.e., element) contained in both Table I and Table II in the aqueous solutions and the electrolyte is an acid, neutral, or alkaline aqueous solution;
   e. The oxidizing species are selected from combinations of anion redox couple mediators from any or all of the previous four subparagraphs (2a., 2b., 2c., and 2d.);
   f. introducing catalyst additives to the electrolyte and contributing to kinetics of the mediated electrochemical processes while keeping the additives from becoming directly involved in the oxidizing of the inorganic waste materials;
   g. adding stabilizing compounds to the electrolyte such as tellurate or periodate ions which serve to overcome and stabilize the short lifetime of the oxidized form of the higher oxidation state species of the simple and complex anion redox couple mediators;
   h. the oxidizing species are elements having atomic numbers identified in Table I;
   i. each of the species has normal valence states and higher valence oxidizing states and further comprising creating the higher valence oxidizing states of the oxidizing species by stripping electrons from normal valence state species in the electrochemical cell;
   j. the oxidizing species are "super oxidizers" (SO) (typically exhibit oxidation potentials at least equal to that of the $Ce^{+3}/Ce^{+4}$ redox couple (i.e., 1.7 volts at 1 molar, 25° C. and pH 1)) which are redox couple species that have the capability of producing free radicals such as hydroxyl or perhydroxyl and further comprising creating secondary oxidizers by reacting the SO's with water;
   k. using an alkaline solution for aiding decomposing of the inorganic waste materials derived from the saponification (i.e., base promoted ester hydrolysis) of fatty acids to form water soluble alkali metal salts of the fatty acids (i.e., soaps) and glycerin, a process similar to the production of soap from animal fat by introducing it into a hot aqueous lye solution;

l. using an alkaline anolyte solution that absorbs $CO_2$ forming from oxidation of the inorganic waste sodium bicarbonate/carbonate solution which subsequently circulates through the electrochemical cell, producing a percarbonate oxidizer;

m. super oxidizers generating inorganic free radicals in aqueous solutions from species such as but not limited to carbonate, azide, nitrite, nitrate, phosphite, phosphate, sulfite, sulfate, selenite, thiocyanate, chloride, bromide, iodide, and formate oxidizing species;

n. regenerating the anolyte portion within the electrochemical cell;

o. the membrane (separator between anolyte and catholyte solutions) can be ion-selective or semi-permeable, microporous plastic, sintered glass frit, porous ceramic, etc.;

p. the impression of an AC voltage upon the DC voltage to retard the formation of cell performance limiting surface films on the electrode;

q. disposing a foraminous basket in the anolyte;

r. adding oxygen (this is necessary only for $HNO_3^{31}$ or $NO_3^-$ salts) to the catholyte portion;

s. described in Table I (simple anions); Type I isopolyanions containing tungsten, molybdenum, vanadium, niobium, tantalum, or combinations thereof as addenda atoms; Type I heteropolyanions formed by incorporation into the aforementioned isoopolyanions, as heteroatoms, any of the elements listed in Table II, either singly or in combinations thereof; or any heteropolyanions containing at least one heteroatom type (i.e., element) contained in both Table I and Table II;

t. lower the temperature (e.g. between 0° C. and slightly below the boiling point) of the anolyte before it enters the electrochemical cell to enhance the generation of the oxidized form of the anion redox couple mediator;

u. raise the temperature slightly below the boiling point of the anolyte entering the anolyte reaction chamber to affect the desired chemical reactions at the desired rates following the lowering of the temperature of the anolyte entering the electrochemical cell; and v. the inorganic waste contains elements that are identified in Table I as anion redox couples, they become possible mediated redox couples when the oxidation of the inorganic waste releases them into solution as the reduced form of the redox couple and are raised to the oxidized form when they pass through the electrochemical cell.

3. The process of paragraph 1, wherein:

a. introducing ultraviolet energy into the anolyte portion and decomposing hydrogen peroxide into hydroxyl free radicals therein, thereby increasing efficiency of the MEO process by converting products of electron consuming parasitic reactions (i.e., ozone and hydrogen peroxide) into viable free radical (i.e., secondary) oxidizers without the consumption of additional electrons;

b. using a surfactant to be added to the anolyte promote dispersion of the inorganic waste or intermediate stage reaction products within the aqueous solution when these inorganic waste or reaction products are not water-soluble and tend to form immiscible layers;

c. using simple and/or complex redox couple mediators, and attacking specific inorganic molecules with the oxidizing species;

d. breaking down inorganic waste materials into ions in solution and attacking the inorganic compounds using either the simple and/or complex anion redox couple mediator or inorganic free radicals to generating organic free radicals;

e. raising normal valence state anions to a higher valence state and stripping the normal valence state anions of electrons in the electrochemical cell; (The oxidized forms of any other redox couples present are produced either by similar anodic oxidation or reaction with the oxidized form of other redox couples present. The oxidized species of the redox couples oxidize the inorganic waste molecules and are themselves converted to their reduced form, whereupon they are reoxidized by either of the aforementioned mechanisms and the redox cycle continues);

f. circulating anions through an electrochemical cell to affect the anodic oxidation of the reduced form of the reversible redox couple into the oxidized form;

g. contacting anions with inorganic waste materials in the anolyte portion;

h. circulating anions through the electrochemical cell;

i. involving anions with an oxidation potential above a threshold value of 1.7 volts at 25° C. and pH 1 (i.e., superoxidizer) in a secondary oxidation process and producing oxidizers;

j. adding an ultra-violet (UV) energy source to the anolyte portion and augmenting secondary oxidation processes, breaking down hydrogen peroxide into hydroxyl free radicals, and thus increasing the oxidation processes; and k. The oxidizer species addressed in this patent are described in Table I (simple anions redox couple mediators): Type I IPAs formed by Mo, W, V, Nb, Ta, or mixtures thereof; Type I HPAs formed by incorporation into the aforementioned IPAs of any of the elements listed in Table II (heteroatoms) either singly or in combinations thereof; Or any HPA containing at least one heteroatom type (i.e., element) contained in both Table I and Table II or combinations mediator species from any or all of these generic groups.

4. The process of paragraph 1, further comprising:

a. using oxidizer species that are found in situ in the, waste to be oxidized, by circulating the waste-anolyte mixture through an electrochemical cell where the oxidized form of the in situ reversible redox couple formed by anodic oxidation or alternately reacting with the oxidized form of a more powerful redox couple, if added to the anolyte and anodically oxidized in the electrochemical cell, thereby oxidizing the inorganic waste material;

b. using an alkaline electrolyte, such as but not limited to NaOH or KOH with mediator species wherein the reduced form of said mediator redox couple displays sufficient solubility in said electrolyte to allow the desired oxidation of the inorganic waste to proceed at a practical rate. The oxidation potential of redox reactions producing hydrogen ions (i.e., both mediator species and inorganic waste molecule reactions) are inversely proportional to the electrolyte pH, thus with the proper selection of a mediator redox couple, it is possible, by increasing the electrolyte pH, to minimize the electric potential required to affect the desired oxidation process, thereby reducing the electric power consumed per unit mass of inorganic waste oxidized;

c. the aqueous solution is chosen from acids such as, but not limited to, nitric acid, sulfuric acid, or phosphoric acid, or mixtures thereof; or alkalines such as, but not limited to, sodium hydroxide or potassium hydroxide, or mixtures thereof, or neutral electrolytes such as, but not limited to, sodium or potassium nitrates, sulfates, or phosphates or mixtures thereof; and d. the use of ultrasonic energy to induce microscopic bubble implosion which may be used to affect a desired reduction in sized of the individual second phase waste volumes dispersed in the anolyte.

5. The process of paragraph 1, further comprising:

a. interchanging oxidizing species in a-preferred embodiment without changing equipment; and b. the electrolyte is acid, neutral, or alkaline in aqueous solution.

6. The process of paragraph 1, further comprising:

a. the treating and oxidizing inorganic waste material comprises treating and oxidizing inorganic waste from military ships, such as but not limited to submarines, destroyers, cruisers and carriers;

b. the treating and oxidizing inorganic waste material comprises treating and oxidizing inorganic waste from commercial ships, such as but not limited to cruise ships, tankers, cargo ships, fishing boats, recreational craft or houseboats;

c. separating the anolyte portion and the catholyte portion with a ion-selective or semi-permeable membrane or microporous polymer, ceramic or glass frit membrane;

d. energizing the electrochemical cell at an electrical potential sufficient to form the oxidized form of the redox couple having the highest oxidation potential in the anolyte;

e. introducing inorganic waste materials into the anolyte portion;

f. forming the reduced form of one or more reversible redox couples by contacting with oxidizable molecules, the reaction with which oxidizes the oxidizable material with the concomitant reduction of the oxidized form of the reversible redox couples to their reduced form;

g. an ultrasonic source connected to the anolyte for augmenting secondary oxidation processes by momentarily heating the hydrogen peroxide in the electrolyte to 4800° C. at 1000 atmospheres thereby dissociating the hydrogen peroxide into hydroxyl free radicals thus increasing the oxidation processes;

h. oxidation potentials of redox reactions producing hydrogen ions are inversely related to pH;

i. the process is performed at a temperature from slightly above 0° C. to slightly below the boiling point of the electrolyte usually less than 100° C.;

j. the temperature at which the process is performed is varied;

k. the treating and oxidizing inorganic waste comprises treating and oxidizing solid waste;

l. the treating and oxidizing inorganic waste comprises treating and oxidizing liquid waste;

m. the treating and oxidizing inorganic waste comprises treating and oxidizing gas waste;

n. the treating and oxidizing inorganic waste comprises treating and oxidizing a combination of liquids, solids, and gases; and o. removing and treating precipitates resulting from combinations of oxidizing species and other species released from the inorganic waste during oxidation.

7. The process of paragraph 1, further comprising that it is not necessary for both the anolyte and catholyte solutions to contain the same electrolyte; rather each electrolyte system may be independent of the other, consisting of an aqueous solution of acids, typically but not limited to nitric, sulfuric or phosphoric; alkali, typically but not limited to sodium or potassium hydroxide; or neutral salt, typically but not limited to sodium or potassium salts of the aforementioned acids.

8. The process of paragraph 1, further comprising the operating of the electrochemical cell at a current density greater than 0.5 amp per square centimeter across the membrane, even though this is the limit over which there is the possibility that metallic anions may leak through the membrane in small quantities, and recovering the metallic anions through a devise such as a resin column thus allowing a greater rate of destruction of materials in the anolyte chamber.

9. The process of paragraph 1, wherein:

a. the catholyte solution further comprises an aqueous solution and the electrolyte in the solution is composed of acids, typically but not limited to nitric, sulfuric or phosphoric; or alkali, typically but not limited to sodium or potassium hydroxide; or neutral salt, typically but not limited to sodium or potassium salts of the aforementioned strong acids;

b. adding oxygen (this is necessary only for $HNO_3^-$ or $NO_3^-$ salts) to the catholyte portion;

c. concentration of electrolyte in the catholyte is governed by its effect upon the conductivity of the catholyte solution desired in the electrochemical cell;

d. ultrasonic energy induced microscopic bubble implosion is used to affect vigorous mixing in the catholyte solution where it is desirable to oxidize nitric acid and the small amounts of nitrogen oxides when nitric acid is used in the catholyte electrolyte;

e. mechanical mixing is used to affect vigorous mixing in the catholyte solution where it is desirable to oxidize nitric acid and the small amounts of nitrogen oxides;

f. air is introduced into the catholyte solution to promote oxidation of nitric acid and the small amounts of nitrogen oxides when nitric acid is used in the catholyte electrolyte;

g. air is introduced into the catholyte solution to dilute any hydrogen produced in the catholyte solution before being released; and h. hydrogen gas evolving from the cathode is fed to an apparatus that uses hydrogen as a fuel such as a proton exchange membrane (PEM) fuel cell.

10. An apparatus for treating and oxidizing inorganic waste materials comprising an electrochemical cell, an electrolyte disposed in the electrochemical cell, an ion-selective or semi-permeable membrane, disposed in the electrochemical cell for separating the cell into anolyte and catholyte chambers and separating the electrolyte into anolyte and catholyte portions, electrodes further comprising an anode and a cathode disposed in the electrochemical cell respectively in the anolyte and catholyte chambers and in the anolyte and catholyte portions of the electrolyte, a power supply connected to the anode and the cathode for applying a direct current voltage between the anolyte and the catholyte portions of the electrolyte, and oxidizing of the inorganic waste materials in the anolyte portion with a mediated electrochemical oxidation (MEO) process wherein the anolyte portion further comprises a mediator in aqueous solution and the electrolyte is an acid, neutral or alkaline aqueous solution.

11. The apparatus of paragraph 10, wherein:

a. adding stabilizing compounds to the anolyte such as tellurate or periodate ions which serve to overcome and stabilize the short lifetime of the oxidized form of the higher oxidation state species of the simple and complex anion redox couple mediators;

b. the oxidizer species addressed in this patent are described in Table I (simple anions redox couple mediators);
c. the oxidizer species addressed in this patent are described in Table I (simple anions redox couple mediators): Type I IPAs formed by Mo, W, V, Nb, Ta, or mixtures thereof; Type I HPAS formed by incorporation into the aforementioned IPAs if any of the elements listed in Table II (heteroatoms) either singly or in combinations thereof; Or any HPA containing at least one heteroatom type (i.e., element) contained in both Table I and Table II;
d. the oxidizer species addressed in this patent are combination mediator species from any or all of these generic groups;
e. the oxidizing species are super oxidizers and further comprising creating secondary oxidizers by reacting the super oxidizers with the aqueous anolyte;
f. an alkaline solution for aiding in the decomposing of the inorganic waste materials;
g. an alkaline solution for absorbing $CO_2$ and forming alkali metal bicarbonate/carbonate for circulating through the electrochemical cell for producing a percarbonate oxidizer;
h. using oxidizing species from the MEO process inorganic free radicals may be generated in aqueous solutions derived from carbonate, azide, nitrite, nitrate, phosphite, phosphate, sulfite, sulfate, selenite, thiocyanate, chloride, bromide, iodide, and species;
i. inorganic free radicals for aiding the MEO process and breaking down the inorganic waste materials into simpler (i.e., smaller molecular structure) inorganic compounds;
j. anions with an oxidation potential above a threshold value of 1.7 volts at 25° C. and pH 1 (i.e., superoxidizer) for involving in a secondary oxidation process for producing oxidizers;
k. the use of ultrasonic energy induces microscopic bubble implosion which is used to affect a desired reduction in size of the individual second phase waste volumes dispersed in the anolyte;
l. membrane can be ion-selective or semi-permeable, microporous polymer, porous ceramic or glass frit;
m. with the possible impression of an AC voltage upon the DC voltage to retard the formation of cell performance limiting surface films on the electrode; and
n. external air is introduced through an air sparge into the catholyte reservoir where oxygen contained in the air oxidizes nitrogen compounds produced by the cathode reactions (this is necessary only when nitrogen compounds can occur in the catholyte).

12. The apparatus of paragraph 10, wherein:
a. each of the oxidizing species has normal valence states (i.e., reduced form of redox couple) and higher valence oxidizing states and further comprising creating the higher valence oxidizing states (i.e., oxidized form of redox couple) of the oxidizing species by stripping and reducing electrons off normal valence state species in the electrochemical cell;
b. using species that are usable in alkaline solutions since oxidation potentials of redox reactions producing hydrogen ions are inversely related to pH which reduces the electrical power required to oxidize the inorganic waste;
c. further oxidizing species, and attacking specific inorganic molecules with the oxidizing species;
d. energizing the electrochemical cell at a potential level sufficient to form the oxidized form of the redox couple having the highest oxidation potential in the anolyte;
e. adjusting the temperature (e.g. between 0° C. and slightly below the boiling point) of the anolyte with the heat exchanger before it enters the electrochemical cell to enhance the generation of the oxidized form of the anion redox couple mediator; and
f. adjusting the temperature of the anolyte (e.g., between 0° C. and slightly below the boiling point) entering the anolyte reaction chamber with the heat exchanger to affect the desired chemical reactions at the desired rates following the lowering of the temperature of the anolyte entering the electrochemical cell.

13. The apparatus of paragraph 10, wherein:
a. the oxidizing species are one or more Type I isopolyanions (i.e., complex anion redox couple mediators) containing tungsten, molybdenum, vanadium, niobium, tantalum, or combinations thereof as addenda atoms in aqueous solution and the electrolyte is an acid, neutral or alkaline aqueous solution;
b. the oxidizing species are one or more Type I heteropolyanions formed by incorporation into the aforementioned isopolyanions, as heteroatoms, any of the elements listed in Table II, either singly or in combination thereof in the aqueous solutions and the electrolyte is an acid, neutral, or alkaline aqueous solution;
c. the oxidizing species are one or more of any heteropolyanions containing at least one heteroatom type (i.e., element) contained in both Table I and Table II in the aqueous solutions and the electrolyte is an acid, neutral, or alkaline aqueous solution;
d. the oxidizing species are combinations of anion redox couple mediators from any or all of the previous three subparagraphs (13a., 13b., 13c);
e. the oxidizing species are higher valence state of species found in situ for oxidizing the inorganic waste material; and
f. the electrolyte is an acid, neutral, or alkaline aqueous solution.

14. The apparatus of paragraph 10, further comprising:
a. the aqueous solution is chosen from acids such as, but not limited to, nitric acid, sulfuric acid, or phosphoric acid; alkalines such as but not limited to of sodium hydroxide or potassium hydroxide; or neutral electrolytes such as, but not limited to, sodium or potassium nitrates, sulfates, or phosphates;
b. the inorganic waste material is pharmaceutical manufacturing process waste abatement, and obsolete pharmaceuticals;
c. the inorganic waste material is waste from military ships, such as but not limited to submarines, destroyers, cruisers and carriers;
d. the inorganic waste material is waste from non-military ship such as but not limited to commercial ships, cruise ships, tankers, cargo ships, fishing boats, recreational craft or houseboats;
e. free hydroxyl radical for replacing hydrogen peroxide and ozone in chemical sterilization;
f. an ion-selective or semi-permeable, microporous polymer, porous ceramic or sintered glass frit membrane for separating the anolyte portion and the catholyte portion while allowing hydrogen or hydronium ion passage from the anolyte to the catholyte;
g. oxidation potentials of redox reactions producing hydrogen ions are inversely related to pH;
h. the inorganic waste is liquid waste;

i. the inorganic waste is solid waste;
j. the inorganic waste is gas waste;
k. the inorganic waste is a combination of liquids, solids, gases and non-inorganic waste; and
l. oxidizing species may be interchanged in a preferred embodiment without changing equipment.

15. The apparatus of paragraph 10, further comprising:
a. anolyte reaction chamber(s) 5(*b,c*) and buffer tank 20 housing the bulk of the anolyte portion and the foraminous basket 3;
b. anolyte reaction chamber 5*a* housing the bulk of the anolyte portion;
c. an anolyte reaction chamber 5*d* and buffer tank 20 housing the bulk of the anolyte portion;
d. an input pump 10 is attached to the buffer tank 20 to enter liquid inorganic waste into the buffer tank 20;
e. a spray head 4(*a*) and a stream head 4(*b*) attached to the tubing coming from the electrochemical cell 25 that inputs the anolyte containing the oxidizer into the anolyte reaction chamber(s) 5(*a,b,c*) and buffer tank 20 in such a manner as to promote mixing of the incoming anolyte with the anolyte already in the anolyte reaction chambers(s) 5(*a,b,c*);
f. an anolyte reaction chamber(s) 5(*b,c*) houses a foraminous basket 3 with a top that holds solid forms of the inorganic waste in the electrolyte;
g. a hinged lid 1 attached to the reaction chamber(s) 5(*a,b,c*) allowing insertion of waste into the anolyte portion as liquid, solid, or a mixture of liquids and solids;
h. the lid 1 contains a locking latch 76 to secure the reaction chamber(s) 5(*a,b,c*) during operation;
i. a suction pump 8 is attached to buffer tank 20 to pump anolyte to the anolyte reaction chamber(s) 5(*c,d*);
j. an input pump 10 is attached to buffer tank 20 to pump anolyte from the anolyte reaction chamber(s) 5(*c,d*) back to the buffer tank 20; and
k. an air pump 32 is attached to buffer tank 20 to pump off gases from the anolyte reaction chamber(s) 5(*c,d*) back to the buffer tank 20 for further oxidation.

16. The apparatus of paragraph 10, further comprising:
a. an ultraviolet source 11 connected to the anolyte reaction chamber(s) 5(*a,b,c*) and buffer tank 20 for decomposing hydrogen peroxide and ozone into hydroxyl free radicals therein and increasing efficiency of the MEO process by recovering energy through the oxidation of the inorganic waste materials in the anolyte chamber by these secondary oxidizers;
b. an ultrasonic source 9 connected to the anolyte reaction chamber(s) 5(*a,b,c*) and buffer tank 20 for augmenting secondary oxidation processes by heating the hydrogen peroxide containing electrolyte to produce extremely short lived and localized conditions of 4800° C. and 1000 atmospheres pressure within the anolyte to dissociate hydrogen peroxide into hydroxyl free radicals thus increasing the oxidation processes;
c. an ultrasonic energy 9 source connected into the anolyte reaction chamber(s) 5(*a,b,c*) and buffer tank 20 for irradiating cell membranes in any biological waste material or combined waste by momentarily raising temperature within the cell membranes and causing cell membrane fail and rupture thus creating greater exposure of cell contents to oxidizing species in the anolyte;
d. the use of ultrasonic energy for mixing material in the anolyte, via the ultrasonic energy source 9, to induce microscopic bubble implosion which is used to affect a desired reduction in sized of the individual second phase waste volumes and dispersal throughout the anolyte;
e. a mixer 35 for stirring the anolyte connected to the anolyte reaction chamber(s) 5(*a,b,c*) and the buffer tank 20;
f. a $CO_2$ vent 14 for releasing $CO_2$ atmospherically;
g. an external $CO_2$ vent 14 connected to the housing for releasing $CO_2$ into the atmosphere;
h. a penetrator 34 attached to the basket 3 to puncture the solids thus increasing the surface area exposed to the oxidizer;
i. an inorganic compounds removal and treatment system 15 connected to the anolyte pump is used should there be more than trace amount of chlorine, or other precipitates forming anions present in the inorganic waste being processed, thereby precluding formation of unstable oxycompounds (e.g., perchlorates, etc.);
j. an off-gas cleaning system 16 comprises scrubber/absorption columns;
k. a condenser 13 connected to the anolyte-reaction chamber(s) 5(*a,b,c*) and buffer tank 20;
l. non-condensable incomplete oxidation products (e.g., low molecular weight organics, carbon monoxide, etc.) are reduced to acceptable levels for atmospheric release by a gas cleaning system 16;
m. gas-cleaning system 16 is not a necessary component of the MEO apparatus for the oxidation of most types of inorganic waste;
n. if the gas cleaning system 16 is incorporated into the MEO apparatus, the anolyte off-gas is contacted in a gas cleaning system 16 wherein the noncondensibles from the condenser 13 are introduced into the lower portion of the gas cleaning system 16 through a flow distribution system and a small side stream of freshly oxidized anolyte direct from the electrochemical cell 25 is introduced into the upper portion of the column, this results in the gas phase continuously reacting with the oxidizing mediator species as it rises up the column past the down flowing anolyte;
o. external drain 12, for draining to the organic compound removal system 17 and the inorganic compounds removal and treatment system 15, and for draining the anolyte system;
p. organic compounds recovery system 17 is used to recover a) organic materials that are benign and do not need further treatment; and b) organic materials (such as biphenyls) in combined waste that may be used in the form they have been reduced and thus would be recovered for that purpose;
q. optional inorganic compound removal and treatment system 15 is used should there be more than trace amount of precipitate forming ions present in the inorganic waste being processed, thereby precluding formation of unstable oxycompounds (e.g., perchlorates, etc.);
r. small thermal control units 21 and 22 are connected to the flow stream to heat or cool the anolyte to the selected temperature range;
s. anolyte is circulated into the reaction chambers 5(*a,b,c,d*) through the electrochemical cell 25 by pump 19 on the anode 26 side of the membrane 27;
t. a flush(s) 18 for flushing the anolyte and catholyte system;
u. filter 6 is located at the base of the reaction chambers 5(*a,b,c,d*) and buffer tank 20 to limit the size of the solid particles to approximately 1 mm in diameter;
v. membrane 27 in the electrochemical cell 25 separates the anolyte portion and catholyte portion of the electrolyte;
w. electrochemical cell 25 is energized by a DC power supply 29, which is powered by the AC power supply 30;

x. DC power supply 29 is low voltage high current supply usually operating below 4V DC but not limited to that range;
y. AC power supply 29 operates off a typical 110 v AC line for the smaller units and 240 v AC for the larger units;
z. electrolyte containment boundary is composed of materials resistant to the oxidizing electrolyte (e.g., stainless steel, PTFE, PTFE lined tubing, glass, etc.); and
aa. an electrochemical cell 25 connected to the anolyte reaction chamber(s) 5(*a,b,c*) and buffer tank 20.

17. The apparatus of paragraph 10, wherein:
a. in the chambers 5(*a,b,c*) and buffer tank 20 is the aqueous acid, alkali, or neutral salt electrolyte and mediated oxidizer species solution in which the oxidizer form of the mediator redox couple initially may be present or may be generated electrochemically after introduction of the waste and application of DC power 30 to the electrochemical cell 25;
b. waste is introduced when the anolyte is at room temperature, operating temperature or some optimum intermediate temperature;
c. DC power supply 30 provides direct current to an electrochemical cell 25;
d. pump 19 circulates the anolyte portion of the electrolyte and the inorganic waste material is rapidly oxidized at temperatures below 100° C. and ambient pressure;
e. in-line filter 6 prevents solid particles large enough to clog the electrochemical cell 25 flow paths from exiting the reaction chambers 5(*a,b,c,d*) and buffer tank 20;
f. residue is pacified in the form of a salt and may be periodically removed through the Inorganic Compound Removal and Treatment System 15 and drain outlets 12;
g. electrolyte may be changed through this same plumbing for introduction into the reaction chambers 5 and 31;
h. catholyte reservoir 31 has a screwed top 33 (shown in FIG. 1), which allows access to the reservoir 31 for cleaning and maintenance by service personnel;
i. the system is scalable to a large unit for a large industrial application;
j. the process operates at low temperature and ambient atmospheric pressure and does not generate toxic compounds during the destruction of the inorganic waste, making the process indoors compatible;
k. the system is scalable to a large unit for a large industrial application; and
l. gas oxidation product from the anolyte system A is vented out the vent 14.

18. The apparatus of paragraph 10, wherein:
a. an anolyte recovery system 41 is connected to the catholyte pump (43);
b. a thermal control unit 45 is connected to the catholyte reservoir for varying the temperature of the catholyte portion;
c. a catholyte reservoir 31 is connected to the cathode portion of the electrochemical cell;
d. bulk of the catholyte is resident in the catholyte reservoir 31;
e. catholyte portion of the electrolyte flows into a catholyte reservoir 31;
f. an air sparge 37 is connected to the catholyte reservoir 31 for introducing air into the catholyte reservoir 31;
g. an anolyte recovery system 41 for capturing the anions and for reintroducing the anions into the anolyte chamber or disposal from the catholyte electrolyte;
h. an off-gas cleaning system 39 for cleaning gases before release into the atmosphere connected to the catholyte reservoir;
i. an atmospheric vent 47 for releasing gases into the atmosphere connected to the off-gas cleaning system;
j. cleaned gas from the off-gas cleaning system 39 is combined with unreacted components of the air introduced into the system and discharged through the atmospheric vent 47;
k. a catholyte reservoir 31 has a screwed top 33 (shown in FIG. 1A), which allows access to the reservoir 31 for cleaning and maintenance by service personnel;
l. a mixer 35 for stirring the catholyte connected to the catholyte reservoir;
m. a catholyte pump 43 for circulating catholyte back to the electrochemical cell connected to the catholyte reservoir;
n. a drain 12 for draining catholyte;
o. a flush 18 for flushing the catholyte system;
p. an air sparge 37 connected to the housing for introducing air into the catholyte reservoir 31;
q. catholyte portion of the electrolyte is circulated by pump 43 through the electrochemical cell 25 on the cathode 28 side of the membrane 27;
r. small thermal control units 45 and 46 are connected to the catholyte flow stream to heat or cool the catholyte to the selected temperature range;
s. contact of the oxidizing gas with the catholyte electrolyte may be enhanced by using conventional techniques for promoting gas/liquid contact by ultrasonic vibration 48, mechanical mixing 35, etc.;
t. operating the electrochemical cell 25 at higher than normal membrane 27 current densities (i.e., above about 0.5 amps/cm$^2$) increases the rate of waste destruction, but also results in increased mediator ion transport through the membrane into the catholyte;
u. optional anolyte recovery system 41 is positioned on the catholyte side;
v. systems using non-nitric acid catholytes may also require air sparging to dilute and remove off-gas such as hydrogen;
w. some mediator oxidizer ions may cross the membrane 27 and this option is available if it is necessary to remove them through the anolyte recovery system 41 to maintain process efficiency or cell operability, or their economic worth necessitates their recovery;
x. using the anolyte recovery system 41 the capital cost of expanding the size of the electrochemical cell 25 can be avoided; and
y. operating the electrochemical cell 25 at higher than normal membrane current density (i.e., above about 0.5 amps per centimeter squared) improves economic efficiency.

19. The apparatus of paragraph 10, wherein:
a. operator runs the MEO Apparatus FIG. 1A and FIG. 1B by using the MEO Controller depicted in FIG. 3 MEO System Model 5.f Controller;
b. controller 49 with microprocessor is connected to a monitor 51 and a keyboard 53;
c. operator inputs commands to the controller 49 through the keyboard 53 responding to the information displayed on the monitor 51;
d. controller 49 runs a program that sequences the steps for the operation of the MEO apparatus;
e. program has pre-programmed sequences of standard operations that the operator may follow or choose his own sequences of operations;
f. controller 49 allows the operator to select his own sequences within limits that assure a safe and reliable operation;

g. controller 49 sends digital commands that regulates the electrical power (AC 30 and DC 29) to the various components in the MEO apparatus: pumps 19 and 43, mixers 7 and 35, thermal controls 21, 22, 45, 46, heat exchangers 23 and 24, ultraviolet sources 11, ultrasonic sources 9 and 48, $CO_2$ vent 14, air sparge 37, and electrochemical cell 25;

h. controller receives component response and status from the components;

i. controller sends digital commands to the sensors to access sensor information through sensor responses;

j. sensors in the MEO apparatus provide digital information on the state of the various components;

k. sensors measure flow rate 59, temperature 61, pH 63, $CO_2$ venting 65, degree of oxidation 67, air sparge sensor 69, etc; and l. controller 49 receives status information on the electrical potential (voltmeter 57) across the electrochemical cell or individual cells if a multi-cell configuration and between the anode(s) and reference electrodes internal to the cell(s) 25 and the current (ammeter 55) flowing between the electrodes within each cell.

Figure 2:
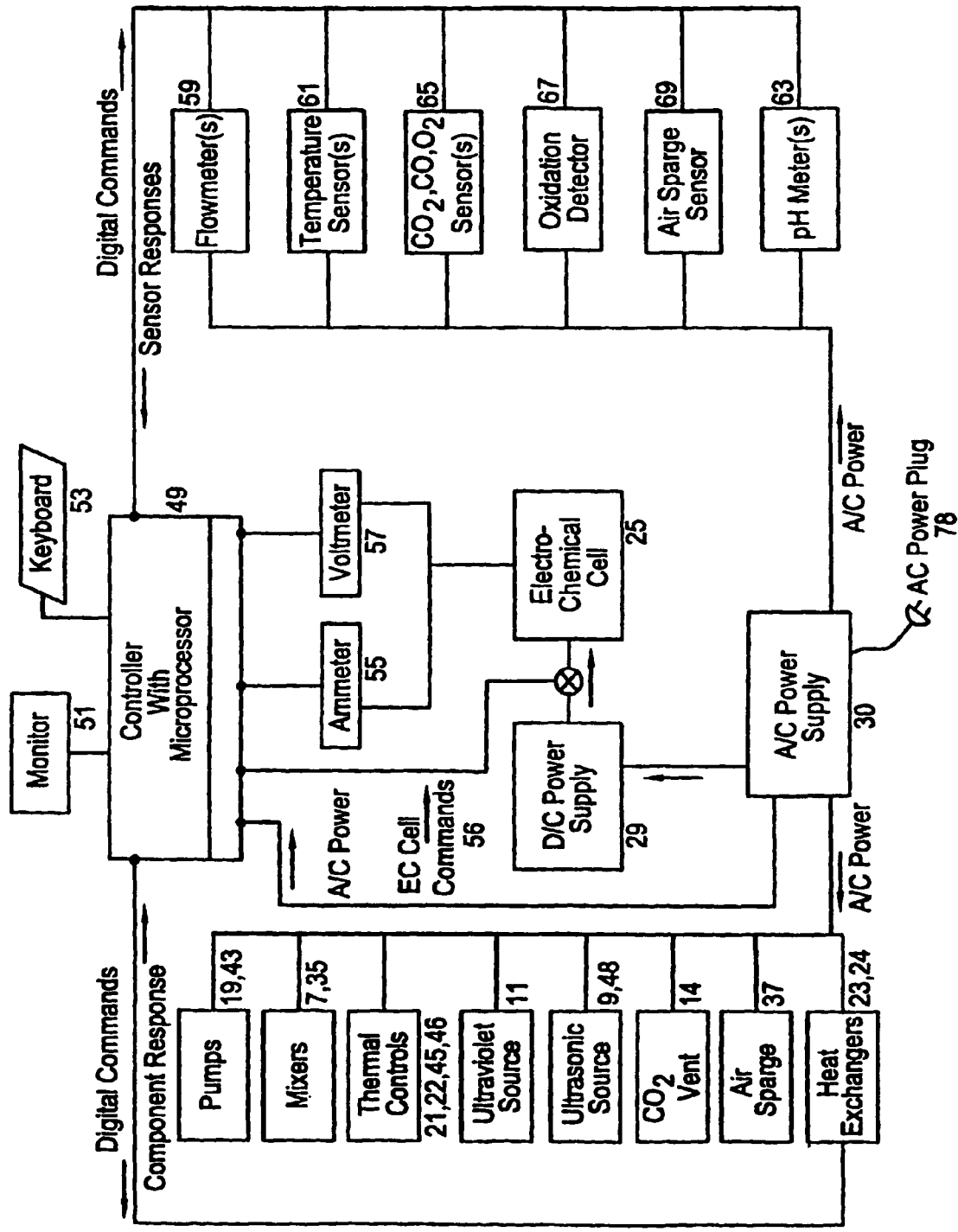
FIG. 2 MEO System Model 5.c is a schematic representation of a preferred embodiment using the FIG. 1D configuration. The Model 5.c uses the buffer tank 20 in the MEO apparatus depicted in FIG. 1A. This model is used for inorganic solids, and mixtures which include small particulate.

20. The apparatus of paragraph 10, wherein:

a. preferred embodiment, MEO System Model 5.c is sized for use for a small to mid-size application for the oxidation of inorganic waste associated with an industrial process such as metallurgical cleaning system. This embodiment depicts a configuration using the system apparatus presented in FIGS. 1A and 1C. Other preferred embodiments (representing FIGS. 1B, 1D, and 1E) have differences in the external configuration and size but are essentially the same in internal function and components as depicted in FIGS. 1A and 1B;

b. preferred embodiment in FIG. 2 comprises a housing 72 constructed of metal or high strength plastic surrounding the electrochemical cell 25, the electrolyte and the foraminous basket 3;

c. AC power is provided to the AC power supply 30 by the power cord 78;

d. monitor screen 51 is incorporated into the housing 72 for displaying information about the system and about the waste being treated;

e. control keyboard 53 is incorporated into the housing 72 for inputting information into the system;

f. monitor screen 51 and the control keyboard 53 may be attached to the system without incorporating them into the housing 72;

g. system model 5.c has a control keyboard 53 for input of commands and data;

h. monitor screen 51 to display the systems operation and functions;

i. status lights 73 for on, off and standby, are located below the keyboard 53 and monitor screen 51;

j. in a preferred embodiment, status lights 73 are incorporated into the housing 72 for displaying information about the status of the treatment of the inorganic waste material;

k. air sparge 37 is incorporated into the housing 72 to allow air to be introduced into the catholyte reservoir 31 below the surface of the catholyte;

l. a $CO_2$ vent 14 is incorporated into the housing 72 to allow for $CO_2$ release from the anolyte reaction chamber housed within;

m. in a preferred embodiment, the housing includes means for cleaning out the MEO waste treatment system, including a flush(s) 18 and drain(s) 12 through which the anolyte and catholyte pass;

n. the preferred embodiment further comprises an atmospheric vent 47 facilitating the release of gases into the atmosphere from the catholyte reservoir 31;

o. hinged lid 1 is opened and the inorganic waste is deposited in the basket 3 in the anolyte reaction chamber 5*b*;

p. lid stop 2 keeps lid opening controlled; and q. hinged lid 1 is equipped with a locking latch 76 that is operated by the controller 49.

21. The apparatus of paragraph 10, wherein:

a. MEO apparatus is contained in the housing 72;

b. MEO system is started 81 by the operator engaging the 'ON' button (status buttons 73) on the control keyboard 53;

c. system controller 49, which contains a microprocessor, runs the program that controls the entire sequence of operations 82;

d. monitor screen 51 displays the steps of the process in the proper sequence;

e. status lights 73 on the panel provide the status of the MEO apparatus (e.g. on, off, ready, standby);

f. lid 1 is opened and the inorganic waste is placed 83 in the basket 3 as a liquid, solid, or a mixture of liquids and solids, whereupon the solid portion of the waste is retained and the liquid portion flows through the basket 3 and into the anolyte;

g. locking latch 76 is activated after waste is placed in basket;

h. pumps 19 and 43 are activated which begins circulation 85 of the anolyte 87 and catholyte 89, respectively;

i. once the electrolyte circulation is established throughout the system, the mixers 7 and 35 begin to operate 91 and 93;

j. depending upon waste characteristics (e.g., reaction kinetics, heat of reaction, etc.) it may be desirable to introduce the waste into a room temperature or cooler system with little or none of the mediator redox couple in the oxidizer form;

k. once flow is established the thermal control units 21, 22, 45, and 46 are turned on 95/97, initiating predetermined anodic oxidation and electrolyte heating programs;

l. the electrochemical cell 25 is energized 94 (by cell commands 56) to the electric potential 57 and current 55 density determined by the controller program;

m. by using programmed electrical power and electrolyte temperature ramps it is possible to maintain a predetermined waste destruction rate profile such as a relatively constant reaction rate as the more reactive waste components are oxidized, thus resulting in the remaining waste becoming less and less reactive, thereby requiring more and more vigorous oxidizing conditions;

n. the ultrasonic 9 and 48 and ultraviolet systems 11 are activated 99 and 101 in the anolyte reaction chambers 5(*a,b,c*) and catholyte reservoir 31 if those options are chosen in the controller program;

o. vent 14 is activated 103 to release gases from the inorganic waste oxidation process in the anolyte reaction chambers 5(*a,b,c,d*) and buffer tank 20;

p. air sparge 37 and atmospheric vent 47 are activated 105 in the catholyte system;

q. progress of the destruction process is monitored in the controller (oxidation sensor 67) by various cell voltages and currents 55, 57 (e.g., open circuit, anode vs. reference electrode, ion specific electrodes, etc,) as well as monitoring $CO_2$, CO, and $O_2$ gas 65 composition for $CO_2$, CO and oxygen content;

r. halogenated inorganic waste is being oxidized into ions in solution;

s. air sparge 37 draws air 105 into the catholyte reservoir 31, and excess air is discharged out the atmospheric vent 47;
t. when the oxidation sensor 67 determines the desired degree of waste destruction that has been obtained 107, the system goes to standby 109;
u. MEO apparatus as an option may be placed in a standby mode with inorganic waste being added as it is generated throughout the day and the unit placed in full activation during non-business hours; and
v. system operator executes system shutdown 111 using the controller keyboard 53.

TABLE I

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| I | A | None | | | |
| | B | Copper (Cu) | +2 | $Cu^{-2}$ (cupric) | +2 Species/+3, +4 Species |
| | | | | $HCuO_2^-$ (bicuprite) | +3 Species/+4 Species |
| | | | | $CuO_2^{-2}$ (cuprite) | |
| | | | +3 | $Cu^{+3}$ | |
| | | | | $CuO_2^-$ (cuprate) | |
| | | | | $Cu_2O_3$ (sesquioxide) | |
| | | | +4 | $CuO_2$ (peroxide) | |
| | | Silver (Ag) | +1 | $Ag^1$ (argentous) | +1 Species/+2, +3 Species |
| | | | | $AgO^-$ (argentite) | +2 Species/+3 Species |
| | | | +2 | $Ag^{-2}$ (argentic) | |
| | | | | $AgO$ (argentic oxide) | |
| | | | +3 | $AgO^1$ (argentyl) | |
| | | | | $Ag_2O_3$ (sesquioxide) | |
| | | Gold (Au) | +1 | $Au^1$ (aurous) | +1 Species/+3, +4 Species |
| | | | +3 | $Au^{+3}$ (auric) | +3 Species/+4 Species |
| | | | | $AuO^-$ (auryl) | |
| | | | | $H_3AuO_3^-$ (auric acid) | |
| | | | | $H_2AuO_3^-$ (monoauarate) | |
| | | | | $HAuO_3^{-2}$ (diaurate) | |
| | | | | $AuO_3^{-3}$ (triaurate) | |
| | | | | $Au_2O_3$ (auric oxide) | |
| | | | | $Au(OH)_3$ (auric hydroxide) | |
| | | | +4 | $AuO_2$ (peroxide) | |
| II | A | Magnesium (Mg) | +2 | $Mg^{+2}$ (magnesic) | +2 Species/+4 Species |
| | | | +4 | $MgO_2$ (peroxide) | |
| | | Calcium (Ca) | +2 | $Ca^{+2}$ | +2 Species/+4 Species |
| | | | +4 | $CaO_2$ (peroxide) | |
| | | Strontium | +2 | $Sr^{+2}$ | +2 Species/+4 Species |
| | | | +4 | $SrO_2$ (peroxide) | |
| | | Barium (Ba) | +2 | $Ba^{+2}$ | +2 Species/+4 Species |
| | | | +4 | $BaO_2$ (peroxide) | |
| II | B | Zinc (Zn) | +2 | $Zn^{+2}$ (zincic) | +2 Species/+4 Species |
| | | | | $ZnOH^1$ (zincyl) | |
| | | | | $HZnO_2^-$ (bizincate) | |
| | | | | $ZnO_2^{-2}$ (zincate) | |
| | | | +4 | $ZnO_2$ (peroxide) | |
| | | Mercury (Hg) | +2 | $Hg^{+2}$ (mercuric) | +2 Species/+4 Species |
| | | | | $Hg(OH)_2$ (mercuric hydroxide) | |
| | | | | $HHgO_2^-$ (mercurate) | |
| | | | +4 | $HgO_2$ (peroxide) | |
| III | A | Boron | +3 | $H_3BO_3$ (orthoboric acid) | +3 Species/+4.5, +5 Species |
| | | | | $H_2BO_3^-$, $HBO_3^{-2}$, $BO_3^{-3}$ (orthoborates) | |
| | | | | $BO_2^-$ (metaborate) | |
| | | | | $H_2B_4O_7$ (tetraboric acid) | |
| | | | | $HB_4O_7^-/B_4O_7^{-2}$ (tetraborates) | |
| | | | | $B_2O_4^{-2}$ (diborate) | |
| | | | | $B_6O_{10}^{-2}$ (hexaborate) | |
| | | | +4.5 | $B_2O_5^-$ (diborate) | |
| | | | +5 | $BO_3^-/BO_2^- \cdot H_2O$ (perborate) | |
| | | Thallium (Tl) | +1 | $Tl^{+1}$ (thallous) | +1 Species/+3 or +3.33 Species |
| | | | +3 | $Tl^{+3}$ (thallic) | +3 Species/+3.33 Species |
| | | | | $TlO^+$, $TlOH^{+2}$, $Tl(OH)_2^+$ (thallyl) | |
| | | | | $Tl_2O_3$ (sesquioxide) | |
| | | | | $Tl(OH)_3$ (hydroxide) | |
| | | | +3.33 | $Tl_3O_5$ (peroxide) | |
| | B | | | See Rare Earths and Actinides | |
| IV | A | Carbon (C) | +4 | $H_2CO_3$ (carbonic acid) | +4 Species/+5, +6 Species |
| | | | | $HCO_3^-$ (bicarbonate) | |
| | | | | $CO_3^{-2}$ (carbonate) | |
| | | | +5 | $H_2C_2O_6$ (perdicarbonic acid) | |
| | | | +6 | $H_2CO_4$ (permonocarbonic acid) | |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | Germanium (Ge) | +4 | $H_2GeO_3$ (germanic acid)<br>$HGeO_3^-$ (bigermaniate)<br>$GeO_3^{-4}$ (germinate)<br>$Ge^{+4}$ (germanic)<br>$GeO_4^{-4}$<br>$H_2Ge_2O_5$ (digermanic acid)<br>$H_2Ge_4O_9$ (tetragermanic acid)<br>$H_2Ge_5O_{11}$ (pentagermanic acid)<br>$HGe_5O_{11}^-$ (bipentagermanate) | +4 Species/+6 Species |
| | | | +6 | $Ge_5O_{11}^{-2}$ (pentagermanate) | |
| | | Tin (Sn) | +4 | $Sn^{-4}$ (stannic)<br>$HSnO_3^-$ (bistannate)<br>$SnO_3^{-2}$ (stannate)<br>$SnO_2$ (stannic oxide)<br>$Sn(OH)_4$ (stannic hydroxide) | +4 Species/+7 Species |
| | | | +7 | $SnO_4^-$ (perstannate) | |
| | | Lead (Pb) | +2 | $Pb^{+2}$ (plumbous)<br>$HPbO_2^-$ (biplumbite)<br>$PbOH^+$<br>$PbO_2^{-2}$ (plumbite)<br>$PbO$ (plumbus oxide) | +2, +2.67, +3 Species/+4 Species |
| | | | +2.67 | $Pb_3O_4$ (plumbo-plumbic oxide) | |
| | | | +3 | $Pb_2O_3$ (sequioxide) | |
| IV | A | Lead (Pb) | +4 | $Pb^{+4}$ (plumbic)<br>$PbO_3^{-2}$ (metaplumbate)<br>$HPbO_3^-$ (acid metaplumbate)<br>$PbO_4^{-4}$ (orthoplumbate)<br>$PbO_2$ (dioxide) | +2, +2.67, +3 Species/+4 Species |
| | B | Titanium | +4 | $TiO^{+2}$ (pertitanyl)<br>$HTiO_4^-$ (titanate)<br>$TiO_2$ (dioxide) | +4 Species/+6 Species |
| | | | +6 | $TiO_2^{+2}$ (pertitanyl)<br>$HTiO_4^-$ (acid pertitanate)<br>$TiO_4^{-2}$ (pertitanate)<br>$TiO_3$ (peroxide) | |
| | | Zirconium (Zr) | +4 | $Zr^{+4}$ (zirconic)<br>$ZrO^{+2}$ (zirconyl)<br>$HZrO_3^-$ (zirconate) | +4 Species/+5, +6, +7 Species |
| | | | +5 | $Zr_2O_5$ (pentoxide) | |
| | | | +6 | $ZrO_3$ (peroxide) | |
| | | | +7 | $Zr_2O_7$ (heptoxide) | |
| | | Hafnium (Hf) | +4 | $Hf^{+4}$ (hafnic)<br>$HfO^{+2}$ (hafnyl) | +4 Species/+6 Species |
| | | | +6 | $HfO_3$ (peroxide) | |
| V | A | Nitrogen | +5 | $HNO_3$ (nitric acid)<br>$NO_3^-$ (nitrate) | +5 species/+7 Species |
| | | | +7 | $HNO_4$ (pernitric acid) | |
| | | Phosphorus (P) | +5 | $H_3PO_4$ (orthophosphoric acid)<br>$H_2PO_4^-$ (monoorthophosphate)<br>$HPO_4^{-2}$ (diorthophosphate)<br>$PO_4^{-3}$ (triorthophosphate)<br>$HPO_3$ (metaphosphoric acid)<br>$H_4P_2O_7$ (pryophosphoric acid)<br>$H_5P_3O_{10}$ (triphosphoric acid)<br>$H_6P_4O_{13}$ (tetraphosphoric acid) | +5 Species/+6, +7 species |
| V | A | Phosphorus (P) | +6 | $H_4P_2O_8$ (perphosphoric acid) | +5 Species/+6, +7 Species |
| | | | +7 | $H_3PO_5$ (monoperphosphoric acid) | |
| | | Arsenic (As) | +5 | $H_3AsO_4$ (ortho-arsenic acid)<br>$H_2AsO_4^-$ (mono ortho-arsenate)<br>$HAsO_4^{-2}$ (di-ortho-arsenate)<br>$AsO_4^{-3}$ (tri-ortho-arsenate)<br>$AsO_2^+$ (arsenyl) | +5 Species/+7 species |
| | | | +7 | $AsO_3^+$ (perarsenyl) | |
| | | Bismuth (Bi) | +3 | $Bi^{+3}$ (bismuthous)<br>$BiOH^{+2}$ (hydroxybismuthous)<br>$BiO^+$ (bismuthyl)<br>$BiO_2^-$ (metabismuthite) | +3 Species/+3.5, +4, +5 Species |
| | | | +3.5 | $Bi_4O_7$ (oxide) | |
| | | | +4 | $Bi_2O_4$ (tetroxide) | |
| | | | +5 | $BiO_3^-$ (metabismuthite)<br>$Bi_2O_5$ (pentoxide) | |
| | B | Vanadium (V)<br>(See also POM<br>Complex Anion | +5 | $VO_2^+$ (vanadic)<br>$H_3V_2O_7^-$ (pyrovanadate)<br>$H_2VO_4^-$ (orthovanadate) | +5 Species/+7, +9 Species |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | Mediators | | $VO_3^-$ (metavanadate) | |
| | | | | $HVO_4^{-2}$ (orthovanadate) | |
| | | | | $VO_4^{-3}$ (orthovanadate) | |
| | | | | $V_2O_5$ (pentoxide) | |
| | | | | $H_4V_2O_7$ (pyrovanadic acid) | |
| | | | | $HVO_3$ (metavanadic acid) | |
| | | | | $H_4V_6O_{17}$ (hexavanadic acid) | |
| | | | +7 | $VO_4^-$ (pervanadate) | |
| | | | +9 | $VO_5^-$ (hypervanadate) | |
| VI | B | Chromium | +3 | $Cr^{+3}$ (chromic) | +3 Species/+4, +6 Species |
| | | | | $CrOH^{+2}$, $Cr(OH)_2^1$, (chromyls) | +4 Species/+6 Species |
| | | | | $CrO_2^-$, $CrO_3^{-3}$ (chromites) | |
| | | | | $Cr_2O_3$ (chromic oxide) | |
| | | | | $Cr(OH)_3$ (chromic hydroxide) | |
| | | | +4 | $CrO_2$ (dioxide) | |
| | | | | $Cr(OH)_4$ (hydroxide) | |
| | | | +6 | $H_2CrO_4$ (chromic acid) | |
| | | | | $HCrO_4^-$ (acid chromate) | |
| | | | | $CrO_4^{-2}$ (chromate) | |
| | | | | $Cr_2O_7^{-2}$ (dichromate) | |
| | | Molybdenum (Mo) (See also POM Complex Anion Mediators) | +6 | $HMoO_4^-$ (bimolybhate) | +6 Species/+7 Species |
| | | | | $MoO_4^{-2}$ (molydbate) | |
| | | | | $MoO_3$ (molybdic trioxide) | |
| | | | | $H_2MoO_4$ (molybolic acid) | |
| | | | +7 | $MoO_4^-$ (permolybdate) | |
| | | Tungsten (W) (See also POM Complex Anion Mediators) | +6 | $WO_4^{-2}$ tungstic) | +6 Species/+8 Species |
| | | | | $WO_3$ (trioxide) | |
| | | | | $H_2WO_4$ (tungstic acid) | |
| | | | +8 | $WO_5^{-2}$ (pertungstic) | |
| | | | | $H_2WO_5$ (pertungstic acid) | |
| VII | A | Chlorine (Cl) | −1 | $Cl^-$ (chloride) | −1 Species/+1, +3, +5, +7 Species |
| | | | +1 | HClO (hypochlorous acid) | +1 Species/+3, +5,+7 Species |
| | | | | $ClO^-$ (hypochlorite) | +3 Species/+5, +7 Species |
| | | | +3 | $HClO_2$ (chlorous acid) | +5 Species/+7 Species |
| | | | | $ClO_2^-$ (chlorite) | |
| | | | +5 | $HClO_3$ (chloric acid) | |
| | | | | $ClO_3^-$ (chlorate) | |
| | | | +7 | $HClO_4$ (perchloric acid) | |
| | | | | $ClO_4^-$, $HClO_5^{-2}$, $ClO_5^{-3}$, $Cl_2O_9^{-4}$ (perchlorates) | |
| V | B | Niobium (Nb) (See also POM Complex Anion Mediators) | +5 | $NbO_3^-$ (metaniobate) | +5 Species/+7 species |
| | | | | $NbO_4^{-3}$ (orthoniobate) | |
| | | | | $Nb_2O_5$ (pentoxide) | |
| | | | | $HNbO_3$ (niobid acid) | |
| | | | +7 | $NbO_4^-$ (perniobate) | |
| | | | | $Nb_2O_7$ (perniobic oxide) | |
| | | | | $HNbO_4$ (perniobic acid) | |
| | | Tantalum (Ta) (See also POM Complex Anion Mediators) | +5 | $TaO_3^-$ (metatantalate) | +5 species/+7 species |
| | | | | $TaO_4^{-3}$ (orthotanatalate) | |
| | | | | $Ta_2O_5$ (pentoxide) | |
| | | | | $HTaO_3$ (tantalic acid) | |
| | | | +7 | $TaO_4^-$ (pentantalate) | |
| | | | | $Ta_2O_7$ (pertantalate) | |
| | | | | $HTaO_4 \cdot H_2O$ (pertantalic acid) | |
| VI | A | Sulfur (S) | +6 | $H_2SO_4$ (sulfuric acid) | +6 Species/+7, +8 Species |
| | | | | $HSO_4^-$ (bisulfate) | |
| | | | | $SO_4^{-2}$ (sulfate) | |
| | | | +7 | $S_2O_8^{-2}$ (dipersulfate) | |
| | | | +8 | $H_2SO_5$ (momopersulfuric acid) | |
| | | Selenium (Se) | +6 | $H_2Se_2O_4$ (selenic acid) | +6 species/+7 species |
| | | | | $H_2SeO_4^-$ (biselenate) | |
| | | | | $SeO_4^{-2}$ (selenate) | |
| | | | +7 | $H_2Se_2O_4$ (perdiselenic acid) | |
| | | Tellurium (Te) | +6 | $H_2TeO_4$ (telluric acid) | +6 species/+7 species |
| | | | | $HTeO_4^-$ (bitellurate) | |
| | | | | $TeO_4^{-2}$ (tellurate) | |
| | | | +7 | $H_2Te_2O_8$ (perditellenic acid) | |
| | | Polonium (Po) | +2 | $Po^{+2}$ (polonous) | +2, +4 species/+6 Species |
| | | | +4 | $PoO_3^{-2}$ (polonate) | |
| | | | +6 | $PoO_3$ (peroxide) | |
| VII | A | Bromine (Br) | −1 | $Br^-$ (bromide) | −1 Species/+1, +3, +5, +7 Species |
| | | | +1 | HBrO (hypobromous acid) | +1 Species/+3, +5, +7 Species |
| | | | | $BrO^-$ (hypobromitee) | +3 Species/+5, +7 Species |
| | | | +3 | $HBrO_2$ (bromous acid) | +5 Species/+7 Species |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | | | $BrO_2^-$ (bromite) | |
| | | | +5 | $HBrO_3$ (bromic acid) | |
| | | | | $BrO_3^-$ (bromate) | |
| | | | +7 | $HBrO_4$ (perbromic acid) | |
| | | | | $BrO_4^-$, $HBrO_5^{-2}$, $BrO_5^{-3}$, $Br_2O_9^{-4}$ (prebromates) | |
| | | Iodine | −1 | $I^-$ (iodide) | −1 Species/+1, +3, +5, +7 Species |
| | | | +1 | $HIO$ (hypoiodus acid) | +1 Species/+3, +5, +7 Species |
| | | | | $IO^-$ (hypoiodite) | +3 Species/+5, +7 Species |
| | | | +3 | $HIO_2$ (iodous acid) | +5 Species/+7 Species |
| | | | | $IO_2^-$ (iodite) | |
| | | | +5 | $HIO_3$ (iodic acid) | |
| | | | | $IO_3^-$ (iodate) | |
| | | | +7 | $HIO_4$ (periodic acid) | |
| | | | | $IO_4^-$, $HIO_5^{-2}$, $IO_5^{-3}$, $I_2O_9^{-4}$ (periodates) | |
| | B | Manganese (Mn) | +2 | $Mn^{+2}$ (manganeous) | +2 Species/+3, +4, +6, +7 Species |
| | | | | $HMnO_2^-$ (dimanganite) | +3 Species/+4, +6, +7 Species |
| | | | +3 | $Mn^{+3}$ (manganic) | +4 Species/+6, +7 Species |
| | | | +4 | $MnO_2$ (dioxide) | +6 Species/+7 Species |
| | | | +6 | $MnO_4^{-2}$ (manganate) | |
| | | | +7 | $MnO_4^-$ (permanganate) | |
| VIII | Period 4 | Iron (Fe) | +2 | $Fe^{+2}$ (ferrous) | +2 Species/+3, +4, +5, +6 Species |
| | | | | $HFeO_2^-$ (dihypoferrite) | +3 Species/+4, +5, +6 Species |
| | | | +3 | $Fe^{+3}$, $FeOH^{+2}$, $Fe(OH)_2^1$ (ferric) | +4 Species/+5, +6 Species |
| | | | | $FeO_2^-$ (ferrite) | +5 Species/+6 Species |
| | | | +4 | $FeO^{+2}$ (ferryl) | |
| | | | | $FeO_2^{-2}$ (perferrite) | |
| | | | +5 | $FeO_2^+$ (perferryl) | |
| | | | +6 | $FeO_4^{-2}$ (ferrate) | |
| | | Cobalt (Co) | +2 | $Co^{+2}$ (cobalous) | +2 Species/+3, +4 Species |
| | | | | $HCoO_2^-$ (dicobaltite) | +3 Species/+4 Species |
| | | | +3 | $Co^{+3}$ (cobaltic) | |
| | | | | $Co_2O_3$ (cobaltic oxide) | |
| | | | +3 | $CoO_2$ (peroxide) | |
| | | | | $H_2CoO_3$ (cobaltic acid) | |
| | | Nickel (Ni) | +2 | $Ni^{+2}$ (nickelous) | +2 Species/+3, +4, +6 Species |
| | | | | $NiOH^+$ | +3 Species/+4, +6 Species |
| | | | | $HNiO_2^-$ (dinickelite) | +4 Species/+6 Species |
| | | | | $NiO_2^{-2}$ (nickelite) | |
| | | | +3 | $Ni^{+3}$ (nickelic) | |
| | | | | $Ni_2O_3$ (nickelic oxide) | |
| | | | +4 | $NiO_2$ (peroxide) | |
| | | | +6 | $NiO_4^{-2}$ (nickelate) | |
| VIII | Period 5 | Ruthenium (Ru) | +2 | $Ru^{+2}$ | +2 Species/+3, +4, +5, +6, +7, +8 Species |
| | | | +3 | $Ru^{+3}$ | +3 Species/+4, +5, +6, +7, +8 Species |
| | | | | $Ru_2O_3$ (sesquioxide) | +4 Species/+5, +6, +7, +8 Species |
| | | | | $Ru(OH)_3$ (hydroxide) | +5 Species/+6, +7, +8 Species |
| | | | +4 | $Ru^{+4}$ (ruthenic) | +6 Species/+7, +8 Species |
| | | | | $RuO_2$ (ruthenic dioxide) | +7 Species/+8 Species |
| | | | | $Ru(OH)_4$ (ruthenic hydroxide) | |
| | | | +5 | $Ru_2O_5$ (pentoxide) | |
| | | | +6 | $RuO_4^{-2}$ (ruthenate) | |
| | | | | $RuO_2^{+2}$ (ruthenyl) | |
| | | | | $RuO_3$ (trioxide) | |
| | | | +7 | $RuO_4^-$ (perruthenate) | |
| | | | +8 | $H_2RuO_4$ (hyperuthenic acid) | |
| | | | | $HRuO_5^-$ (diperruthenate) | |
| | | | | $RuO_4$ (ruthenium totroxide) | |
| | | Rhodium (Rh) | +1 | $Rh^+$ (hyporhodous) | +1 Species/+2, +3, +4, +6 Species |
| | | | +2 | $Rh^{+2}$ (rhodous) | +2 Species/+3, +4, +6 Species |
| | | | +3 | $Rh^{+3}$ (rhodic) | +3 Species/+4, +6 Species |
| | | | | $Rh_2O_3$ (sesquioxide) | +4 Species/+6 Species |
| | | | +4 | $RhO_2$ (rhodic oxide) | |
| | | | | $Rh(OH)_4$ (hydroxide) | |
| | | | +6 | $RhO_4^{-2}$ (rhodate) | |
| | | | | $RhO_3$ (trioxide) | |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | Palladium | +2 | $Pd^{+2}$ (palladous) | +2 Species/+3, +4, +6 Species |
| | | | | $PdO_2^{-2}$ (palladite) | +3 Species/+4, +6 Species |
| | | | +3 | $Pd_2O_3$ (sesquioxide) | +4 Species/+6 Species |
| | | | +4 | $PdO_3^{-2}$ (palladate) | |
| | | | | $PdO_2$ (dioxide) | |
| | | | | $Pd(OH)_4$ (hydroxide) | |
| | | | +6 | $PdO_3$ (peroxide) | |
| | Period 6 | Iridium (Ir) | +3 | $Ir^{+3}$ (iridic) | +3 Species/+4, +6 Species |
| | | | | $Ir_2O_3$ (iridium sesquioxide) | +4 Species/+6 Species |
| | | | | $Ir(OH)_3$ (iridium hydroxide) | |
| | | | +4 | $IrO_2$ (iridic oxide) | |
| | | | | $Ir(OH)_4$ (iridic hydroxide) | |
| | | | +6 | $IrO_4^{-2}$ (iridate) | |
| | | | | $IrO_3$ (iridium peroxide) | |
| | | Platinum (Pt) | +2 | $Pt^{+2}$ (platinous) | +2, +3 Species/+4, +6 Species |
| | | | +3 | $Pt_2O_3$ (sesquioxide) | +4 Species/+6 Species |
| | | | +4 | $PtO_3^{-2}$ (palatinate) | |
| | | | | $PtO^{+2}$ (platinyl) | |
| | | | | $Pt(OH)^{+3}$ | |
| | | | | $PtO_2$ (platonic oxide) | |
| IIIB | Rare earths | Cerium (Ce) | +3 | $Ce^{+3}$ (cerous) | +3 Species/+4, +6 Species |
| | | | | $Ce_2O_3$ (cerous oxide) | +4 Species/+6 Species |
| | | | | $Ce(OH)_3$ (cerous hydroxide) | |
| | | | +4 | $Ce^{+4}, Ce(OH)^{+3}, Ce(OH)_2^{+2}$, | |
| | | | | $Ce(OH)_3^+$ (ceric) | |
| | | | | $CeO_2$ (ceric oxide) | |
| | | | +6 | $CeO_3$ (peroxide) | |
| | | Praseodymium (Pr) | +3 | $Pr^{+3}$ (praseodymous) | +3 species/+4 species |
| | | | | $Pr_2O_3$ (sesquioxide) | |
| | | | | $Pr(OH)_3$ (hydroxide) | |
| | | | +4 | $Pr^{+4}$ (praseodymic) | |
| | | | | $PrO_2$ (dioxide) | |
| | | Neodymium | +3 | $Nd^{+3}$ | +3 Species/+4 Species |
| | | | | $Nd_2O_3$ (sesquioxide) | |
| | | | +4 | $NdO_2$ (peroxide) | |
| | | Terbium (Tb) | +3 | $Tb^{+3}$ | +3 Species/+4 Species |
| | | | | $Tb_2O_3$ (sesquioxide) | |
| | | | +4 | $TbO_2$ (peroxide) | |
| | Actinides | Thorium (Th) | +4 | $Th^{+4}$ (thoric) | +4 Species/+6 Species |
| | | | | $ThO^{+2}$ (thoryl) | |
| | | | | $HThO_3^-$ (thorate) | |
| | | | +6 | $ThO_3$ (acid peroxide) | |
| | | Uranium (U) | +6 | $UO_2^{+2}$ (uranyl) | +6 Species/+8 Species |
| | | | | $UO_3$ (uranic oxide) | |
| | | | +8 | $HUO_5^-, UO_5^{-2}$ (peruranates) | |
| | | | | $UO_4$ (peroxide) | |
| | | Neptunium (Np) | +5 | $NpO_2^+$ (hyponeptunyl) | +5 Species/+6, +8 Species |
| | | | | $Np_2O_5$ (pentoxide) | +6 Species/+8 Species |
| | | | +6 | $NpO_2^{+2}$ (neptunyl) | |
| | | | | $NpO_3$ (trioxide) | |
| | | | +8 | $NpO_4$ (peroxide) | |
| | | Plutonium (Pu) | +3 | $Pu^{+3}$ (hypoplutonous) | +3 Species/+4, +5, +6 Species |
| | | | +4 | $Pu^{+4}$ (plutonous) | +4 Species/+5, +6 Species |
| | | | | $PuO_2$ (dioxide) | +5 Species/+6 Species |
| | | | +5 | $PuO_2^+$ (hypoplutonyl) | |
| | | | | $Pu_2O_5$ (pentoxide) | |
| | | | +6 | $PuO_2^{+2}$ (plutonyl) | |
| | | | | $PuO_3$ (peroxide) | |
| | | Americium (Am) | +3 | $Am^{+3}$ (hypoamericious) | |
| | | | +4 | $Am^{+4}$ (americous) | |
| | | | | $AmO_2$ (dioxide) | |
| | | | | $Am(OH)_4$ (hydroxide) | |
| | | | +5 | $AmO_2^+$ (hypoamericyl) | |
| | | | | $Am_2O_5$ (pentoxide) | |
| | | | +6 | $AmO_2^{+2}$ (americyl) | |
| | | | | $AmO_3$ (peroxide) | |

TABLE II

ELEMENTS PARTICIPATING AS HETEROATOMS IN HETEROPOLYANION COMPLEX ANION REDOX COUPLE MEDIATORS

| GROUP | SUB GROUP | ELEMENT |
|---|---|---|
| I | A | Lithium (Li), Sodium (Na), Potassium (K), and Cesium (Cs) |
|  | B | Copper (Cu), Silver (Ag), and Gold (Au) |
| II | A | Beryllium (Be), Magnesium (Mg), Calcium (Ca), Strontium (Sr), and Barium (Ba) |
|  | B | Zinc (Zn), Cadmium (Cd), and Mercury (Hg) |
| III | A | Boron (B), and Aluminum (Al) |
|  | B | Scandium (Sc), and Yttrium (Y) - (See Rare Earths) |
| IV | A | Carbon (C), Silicon (Si), Germanium (Ge), Tin (Sn) and Lead (Pb) |
|  | B | Titanium (Ti), Zirconium (Zr), and Hafnium (Hf) |
| V | A | Nitrogen (N), Phosphorous (P), Arsenic (As), Antimony (Sb), and Bismuth (Bi) |
|  | B | Vanadium (V), Niobium (Nb), and Tantalum (Ta) |
| VI | A | Sulfur (S), Selenium (Se), and Tellurium (Te) |
|  | B | Chromium (Cr), Molybdenum (Mo), and Tungsten (W) |
| VII | A | Fluorine (F), Chlorine (Cl), Bromine (Br), and Iodine (I) |
|  | B | Manganese (Mn), Technetium (Tc), and Rhenium (Re) |
| VIII | Period 4 | Iron (Fe), Cobalt (Co), and Nickel (Ni) |
|  | Period 5 | Ruthenium (Ru), Rhodium (Rh), and Palladium (Pd) |
|  | Period 6 | Osmium (Os), Iridium (Ir), and Platinum (Pt) |
| IIIB | Rare Earths | All | ment contained in both Table I and Table II below or combinations of the mediator oxidizing species from any or all of these generic groups:

TABLE I

Simple Anion Redox Couples

| GROUP | SUB GROUP | ELEMENT | VALENCE |
|---|---|---|---|
| I | A | None |  |
|  | B | Copper (Cu) | +2 |
|  |  |  | +3 |
|  |  |  | +4 |
|  |  | Silver (Ag) | +1 |
|  |  |  | +2 |
|  |  |  | +3 |
|  |  | Gold (Au) | +1 |
|  |  |  | +3 |
|  |  |  | +4 |
| II | A | Magnesium (Mg) | +2 |
|  |  |  | +4 |
|  |  | Calcium (Ca) | +2 |
|  |  |  | +4 |
|  |  | Strontium | +2 |
|  |  |  | +4 |
|  |  | Barium (Ba) | +2 |
|  |  |  | +4 |
| II | B | Zinc (Zn) | +2 |
|  |  |  | +4 |
|  |  | Mercury (Hg) | +2 |
|  |  |  | +4 |
| III | A | Boron | +3 |
|  |  |  | +4.5 |
|  |  |  | +5 |
|  |  | Thallium Tl | +1 |
|  |  |  | +3 |
|  |  |  | 3.33 |
|  | B | See Rare Earths and Actinides |  |
| IV | A | Carbon (C) | +4 |
|  |  |  | +5 |
|  |  |  | +6 |
|  |  | Germanium (Ge) | +4 |
|  |  |  | +6 |
|  |  | Tin (Sn) | +4 |
|  |  |  | +7 |
|  |  | Lead (Pb) | +2 |
|  |  |  | +2.67 |
|  |  |  | +3 |
| IV | A | Lead (Pb) | +4 |
| IV | B | Titanium | +4 |
|  |  |  | +6 |
|  |  | Zirconium (Zr) | +4 |
|  |  |  | +5 |
|  |  |  | +6 |
|  |  |  | +7 |
|  |  | Hafnium (Hf) | +4 |
|  |  |  | +6 |
| V | A | Nitrogen | +5 |
|  |  |  | +7 |
|  |  | Phosphorus (P) | +5 |
| V | A | Phosphorus (P) | +6 |
|  |  |  | +7 |
| V | A | Arsenic (As) | +5 |
|  |  |  | +7 |
|  |  | Bismuth (Bi) | +3 |
|  |  |  | +3.5 |
|  |  |  | +4 |
|  |  |  | +5 |

We claim:

1. A treatment of waste process for the use of mediated electrochemical oxidation (MEO) for the oxidation, conversion/recovery, and decontamination of all previously defined inorganic solid, liquid, or gas where higher oxidation states exist selected from a group consisting of halogenated inorganic compounds (except fluorinated), inorganic pesticides and herbicides, inorganic fertilizers, carbon residues, incinerator residue, inorganic carbon compounds, mineral formations, mining tailings, inorganic salts, metals and metal compounds, and combinations thereof; and combined waste (a mixture of any of the foregoing with each other or other non-inorganic materials) further comprising disposing an electrolyte in an electrochemical cell, separating the electrolyte into an anolyte portion and a catholyte portion with an ion-selective membrane, semi permeable, microporous polymer, ceramic or glass frit membrane; applying a direct current voltage between the anolyte portion and the catholyte portion, placing the waste and/or inorganic materials in the anolyte portion, and oxidizing the waste and/or inorganic materials in the anolyte portion with a mediated electrochemical oxidation (MEO) process, wherein the anolyte portion further comprises a mediator or mediators (oxidizing species) in aqueous solution and containing an acid, neutral or alkaline electrolytes, and wherein the mediator oxidizing species are simple anion redox couples described in Table I as below; Type I isopolyanions complex anion redox couples formed by incorporation of Mo, W, V, Nb, Ta, or mixtures thereof as addenda atoms; Type I heteropolyanions complex anion redox couples formed by incorporation in to Type I isopolyanions as heteroatoms any of the elements listed in Table II either singly or in combination thereof, or heteropolyanions complex anion redox couples containing at least one heteroatom type ele-

TABLE I-continued

Simple Anion Redox Couples

| Group | Subgroup | Species | Oxidation |
|---|---|---|---|
|  | B | Vanadium (V) | +5 |
|  |  |  | +7 |
|  |  |  | +9 |
| V | B | Niobium (Nb) | +5 |
|  |  |  | +7 |
|  |  | Tantalum (Ta) | +5 |
|  |  |  | +7 |
| VI | A | Sulfur (S) | +6 |
|  |  |  | +7 |
|  |  |  | +8 |
|  |  | Selenium (Se) | +6 |
|  |  |  | +7 |
|  |  | Tellurium (Te) | +6 |
|  |  |  | +7 |
|  |  | Polonium (Po) | +2 |
|  |  |  | +4 |
|  |  |  | +6 |
| VI | B | Chromium | +3 |
|  |  |  | +4 |
|  |  |  | +6 |
|  |  | Molybdenum (Mo) | +6 |
|  |  |  | +7 |
|  |  | Tungsten (W) | +6 |
|  |  |  | +8 |
| VII | A | Chlorine (Cl) | +1 |
|  |  |  | +3 |
|  |  |  | +5 |
|  |  |  | +7 |
| VII | A | Bromine (Br) | +1 |
|  |  |  | +3 |
|  |  |  | +5 |
|  |  |  | +7 |
|  |  | Iodine | +1 |
|  |  |  | +3 |
|  |  |  | +5 |
|  |  |  | +7 |
|  | B | Manganese (Mn) | +2 |
|  |  |  | +3 |
|  |  |  | +4 |
|  |  |  | +6 |
|  |  |  | +7 |
| VIII | Period 4 | Iron (Fe) | +3 |
|  |  |  | +4 |
|  |  |  | +5 |
|  |  |  | +6 |
|  |  | Cobalt (Co) | +2 |
|  |  |  | +3 |
|  |  |  | +4 |
|  |  | Nickel (Ni) | +2 |
|  |  |  | +3 |
|  |  |  | +4 |
|  |  |  | +6 |
| VIII | Period 5 | Ruthenium (Ru) | +2 |
|  |  |  | +3 |
|  |  |  | +4 |
|  |  |  | +5 |
|  |  |  | +6 |
|  |  |  | +7 |
|  |  |  | +8 |
|  |  | Rhodium (Rh) | +1 |
|  |  |  | +2 |
|  |  |  | +3 |
|  |  |  | +4 |
|  |  |  | +6 |
|  |  | Palladium | +2 |
|  |  |  | +3 |
|  |  |  | +4 |
|  |  |  | +6 |
| VIII | Period 6 | Iridium (Ir) | +3 |
|  |  |  | +4 |
|  |  |  | +6 |
|  |  | Platinum (Pt) | +2 |
|  |  |  | +3 |
|  |  |  | +4 |
|  |  |  | +6 |
| IIIB | Rare earths | Cerium (Ce) | +3 |
|  |  |  | +4 |
|  |  |  | +6 |
|  |  | Praseodymium (Pr) | +3 |
|  |  |  | +4 |
|  |  | Neodymium | +3 |
|  |  |  | +4 |
|  |  | Terbium (Tb) | +3 |
|  |  |  | +4 |
| IIIB | Actinides | Thorium (Th) | +4 |
|  |  |  | +6 |
|  |  | Uranium (U) | +6 |
|  |  |  | +8 |
|  |  | Neptunium (Np) | +5 |
|  |  |  | +6 |
|  |  |  | +8 |
|  |  | Plutonium (Pu) | +3 |
|  |  |  | +4 |
|  |  |  | +5 |
|  |  |  | +6 |
|  |  | Americium (Am) | +3 |
|  |  |  | +4 |
|  |  |  | +5 |
|  |  |  | +6 |

| GROUP | SUB GROUP | SPECIES | SPECIFIC REDOX COUPLES |
|---|---|---|---|
| I | A |  |  |
|  | B | $Cu^{-2}$ (cupric) | +2 Species/+3, +4 Species: |
|  |  | $HCuO_2$ (bicuprite) | +3 Species/+4 Species |
|  |  | $CuO_2^{-2}$ (cuprite) |  |
|  |  | $Cu^{+3}$ |  |
|  |  | $CuO_2^-$ (cuprate) |  |
|  |  | $Cu_2O_3$ (sesquioxide) |  |
|  |  | $CuO_2$ (peroxide) |  |
|  |  | $Ag^+$ (argentous) | +1 Species/+2, +3 Species: |
|  |  | $AgO^-$ (argentite) | +2 Species/+3 Species |
|  |  | $Ag^{-2}$ (argentic) |  |
|  |  | $AgO$ (argentic oxide) |  |
|  |  | $AgO^+$ (argentyl) |  |
|  |  | $Ag_2O_3$ (sesquioxide) |  |
|  |  | $Au^+$ (aurous) | +1 Species/+3, +4 Species: |
|  |  | $Au^{+3}$ (auric) | +3 Species/+4 Species |
|  |  | $AuO^-$ (auryl) |  |
|  |  | $H_3AuO_3$ (auric acid) |  |
|  |  | $H_2AuO_3^-$ (monoauarate) |  |
|  |  | $HAuO_3^{-2}$ (diaurate) |  |
|  |  | $AuO_3^{-3}$ (triaurate) |  |
|  |  | $Au_2O_3$ (auric oxide) |  |
|  |  | $Au(OH)_3$ (auric hydroxide) |  |
|  |  | $AuO_2$ (peroxide) |  |
| II | A | $Mg^{+2}$ (magnesic) | +2 Species/+4 Species |
|  |  | $MgO_2$ (peroxide) |  |
|  |  | $Ca^{+2}$ | +2 Species/+4 Species |
|  |  | $CaO_2$ (peroxide) |  |
|  |  | $Sr^{+2}$ | +2 Species/+4 Species |
|  |  | $SrO_2$ (peroxide) |  |

TABLE I-continued

Simple Anion Redox Couples

| | | | |
|---|---|---|---|
| II | B | $Ba^{+2}$ | +2 Species/+4 Species |
| | | $BaO_2$ (peroxide) | |
| | | $Zn^{+2}$ (zincic) | +2 Species/+4 Species |
| | | $ZnOH^+$ (zincyl) | |
| | | $HZnO_2^-$ (bizincate) | |
| | | $ZnO_2^{-2}$ (zincate) | |
| | | $ZnO_2$ (peroxide) | |
| | | $Hg^{+2}$ (mercuric) | +2 Species/+4 Species |
| | | $Hg(OH)_2$ (mercuric hydroxide) | |
| | | $HHgO_2^-$ (mercurate) | |
| | | $HgO_2$ (peroxide) | |
| III | A | $H_3BO_3$ (orthoboric acid) | +3 Species/+4.5, +5 Species |
| | | $H_2BO_3^-$, $HBO_3^{-2}$, $BO_3^{-3}$ (orthoborates) | |
| | | $BO_2^-$ (metaborate) | |
| | | $H_2B_4O_7$ (tetraboric acid) | |
| | | $HB_4O_7^-/B_4O_7^{-2}$ (tetraborates) | |
| | | $B_2O_4^{-2}$ (diborate) | |
| | | $B_6O_{10}^{-2}$ (hexaborate) | |
| | | $B_2O_5^{-2}$ (diborate) | |
| | | $BO_3^-/BO_2^- \cdot H_2O$ (perborate) | |
| | | $Tl^{+1}$ (thallous) | +1 Species/+3 or +3.33 Species: |
| | | $Tl^{+3}$ (thallic) | +3 Species/+3.33 Species |
| | | $TlO^+, TlOH^{+2}, Tl(OH)_2^+$ (thallyl) | |
| | | $Tl_2O_3$ (sesquioxide) | |
| | | $Tl(OH)_3$ (hydroxide) | |
| | | $Tl_3O_5$ (peroxide) | |
| IV | A | $H_2CO_3$ (carbonic acid) | +4 Species/+5, +6 Species |
| | | $HCO_3^-$ (bicarbonate) | |
| | | $CO_3^{-2}$ (carbonate) | |
| | | $H_2C_2O_6$ (perdicarbonic acid) | |
| | | $H_2CO_4$ (permonocarbonic acid) | |
| | | $H_2GeO_3$ (germanic acid) | +4 Species/+6 Species |
| | | $HGeO_3^-$ (bigermaniate) | |
| | | $GeO_3^{-4}$ (germinate) | |
| | | $Ge^{+4}$ (germanic) | |
| | | $GeO_4^{-4}$ | |
| | | $H_2Ge_2O_5$ (digermanic acid) | |
| | | $H_2Ge_4O_9$ (tetragermanic acid) | |
| | | $H_2Ge_5O_{11}$ (pentagermanic acid) | |
| | | $HGe_5O_{11}^-$ (bipentagermanate) | |
| | | $Ge_5O_{11}^{-2}$ (pentagermanate) | |
| | | $Sn^{+4}$ (stannic) | +4 Species/+7 Species |
| | | $HSnO_3^-$ (bistannate) | |
| | | $SnO_3^{-2}$ (stannate) | |
| | | $SnO_2$ (stannic oxide) | |
| | | $Sn(OH)_4$ (stannic hydroxide) | |
| | | $SnO_4^-$ (perstannate) | |
| | | $Pb^{+2}$ (plumbous) | +2, +2.67, +3 Species/+4 Species |
| | | $HPbO_2^-$ (biplumbite) | |
| | | $PbOH^+$ | |
| | | $PbO_2^{-2}$ (plumbite) | |
| | | $PbO$ (plumbus oxide) | |
| | | $Pb_3O_4$ (plumbo-plumbic oxide) | |
| | | $Pb_2O_3$ (sequioxide) | |
| IV | A | $Pb^{+4}$ (plumbic) | +2, +2.67, +3 Species/+4 Species |
| | | $PbO_3^{-2}$ (metaplumbate) | |
| | | $HPbO_3^-$ (acid metaplumbate) | |
| IV | B | $PbO_4^{-4}$ (orthoplumbate) | |
| | | $PbO_2$ (dioxide) | |
| | | $TiO^{+2}$ (pertitanyl) | +4 Species/+6 Species |
| | | $HTiO_4^-$ titanate) | |
| | | $TiO_2$ (dioxide) | |
| | | $TiO_2^{+2}$ (pertitanyl) | |
| | | $HTiO_4^-$ (acid pertitanate) | |
| | | $TiO_4^{-2}$ (pertitanate) | |
| | | $TiO_3$ (peroxide) | |
| | | $Zr^{+4}$ (zirconic) | +4 Species/+5, +6, +7 Species |
| | | $ZrO^{+2}$ (zirconyl) | |
| | | $HZrO_3^-$ (zirconate) | |
| | | $Zr_2O_5$ (pentoxide) | |
| | | $ZrO_3$ (peroxide) | |
| | | $Zr_2O_7$ (heptoxide) | |
| | | $Hf^{+4}$ (hafnic) | +4 Species/+6 Species |
| | | $HfO^{+2}$ (hafnyl) | |
| | | $HfO_3$ (peroxide) | |
| V | A | $HNO_3$ (nitric acid) | +5 Species/+7 Species |
| | | $NO_3^-$ (nitrate) | |
| | | $HNO_4$ (pernitric acid) | |
| | | $H_3PO_4$ (orthophosphoric acid) | +5 Species/+6, +7 species |
| | | $H_2PO_4^-$ (monoorthophosphate) | |
| | | $HPO_4^{-2}$ (diorthophosphate) | |
| | | $PO_4^{-3}$ (triorthophosphate) | |
| | | $HPO_3$ (metaphosphoric acid) | |
| | | $H_4P_2O_7$ (pryophosphoric acid) | |
| | | $H_5P_3O_{10}$ (triphosphoric acid) | |
| | | $H_6P_4O_{13}$ (tetraphosphoric acid) | |
| V | A | $H_4P_2O_8$ (perphosphoric acid) | +5 Species/+6, +7 Species |
| | | $H_3PO_5$ (monoperphosphoric acid) | |
| | | $H_3AsO_4$ (ortho-arsenic acid) | +5 Species/+7 species |
| | | $H_2AsO_4^-$ (mono ortho-arsenate) | |
| | | $HAsO_4^{-2}$ (di-ortho-arsenate) | |
| | | $AsO_4^{-3}$ (tri-ortho-arsenate) | |
| | | $AsO_2^+$ (arsenyl) | |
| | | $AsO_3^+$ (perarsenyl) | |
| | | $Bi^{+3}$ (bismuthous) | +3 Species/+3.5, +4, +5 Species |
| | | $BiOH^{+2}$ (hydroxybismuthous) | |
| | | $BiO^+$ (bismuthyl) | |
| | | $BiO_2^-$ (metabismuthite) | |
| | | $Bi_4O_7$ (oxide) | |
| | | $Bi_2O_4$ (tetroxide) | |
| | | $BiO_3^-$ (metabismuthite) | |
| | | $Bi_2O_5$ (pentoxide) | |
| | B | $VO_2^-$ (vanadic) | +5 Species/+7, +9 Species |
| | | $H_3V_2O_7$ (pyrovanadate) | |
| | | $H_2VO_4^-$ (orthovanadate) | |
| | | $VO_3^-$ (metavanadate) | |
| | | $HVO_4^{-2}$ (orthovanadate) | |
| | | $VO_4^{-3}$ (orthovanadate) | |
| | | $V_2O_5$ (pentoxide) | |
| | | $H_4V_2O_7$ (pyrovanadic acid) | |
| | | $HVO_3$ (metavanadic acid) | |
| | | $H_4V_6O_{17}$ (hexavanadic acid) | |
| | | $VO_4^-$ (pervanadate) | |
| | | $VO_5^-$ (hypervanadate) | |
| V | B | $NbO_3^-$ (metaniobate) | +5 Species/+7 species |
| | | $NbO_4^{-3}$ (orthoniobate) | |
| | | $Nb_2O_5$ (pentoxide) | |
| | | $HNbO_3$ (niobid acid) | |
| | | $NbO_4^-$ (perniobate) | |
| | | $Nb_2O_7$ (perniobic oxide) | |
| | | $HNbO_4$ (perniobic acid) | |

TABLE I-continued

Simple Anion Redox Couples

| | | | |
|---|---|---|---|
| | | $TaO_3^{-3}$ (metatantalate) | +5 species/+7 species |
| | | $TaO_4^{-3}$ (orthotanatalate) | |
| | | $Ta_2O_5$ (pentoxide) | |
| | | $HTaO_3$ (tantalic acid) | |
| | | $TaO_4^-$ (pentantalate) | |
| | | $Ta_2O_7$ (pertantalate) | |
| | | $HTaO_4 \cdot H_2O$ (pertantalic acid) | |
| VI | A | $H_2SO_4$ (sulfuric acid) | +6 Species/+7 +8 Species |
| | | $HSO_4^-$ (bisulfate) | |
| | | $SO_4^{-2}$ (sulfate) | |
| | | $S_2O_8^{-2}$ (dipersulfate) | |
| | | $H_2SO_5$ (momopersulfuric acid) | |
| | | $H_2Se_2O_4$ (selenic acid) | +6 species/+7 Species |
| | | $HSeO_4^-$ (biselenate) | |
| | | $SeO_4^{-2}$ (selenate) | |
| | | $H_2Se_2O_8$ (perdiselenic acid) | |
| | | $H_2TeO_4$ (telluric acid) | +6 species/+7 species |
| | | $HTeO_4^-$ (bitellurate) | |
| | | $TeO_4^{-2}$ (tellurate) | |
| | | $H_2Te_2O_8$ (perditellenic acid) | |
| | | $Po^{+2}$ (polonous) | +2, +4 species/ +6 Species |
| | | $PoO_3^{-2}$ (polonate) | |
| | | $PoO_3$ (peroxide) | |
| VI | B | $Cr^{+3}$ (chromic) | +3 Species/ +4, +6 Species; |
| | | $CrOH^{+2}$, $Cr(OH)_2^+$ (chromyls) | +4 Species/ +6 Species |
| | | $CrO_2^-$, $CrO_3^{-3}$ (chromites) | |
| | | $Cr_2O_3$ (chromic oxide) | |
| | | $Cr(OH)_3$ (chromic hydroxide) | |
| | | $CrO_2$ (dioxide) | |
| | | $Cr(OH)_4$ (hydroxide) | |
| | | $H_2CrO_4$ (chromic acid) | |
| | | $HCrO_4^-$ (acid chromate) | |
| | | $CrO_4^{-2}$ (chromate) | |
| | | $Cr_2O_7^{-2}$ (dichromate) | |
| | | $HMoO_4^-$ (bimolybhate) | +6 Species/ +7 Species |
| | | $MoO_4^{-2}$ (molydbate) | |
| | | $MoO_3$ (molybdic trioxide) | |
| | | $H_2MoO_4$ (molybolic acid) | |
| | | $MoO_4^{-2}$ (permolybdate) | |
| | | $WO_4^{-2}$ (tungstic) | +6 Species/ +8 Species |
| | | $WO_3$ (trioxide) | |
| | | $H_2WO_4$ (tungstic acid) | |
| | | $WO_5^{-2}$ (pertungstic) | |
| | | $H_2WO_5$ (pertungstic acid) | |
| VII | A | HClO (hypochlorous acid) | +1 Species/+3, +5, +7 Species; |
| | | $ClO^-$ (hypochlorite) | +3 Species/ +5, +7 Species; |
| | | $HClO_2$ (chlorous acid) | +5 Species/ +7 Species |
| | | $ClO_2^-$ (chlorite) | |
| | | $HClO_3$ (chloric acid) | |
| | | $ClO_3^-$ (chlorate) | |
| | | $HClO_4$ (perchloric acid) | |
| | | $ClO_4^-$, $HClO_5^{-2}$, $ClO_5^{-3}$, $Cl_2O_9^{-4}$ (perchlorates) | |
| VII | A | HBrO (hypobromous acid) | +1 Species/+3, +5, +7 Species; |
| | | $BrO^-$ (hypobromitee) | +3 Species/+5, +7 Species; |
| | | $HBrO_2$ (bromous acid) | +5 Species/+7 Species |
| | | $BrO2^-$ (bromite) | |
| | | $HBrO_3$ (bromic acid) | |
| | | $BrO_3^-$ (bromate) | |
| | | $HBrO_4$ (perbromic acid) | |
| | | $BrO_4^-$, $HBrO_5^{-2}$, $BrO_5^{-3}$, $Br_2O_9^{-4}$ (prebromates) | |
| | | HIO (hypoiodus acid) | +1 Species/+3, +5, +7 Species |
| | | $IO^-$ (hypoiodite) | +3 Species/+5, +7 Species; |
| | | $HIO_2$ (iodous acid) | +5 Species/+7 Species |
| | | $IO_2^-$ (iodite) | |
| | | $HIO_3$ (iodic acid) | |
| | | $IO_3^-$ (iodate) | |
| | | $HIO_4$ (periodic acid) | |
| | | $IO_4^-$, $HIO_5^{-3}$, $IO_5^{-3}$, $I_2O_9^{-4}$ (periodates) | |
| | B | $Mn^{+2}$ (manganeous) | +2 Species/+3, +4, +6, +7 Species; |
| | | $HIMnO_2^-$ (dimanganite) | +3 Species/+4, +6, +7 Species; |
| | | $Mn^{+3}$ (manganic) | +4 Species/+6, +7 Species |
| | | $MnO_2$ (dioxide) | +6 Species/+7 Species |
| | | $MnO_4^{-2}$ (manganate) | |
| | | $MnO_4^-$ (permanganate) | |
| VIII | Period 4 | $Fe^{+3}$ (ferric) | +3 Species/+4, +5, +6 Species; |
| | | $Fe(OH)^{+2}$ | |
| | | $Fe(OH)_2^{\pm}$ | |
| | | $FeO_2^{-2}$ (ferrite) | |
| | | $FeO^{+2}$ (ferryl) | +4 Species/ +5, +6 Species; |
| | | $FeO_2^{-2}$ (perferrite) | +5 Species/ +6 Species |
| | | $FeO_2^+$ (perferryl) | |
| | | $FeO_4^{-2}$ (ferrate) | |
| | | $Co^{+2}$ (cobalous) | +2 Species/ +3, +4 Species; |
| | | $HCoO_2^-$ (dicobaltite) | +3 Species/ +4 Species |
| | | $Co^{+3}$ (cobaltic) | |
| | | $Co_2O_3$ (cobaltic oxide) | |
| | | $CoO_2$ (peroxide) | |
| | | $H_2CoO_3$ (cobaltic acid) | |
| | | $Ni^{+2}$ (nickelous) | +2 Species/+3, +4, +6 Species; |
| | | $NiOH^+$ | +3 Species/ +4, +6 Species; |
| | | $HNiO_2^-$ (dinickelite) | +4 Species/ +6 Species |
| | | $NiO_2^{-2}$ (nickelite) | |
| | | $Ni^{+3}$ (nickelic) | |
| | | $Ni_2O_3$ (nickelic oxide) | |
| | | $NiO_2$ (peroxide) | |
| | | $NiO_4^{-2}$ (nickelate) | |
| VIII | Period 5 | $Ru^{+2}$ | +2 Species/+3, +4, +5, +6, +7, +8 Species; |
| | | $Ru^{+3}$ | +3 Species/+4, +5, +6, +7, +8 Species; |
| | | $Ru_2O_3$ (sesquioxide) | +4 Species/ +5, +6, +7, +8 Species; |
| | | $Ru(OH)_3$ (hydroxide) | +5 Species/+6, +7, +8 Species; |
| | | $Ru^{+4}$ (ruthenic) | +6 Species/ +7, +8 Species; |
| | | $RuO_2$ (ruthenic dioxide) | +7 Species/ +8 Species |
| | | $Ru(OH)_4$ (ruthenic hydroxide) | |
| | | $Ru_2O_5$ (pentoxide) | |
| | | $RuO_4^{-2}$ (ruthenate) | |
| | | $RuO_4^{+2}$ (ruthenyl) | |
| | | $RuO_3$ (trioxide) | |
| | | $RuO_4^-$ (perruthenate) | |
| | | $H_2RuO_4$ (hyperuthenic acid) | |

TABLE I-continued

Simple Anion Redox Couples

| | | |
|---|---|---|
| | HRuO$_5^-$ (diperruthenate) | |
| | RuO$_4$ (ruthenium tetroxide) | |
| | Rh$^+$ (hyporhodous) | +1 Species/+2, +3, +4, +6 Species; |
| | Rh$^{+2}$ (rhodous) | +2 Species/+3, +4, +6 Species; |
| | Rh$^{+3}$ (rhodic) | +3 Species/+4, +6 Species; |
| | Rh$_2$O$_3$ (sesquioxide) | +4 Species/+6 Species |
| | RhO$_2$ (rhodic oxide) | |
| | Rh(OH)$_4$ (hydroxide) | |
| | RhO$_4^{-2}$ (rhodate) | |
| | RhO$_3$ (trioxide) | |
| | Pd$^{+2}$ (palladous) | +2 Species/+3, +4, +6 Species; |
| | PdO$_2^{-2}$ (palladite) | +3 Species/+4, +6 Species; |
| | Pd$_2$O$_3$ (sesquioxide) | +4 Species/+6 Species |
| | Pd O$_3^{-2}$ (palladate) | |
| | PdO$_2$ (dioxide) | |
| | Pd(OH)$_4$ (hydroxide) | |
| | PdO$_3$ (peroxide) | |
| VIII Period 6 | Ir$^{+3}$ (iridic) | +3 Species/+4, +6 Species; |
| | Ir$_2$O$_3$ (iridium sesquioxide) | +4 Species/+6 Species |
| | Ir(OH)$_3$ (iridium hydroxide) | |
| | IrO$_2$ (iridic oxide) | |
| | Ir (OH)$_4$ (iridic hydroxide) | |
| | IrO$_4^{-2}$ (iridate) | |
| | IrO$_3$ (iridium peroxide) | |
| | Pt$^{+2}$ (platinous) | +2, +3 Species/+4, +6 Species; |
| | Pt$_2$O$_3$ (sesquioxide) | +4 Species/+6 Species |
| | PtO$_3^{-2}$ (palatinate) | |
| | PtO$^{+2}$ (platinyl) | |
| | Pt(OH)$^{+3}$ | |
| | PtO$_2$ (platonic oxide) | |
| | PtO$_4^{-2}$ (Perplatinate) | |
| | PtO$_3$ (perplatinic oxide) | |
| IIIB Rare earths | Ce$^{+3}$ (cerous) | +3 Species/+4, +6 Species; |
| | Ce$_2$O$_3$ (cerous oxide) | +4 Species/+6 Species |
| | Ce(OH)$_3$ (cerous hydroxide) | |
| | Ce$^{+4}$, Ce(OH)$^{+3}$, Ce(OH)$_2^{+2}$, Ce(OH)$_3^+$ (ceric) | |
| | CeO$_2$ (ceric oxide) | |
| | CeO$_3$ (peroxide) | |
| | Pr$^{+3}$ (praseodymous) | +3 species/+4 species |
| | Pr$_2$O$_3$ (sesquioxide) | |
| | Pr(OH)$_3$ (hydroxide) | |
| | Pr$^{+4}$ (praseodymic) | |
| | PrO$_2$ (dioxide) | |
| | Nd$^{+3}$ | +3 Species/+4 Species |
| | Nd$_2$O$_3$ (sesquioxide) | |
| | NdO$_2$ (peroxide) | |
| | Tb$^{+3}$ | +3 Species/+4 Species |
| | Tb$_2$O$_3$ (sesquioxide) | |
| | TbO$_2$ (peroxide) | |
| IIIB Actinides | Th$^{+4}$ (thoric) | +4 Species/+6 Species |
| | ThO$^{+2}$ (thoryl) | |
| | HThO$_3^-$ (thorate) | |
| | ThO$_3$ (acid peroxide) | |
| | UO$_2^{+2}$ (uranyl) | +6 Species/+8 Species |
| | UO$_3$ (uranic oxide) | |
| | HUO$_5^-$, UO$_5^{-2}$ (peruranates) | |
| | UO$_4$ (peroxide) | |
| | NpO$_2^+$ (hyponeptunyl) | +5 Species/+6, +8 Species; |
| | NP$_2$O$_5$ (pentoxide) | +6 Species/+8 Species |
| | NpO$_2^{+2}$ (neptunyl) | |
| | NpO$_3$ (trioxide) | |
| | NpO$_4$ (peroxide) | |
| | Pu$^{+3}$ (hypoplutonous) | +3 Species/+4, +5, +6 Species; |
| | Pu$^{+4}$ (plutonous) | +4 Species/+5, +6 Species; |
| | PuO$_2$ (dioxide) | +5 Species/+6 Species |
| | PuO$_2^+$ (hypoplutonyl) | |
| | Pu$_2$O$_5$ (pentoxide) | |
| | PuO$_2^{+2}$ (plutonyl) | |
| | PuO$_3$ (peroxide) | |
| | Am$^{+3}$ (hypoamericious) | +3 Species/+4, +5, +6 Species; |
| | Am$^{+4}$ (americous) | +4 Species/+5, +6 Species; |
| | AmO$_2$ (dioxide) | +5 Species/+6 Species |
| | Am(OH)$_4$ (hydroxide) | |
| | AmO$_2^+$ (hypoamericyl) | |
| | Am$_2$O$_5$ (pentoxide) | |
| | AmO$_2^{+2}$ (americyl) | |
| | AmO$_3$ (peroxide) | |

TABLE II

Elements Participating as Heteroatoms in Heteropolyanion Complex Anion Redox Couple Mediators

| GROUP | SUB GROUP | ELEMENT |
|---|---|---|
| I | A | Lithium (Li), Sodium (Na), Potassium (K), and Cesium (Cs) |
| | B | Copper (Cu), Silver (Ag), and Gold (Au) |
| II | A | Beryllium (Be), Magnesium (Mg), Calcium (Ca), Strontium (Sr), and B |
| | B | Zinc (Zn), Cadmium (Cd), and Mercury (Hg) |
| III | A | Boron (B), and Aluminum (Al) |
| | B | Scandium (Sc), and Yttrium (Y) - (See Rare Earths) |
| IV | A | Carbon (C), Silicon (Si), Germanium (Ge), Tin (Sn) and Lead (Pb) |
| | B | Titanium (Ti), Zirconium (Zr), and Hafnium (Hf) |
| V | A | Nitrogen (N), Phosphorous (P), Arsenic (As), Antimony (Sb), and Bism |
| | B | Vanadium (V), Niobium (Nb), and Tantalum (Ta) |
| VI | A | Sulfur (S), Selenium (Se), and Tellurium (Te) |
| | B | Chromium (Cr), Molybdenum (Mo), and Tungsten (W) |
| VII | A | Fluorine (F), Chlorine (Cl), Bromine (Br), and Iodine (I) |
| | B | Manganese (Mn), Technetium (Tc), and Rhenium (Re) |
| VIII | Period 4 | Iron (Fe), Cobalt (Co), and Nickel (Ni) |
| | Period 5 | Ruthenium (Ru), Rhodium (Rh), and Palladium (Pd) |
| | Period 6 | Osmium (Os), Iridium (Ir), and Platinum (Pt) |
| IIIB | Rare Earths | All. |

2. The process of claim 1, further comprising adding stabilizing compounds to the electrolyte for overcoming and stabilizing the short lifetime of oxidized forms of higher oxidation state species of the mediator oxidizing species, and further comprising additives disposed in the electrolyte thereby increasing the kinetics of the mediated electrochemical processes of the mediated electrochemical processes while keeping it from becoming directly involved in the oxidizing of the waste and/or inorganic materials, and stabilizer compounds disposed in the electrolyte for stabilizing higher oxidation state species of oxidized forms of the reversible redox couples used as the mediator oxidizing species in the electrolyte.

3. The process of claim 1, wherein the mediator oxidizing species are super oxidizers which exhibit oxidation potentials of at least 1.7 volts at 1 molar, 25° C. and pH 1 and which are redox couple species that have the capability of producing free radicals of hydroxyl or perhydroxyl, and further comprising creating free radical secondary oxidizers by reacting the super oxidizers with water, adding energy from an energy source, ultra sonic and/or ultraviolet, to the anolyte portion and augmenting the secondary oxidation processes, breaking down hydrogen peroxide in the anolyte portion into hydroxyl free radicals, and increasing an oxidizing effect of the secondary oxidation processes, and further comprising generating inorganic free radicals in acqueous solutions from a group consisting of carbonate, azide, nitrite, nitrate, phosphite, phosphate, sulfite, sulfate, selenite, thiocyanate, chloride, bromide, iodide, and formate oxidizing species and combinations thereof.

4. The process of claim 1, further comprising using an alkaline solution, aiding decomposing of the biological materials in waste and/or inorganic materials derived from base promoted ester hydrolysis, saponification, of fatty acids, and forming water soluble alkali metal salts of the fatty acids and glycerin in a process similar to the production of soap from animal fat by introducing it into a hot aqueous lye solution.

5. The process of claim 1, further comprising using an alkaline anolyte solution for aiding decomposing the materials, for absorbing $CO_2$ from the oxidizing of waste and/or inorganic materials and forming alkali metal bicarbonate/carbonate solutions, which subsequently circulate through the electrochemical cell, producing percarbonate oxidizers.

6. The process of claim 1, further comprising impressing an AC voltage upon the direct current voltage for retarding formation of cell performance limiting surface films on the electrodes or the membrane.

7. The process of claim 1, further comprising adjusting temperature between 0° C. and slightly below the boiling point of the anolyte portion before it enters the electrochemical cell for enhancing generation of oxidized forms of the mediator oxidizing species, and adjusting the temperature between 0° C. and below the boiling temperature of the anolyte portion entering the anolyte reaction chamber affecting desired chemical reactions at desired rates.

8. The process of claim 1, further comprising introducing an ultrasonic energy into the anolyte portion, rupturing cell membranes in the biological materials in waste and/or inorganic materials by momentarily raising local temperature and pressure within the cell membranes with the ultrasonic energy to above several thousand degrees and thousand atmospheres, and causing cell membrane failure, and wherein the added energy comprises using ultrasonic energy and inducing microscopic bubble expansion and implosion for reducing in size individual second phase mixed waste volumes dispersed in the anolyte.

9. The process of claim 1, further comprising inorganic waste containing elements that are identified in Table I as anion redox couples, they become possible mediated redox couples when the oxidation of the inorganic waste releases them into solution as the reduced form of the redox couple and are raised to the oxidized form when they pass through the electrochemical cell.

10. The process of claim 1, further comprising introducing ultraviolet energy into the anolyte portion and decomposing hydrogen peroxide into hydroxyl free radicals therein, thereby increasing efficiency of the process by converting products of electron consuming parasitic reactions, hydrogen peroxide, into viable free radical secondary oxidizers without consumption of additional electrons.

11. The process of claim 1, further comprising adding a surfactant to the anolyte portion for promoting dispersion of the waste and/or inorganic materials or intermediate stage reaction products within the aqueous solution when the waste and/or inorganic materials or reaction products are not water-soluble and tend to form immiscible layers.

12. The process of claim 1, further comprising attacking specific organic molecules in the waste and/or inorganic materials with the mediator oxidizing species while operating at a sufficiently low temperatures and preventing formation of dioxins and furans.

13. The process of claim 1, further comprising breaking down the waste and/or inorganic materials into biological and organic compounds and attacking these compounds using as the mediator simple and/or complex anion redox couple mediators or inorganic free radicals and generating organic free radicals.

14. The process of claim 1, further comprising raising normal valence state mediator anions to a higher valence state by stripping the mediator anions of electrons in the electrochemical cell, wherein oxidized forms of weaker redox couples present in the mediator oxidizing species are produced by similar anodic oxidation or reaction with oxidized forms of stronger redox couples present and the oxidized species of the redox couples oxidize molecules of the waste and/or inorganic materials and are themselves converted to their reduced form, whereupon they are oxidized by the aforementioned mechanisms and the redox cycle continues.

15. A process for treating and waste comprising oxidizing waste and/or inorganic materials, comprising circulating anions of mediator oxidizing species in an electrolyte through an electrochemical cell with an ion-selective membrane, semi permeable, microporous polymer, ceramic or glass frit membrane, and affecting anodic oxidation of reduced forms of reversible redox couples into oxidized forms, contacting the anions with the waste and/or inorganic materials in an anolyte portion of the electrolyte in a primary oxidation process, involving super oxidizer anions, having an oxidation potential above a threshold value of 1.7 volts at 1 molar, 25° C. and pH1 are present there is creating a free radical oxidizer driven secondary oxidation process, adding energy from an energy source to the anolyte portion and augmenting the secondary oxidation processes, breaking down hydrogen peroxide in the anolyte portion into hydroxyl free radicals, and increasing an oxidizing effect of the secondary oxidation processes, wherein the mediator oxidizing species are simple anion redox couples described in Table I as below; Type I isopolyanions complex anion redox couples formed by incorporation of Mo, W, V, Nb, Ta, or mixtures thereof as addenda atoms; Type I heteropolyanions complex anion redox couples formed by incorporation in to Type I isopolyanions as heteroatoms any of the elements listed in Table II either singly or in combination thereof, or heteropolyanions complex anion redox couples containing at least one heteroatom type element contained in both Table I and Table II below or combinations of the mediator oxidizing species from any or all of these generic groups:

TABLE I

Simple Anion Redox Couples

| GROUP | SUB GROUP | ELEMENT | VALENCE | SPECIES | SPECIFIC REDOX COUPLES |
|---|---|---|---|---|---|
| I | A | None | | | |
| | B | Copper (Cu) | +2 | $Cu^{-2}$ (cupric) | +2 Species/+3, +4 Species; |
| | | | | $HCuO_2^-$ (bicuprite) $CuO_2^{-2}$ (cuprite) | +3 Species/+4 Species |
| | | | +3 | $Cu^{+3}$ | |
| | | | | $CuO_2^-$ (cuprate) $Cu_2O_3$ (sesquioxide) | |
| | | | +4 | $CuO_2$ (peroxide) | |
| | | Silver (Ag) | +1 | $Ag^+$ (argentous) | +1 Species/+2, +3 Species; |
| | | | | $AgO^-$ (argentite) | +2 Species/+3 Species |
| | | | +2 | $Ag^{-2}$ (argentic) $AgO$ (argentic oxide) | |
| | | | +3 | $AgO^+$ (argentyl) $Ag_2O_3$ (sesquioxide) | |
| | | Gold (Au) | +1 | $Au^+$ (aurous) | +1 Species/+3, +4 Species; |
| | | | +3 | $Au^{+3}$ (auric) | +3 Species/+4 Species |
| | | | | $AuO^-$ (auryl) $H_3AuO_3^-$ (auric acid) $H_2AuO_3^-$ (monoauarate) $HAuO_3^{-2}$ (diaurate) $AuO_3^{-3}$ (triaurate) $Au_2O_3$ (auric oxide) $Au(OH)_3$ (auric hydroxide) | |
| | | | +4 | $AuO_2$ (peroxide) | |
| II | A | Magnesium (Mg) | +2 | $Mg^{+2}$ (magnesic) | +2 Species/+4 Species |
| | | | +4 | $MgO_2$ (peroxide) | |
| | | Calcium (Ca) | +2 | $Ca^{+2}$ | +2 Species/+4 Species |
| | | | +4 | $CaO_2$ (peroxide) | |
| | | Strontium | +2 | $Sr^{+2}$ | +2 Species/+4 Species |
| | | | +4 | $SrO_2$ (peroxide) | |
| | | Barium (Ba) | +2 | $Ba^{+2}$ | +2 Species/+4 Species |
| | | | +4 | $BaO_2$ (peroxide) | |
| II | B | Zinc (Zn) | +2 | $Zn^{+2}$ (zincic) | +2 Species/ +4 Species |
| | | | | $ZnOH^+$ (zincyl) $HZnO_2^-$ (bizincate) $ZnO_2^{-2}$ (zincate) | |
| | | | +4 | $ZnO_2$ (peroxide) | |
| | | Mercury (Hg) | +2 | $Hg^{+2}$ (mercuric) | +2 Species/ +4 Species |
| | | | | $Hg(OH)_2$ (mercuric hydroxide) $HHgO_2^-$ (mercurate) | |
| | | | +4 | $HgO_2$ (peroxide) | |
| III | A | Boron | +3 | $H_3BO_3$ (orthoboric acid) | +3 Species/ +4.5, +5 Species |
| | | | | $H_2BO_3^-$, $HBO_3^{-2}$, $BO_3^{-3}$ (orthoborates) $BO_2^-$ (metaborate) $H_2B_4O_7$ (tetraboric acid) $HB_4O_7^-/B_4O_7^{-2}$ (tetraborates) $B_2O_4^{-2}$ (diborate) $B_6O_{10}^{-2}$ (hexaborate) | |
| | | | +4.5 | $B_2O_5^-$ (diborate) | |
| | | | +5 | $BO_3^-/BO_2^- \cdot H_2O$ (perborate) | |
| | | Thallium (Tl) | +1 | $Tl^{+1}$ (thallous) | +1 Species/ +3 or +3.33 Species; |
| | | | +3 | $Tl^{+3}$ (thallic) | +3 Species/ +3.33 Species |
| | | | | $TlO^+$, $TlOH^{+2}$, $Tl(OH)_2^{\pm}$ (thallyl) $Tl_2O_3$ (sesquioxide) $Tl(OH)_3$ (hydroxide) | |
| | | | +3.33 | $Tl_3O_5$ (peroxide) | |

TABLE I-continued

Simple Anion Redox Couples

| GROUP | SUB GROUP | ELEMENT | VALENCE | SPECIES | SPECIFIC REDOX COUPLES |
|---|---|---|---|---|---|
| | B | | | See Rare Earths and Actinides | |
| IV | A | Carbon (C) | +4 | $H_2CO_3$ (carbonic acid) | +4 Species/ +5, +6 Species |
| | | | | $HCO_3^-$ (bicarbonate) | |
| | | | | $CO_3^{-2}$ (carbonate) | |
| | | | +5 | $H_2C_2O_6$ (perdicarbonic acid) | |
| | | | +6 | $H_2CO_4$ (permonocarbonic acid) | |
| | | Germanium (Ge) | +4 | $H_2GeO_3$ (germanic acid) | +4 Species/ +6 Species |
| | | | | $HGeO_3^-$ (bigermaniate) | |
| | | | | $GeO_3^{-4}$ (germinate) | |
| | | | | $Ge^{+4}$ (germanic) | |
| | | | | $GeO_4^{-4}$ | |
| | | | | $H_2Ge_2O_5$ (digermanic acid) | |
| | | | | $H_2Ge_4O_9$ (tetragermanic acid) | |
| | | | | $H_2Ge_5O_{11}$ (pentagermanic acid) | |
| | | | | $HGe_5O_{11}^-$ (bipentagermanate) | |
| | | | +6 | $Ge_5O_{11}^{-2}$ (pentagermanate) | |
| | | Tin (Sn) | +4 | $Sn^{+4}$ (stannic) | +4 Species/ +7 Species |
| | | | | $HSnO_3^-$ (bistannate) | |
| | | | | $SnO_3^{-2}$ (stannate) | |
| | | | | $SnO_2$ (stannic oxide) | |
| | | | | $Sn(OH)_4$ (stannic hydroxide) | |
| | | | +7 | $SnO_4^-$ (perstannate) | |
| | | Lead (Pb) | +2 | $Pb^{+2}$ (plumbous) | +2, +2.67, +3 Species/+4 Species |
| | | | | $HPbO_2^-$ (biplumbite) | |
| | | | | $PbOH^+$ | |
| | | | | $PbO_2^{-2}$ (plumbite) | |
| | | | | $PbO$ (plumbus oxide) | |
| | | | +2.67 | $Pb_3O_4$ (plumbo-plumbic oxide) | |
| | | | +3 | $Pb_2O_3$ (sequioxide) | |
| IV | A | Lead (Pb) | +4 | $Pb^{+4}$ (plumbic) | +2, +2.67, +3 Species/+4 Species |
| | | | | $PbO_3^{-2}$ (metaplumbate) | |
| | | | | $HPbO_3^-$ (acid metaplumbate) | |
| | | | | $PbO_4^{-4}$ (orthoplumbate) | |
| | | | | $PbO_2$ (dioxide) | |
| IV | B | Titanium | +4 | $TiO^{+2}$ (pertitanyl) | +4 Species/ +6 Species |
| | | | | $HTiO_4^-$ titanate) | |
| | | | | $TiO_2$ (dioxide) | |
| | | | +6 | $TiO_2^{+2}$ (pertitanyl) | |
| | | | | $HTiO_4^-$ (acid pertitanate) | |
| | | | | $TiO_4^{-2}$ (pertitanate) | |
| | | | | $TiO_3$ (peroxide) | |
| | | Zirconium (Zr) | +4 | $Zr^{+4}$ (zirconic) | +4 Species/+5, +6, +7 Species |
| | | | | $ZrO^{+2}$ (zirconyl) | |
| | | | | $HZrO_3^-$ (zirconate) | |
| | | | +5 | $Zr_2O_5$ (pentoxide) | |
| | | | +6 | $ZrO_3$ (peroxide) | |
| | | | +7 | $Zr_2O_7$ (heptoxide) | |
| | | Hafnium (Hf) | +4 | $Hf^{+4}$ (hafnic) | +4 Species/ +6 Species |
| | | | | $HfO^{+2}$ (hafnyl) | |
| | | | +6 | $HfO_3$ (peroxide) | |
| V | A | Nitrogen | +5 | $HNO_3$ (nitric acid) | +5 species/ +7 Species |
| | | | | $NO_3^-$ (nitrate) | |
| | | | +7 | $HNO_4$ (pernitric acid) | |
| | | Phosphorus (P) | +5 | $H_3PO_4$ (orthophosphoric acid) | +5 Species/ +6, +7 species |
| | | | | $H_2PO_4^-$ (monoorthophosphate) | |
| | | | | $HPO_4^{-2}$ (diorthophosphate) | |
| | | | | $PO_4^{-3}$ triorthophosphate) | |
| | | | | $HPO_3$ (metaphosphoric acid) | |

TABLE I-continued

Simple Anion Redox Couples

| GROUP | SUB GROUP | ELEMENT | VALENCE | SPECIES | SPECIFIC REDOX COUPLES |
|---|---|---|---|---|---|
| | | | | $H_4P_2O_7$ (pryophosphoric acid) | |
| | | | | $H_5P_3O_{10}$ (triphosphoric acid) | |
| | | | | $H_6P_4O_{13}$ (tetraphosphoric acid) | |
| V | A | Phosphorus (P) | +6 | $H_4P_2O_8$ (perphosphoric acid) | +5 Species/ +6, +7 Species |
| | | | +7 | $H_3PO_5$ (monoperphosphoric acid) | |
| V | A | Arsenic (As) | +5 | $H_3AsO_4$ (ortho-arsenic acid) | +5 Species/ +7 species |
| | | | | $H_2AsO_4^-$ (mono ortho-arsenate) | |
| | | | | $HAsO_4^{-2}$ (di-ortho-arsenate) | |
| | | | | $AsO_4^{-3}$ (tri-ortho-arsenate) | |
| | | | | $AsO_2^+$ (arsenyl) | |
| | | | +7 | $AsO_3^+$ (perarsenyl) | |
| | | Bismuth (Bi) | +3 | $Bi^{+3}$ (bismuthous) | +3 Species/ +3.5, +4, +5 Species |
| | | | | $BiOH^{+2}$ (hydroxybismuthous) | |
| | | | | $BiO^+$ (bismuthyl) | |
| | | | | $BiO_2^-$ (metabismuthite) | |
| | | | +3.5 | $Bi_4O_7$ (oxide) | |
| | | | +4 | $Bi_2O_4$ (tetroxide) | |
| | | | +5 | $BiO_3^-$ (metabismuthite) | |
| | | | | $Bi_2O_5$ (pentoxide) | |
| | B | Vanadium (V) | +5 | $VO_2^+$ (vanadic) | +5 Species/ +7, +9 Species |
| | | | | $H_3V_2O_7^-$ (pyrovanadate) | |
| | | | | $H_2VO_4^-$ (orthovanadate) | |
| | | | | $VO_3^-$ (metavanadate) | |
| | | | | $HVO_4^{-2}$ (orthovanadate) | |
| | | | | $VO_4^{-3}$ (orthovanadate) | |
| | | | | $V_2O_5$ (pentoxide) | |
| | | | | $H_4V_2O_7$ (pyrovanadic acid) | |
| | | | | $HVO_3$ (metavanadic acid) | |
| | | | | $H_4V_6O_{17}$ (hexavanadic acid) | |
| | | | +7 | $VO_4^-$ (pervanadate) | |
| | | | +9 | $VO_5^-$ (hypervanadate) | |
| V | B | Niobium (Nb) | +5 | $NbO_3^-$ (metaniobate) | +5 Species/+7 species |
| | | | | $NbO_4^{-3}$ (orthoniobate) | |
| | | | | $Nb_2O_5$ (pentoxide) | |
| | | | | $HNbO_3$ (niobid acid) | |
| | | | +7 | $NbO_4^-$ (perniobate) | |
| | | | | $Nb_2O_7$ perniobic oxide | |
| | | | | $HNbO_4$ (perniobic acid) | |
| | | Tantalum (Ta) | +5 | $TaO_3^-$ (metatantalate) | +5 species/+7 species |
| | | | | $TaO_4^{-3}$ (orthotanatalate) | |
| | | | | $Ta_2O_5$ (pentoxide) | |
| | | | | $HTaO_3$ (tantalic acid) | |
| | | | +7 | $TaO_4^-$ (pentantalate) | |
| | | | | $Ta_2O_7$ (pertantalate) | |
| | | | | $HTaO_4 \cdot H_2O$ (pertantalic acid) | |
| VI | A | Sulfur (S) | +6 | $H_2SO_4$ (sulfuric acid) | +6 Species/+7, +8 Species |
| | | | | $HSO_4^-$ (bisulfate) | |
| | | | | $SO_4^{-2}$ (sulfate) | |
| | | | +7 | $S_2O_8^{-2}$ (dipersulfate) | |
| | | | +8 | $H_2SO_5$ (monopersulfuric acid) | |
| | | Selenium (Se) | +6 | $H_2Se_2O_4$ (selenic acid) | +6 species/+7 Species |
| | | | | $HSeO_4^-$ (biselenate) | |
| | | | | $SeO_4^{-2}$ (selenate) | |
| | | | +7 | $H_2Se_2O_8$ (perdiselenic acid) | |
| | | Tellurium (Te) | +6 | $H_2TeO_4$ (telluric acid) | +6 species/+7 species |
| | | | | $HTeOp_4^-$ (bitellurate) | |
| | | | | $TeO_4{-2}$ (tellurate) | |
| | | | +7 | $H_2Te_2O_8$ (perditellenic acid) | |
| | | Polonium (Po) | +2 | $Po^{+2}$ (polonous) | +2, +4 species/ +6 Species |
| | | | +4 | $PoO_3^{-2}$ (polonate) | |
| | | | +6 | $PoO_3$ (peroxide) | |

TABLE I-continued

Simple Anion Redox Couples

| GROUP | SUB GROUP | ELEMENT | VALENCE | SPECIES | SPECIFIC REDOX COUPLES |
|---|---|---|---|---|---|
| VI | B | Chromium | +3 | $Cr^{+3}$ (chromic) | +3 Species/ +4, +6 Species; |
| | | | | $CrOH^{+2}$, $Cr(OH)_2^+$ (chromyls) | +4 Species/ +6 Species |
| | | | | $CrO_2^-$, $CrO_3^{-3}$ (chromites) $Cr_2O_3$ (chromic oxide) $Cr(OH)_3$ (chromic hydroxide) | |
| | | | +4 | $CrO_2$ (dioxide) $Cr(OH)_4$ (hydroxide) | |
| | | | +6 | $H_2CrO_4$ (chromic acid) $HCrO_4^-$ (acid chromate) $CrO_4^{-2}$ (chromate) $Cr_2O_7^{-2}$ (dichromate) | |
| | | Molybdenum (Mo) | +6 | $HMoO_4^-$ (bimolybhate) | +6 Species/ +7 Species |
| | | | | $MoO_4^{-2}$ (molydbate) $MoO_3$ (molybdic trioxide) $H_2MoO_4$ (molybolic acid) | |
| | | | +7 | $MoO_4^-$ (permolybdate) | |
| | | Tungsten (W) | +6 | $WO_4^{-2}$ tungstic) | +6 Species/ +8 Species/ |
| | | | | $WO_3$ (trioxide) $H_2WO_4$ (tungstic acid) | |
| | | | +8 | $WO_5^{-2}$ (pertungstic) $H_2WO_5$ (pertungstic acid) | |
| VII | A | Chlorine (Cl) | +1 | HClO (hypochlorous acid) | +1 Species/+3, +5, +7 Species; |
| | | | | $ClO^-$ (hypochlorite) | +3 Species/ +5, +7 Species; |
| | | | +3 | $HClO_2$ (chlorous acid) | +5 Species/ +7 Species |
| | | | | $ClO_2^-$ (chlorite) | |
| | | | +5 | $HClO_3$ (chloric acid) $ClO_3^-$ (chlorate) | |
| | | | +7 | $HClO_4$ (perchloric acid) $ClO_4^-$, $HClO_5^{-2}$, $ClO_5^{-3}$, $Cl_2O_9^{-4}$ (perchlorates) | |
| VII | A | Bromine (Br) | +1 | HBrO (hypobromous acid) | +1 Species/+3, +5, +7 Species; |
| | | | | $BrO^-$ (hypobromitee) | +3 Species/+5, +7 Species; |
| | | | +3 | $HBrO_2$ (bromous acid) | +5 Species/+7 Species |
| | | | | $BrO2^-$ (bromite) | |
| | | | +5 | $HBrO_3$ (bromic acid) $BrO_3^-$ (bromate) | |
| | | | +7 | $HBrO_4$ (perbromic acid) $BrO_4^-$, $HBrO_5^{-2}$, $BrO_5^{-3}$, $Br_2O_9^{-4}$ (prebromates) | |
| | | Iodine | +1 | HIO (hypoiodus acid) | +1 Species/+3, +5, +7 Species; |
| | | | | $IO^-$ (hypoiodite) | +3 Species/+5, +7 Species; |
| | | | +3 | $HIO_2$ (iodous acid) | +5 Species/+7 Species |
| | | | | $IO_2^-$ (iodite) | |
| | | | +5 | $HIO_3$ (iodic acid) $IO_3^-$ (iodate) | |
| | | | +7 | $HIO_4$ (periodic acid) $IO_4^-$, $HIO_5^{-2}$, $IO_5^{-3}$, $I_2O_9^{-4}$ (periodates) | |
| | B | Manganese (Mn) | +2 | $Mn^{+2}$ (manganeous) | +2 Species/+3, +4, +6, +7 Species; |
| | | | | $HMnO_2^-$ (dimanganite) | +3 Species/+4, +6, +7 Species; |
| | | | +3 | $Mn^{+3}$ (manganic) | +4 Species/+6, +7 Species; |
| | | | +4 | $MnO_2$ (dioxide) | +6 Species/+7 Species |
| | | | +6 | $MnO_4^{-2}$ (manganate) | |
| | | | +7 | $MnO_4^-$ (permanganate) | |
| VIII | Period 4 | Iron (Fe) | +3 | $Fe^{+3}$ (ferric) $Fe(OH)^{+2}$ | +3 Species/+4, +5, +6 Species; |

TABLE I-continued

Simple Anion Redox Couples

| GROUP | SUB GROUP | ELEMENT | VALENCE | SPECIES | SPECIFIC REDOX COUPLES |
|---|---|---|---|---|---|
| VIII | Period 4 | Iron (Fe) | +4 | $Fe(OH)_2^+$ $FeO_2^{-2}$ (ferrite) $FeO^{+2}$ (ferryl) $FeO_2^{-2}$ (perferrite) | +4 Species/ +5, +6 Species; +5 Species/ +6 Species |
| | | | +5 | $FeO_2^+$ (perferryl) | |
| | | | +6 | $FeO_4^{-2}$ (ferrate) | |
| | | Cobalt (Co) | +2 | $Co^{+2}$ (cobalous) | +2 Species/ +3, +4 Species; +3 Species/ +4 Species |
| | | | | $HCoO_2^-$ (dicobaltite) | |
| | | | +3 | $Co^{+3}$ (cobaltic) $Co_2O_3$ (cobaltic oxide) | |
| | | | +4 | $CoO_2$ (peroxide) $H_2CoO_3$ (cobaltic acid) | |
| | | Nickel (Ni) | +2 | $Ni^{+2}$ (nickelous) | +2 Species/+3, +4, +6 Species; +3 Species/ +4, +6 Species; +4 Species/ +6 Species |
| | | | | $NiOH^+$ | |
| | | | | $HNiO_2^-$ (dinickelite) | |
| | | | | $NiO_2^{-2}$ (nickelite) | |
| | | | +3 | $Ni^{+3}$ (nickelic) $Ni_2O_3$ (nickelic oxide) | |
| | | | +4 | $NiO_2$ (peroxide) | |
| | | | +6 | $NiO_4^{-2}$ (nickelate) | |
| VIII | Period 5 | Ruthenium (Ru) | +2 | $Ru^{+2}$ | +2 Species/+3, +4, +5, +6, +7, +8 Species; |
| | | | +3 | $Ru^{+3}$ | +3 Species/+4, +5, +6, +7, +8 Species; |
| | | | | $Ru_2O_3$ (sesquioxide) | +4 Species/ +5, +6, +7, +8 Species; |
| | | | | $Ru(OH)_3$ (hydroxide) | +5 Species/+6, +7, +8 Species; |
| | | | +4 | $Ru^{+4}$ (ruthenic) | +6 Species/ +7, +8 Species; |
| | | | | $RuO_2$ (ruthenic dioxide) | +7 Species/ +8 Species |
| | | | | $Ru(OH)_4$ (ruthenic hydroxide) | |
| | | | +5 | $Ru_2O_5$ (pentoxide) | |
| | | | +6 | $RuO_4^{-2}$ (ruthenate) $RuO_2^{+2}$ (ruthenyl) $RuO_3$ (trioxide) | |
| | | | +7 | $RuO_4^-$ (perruthenate) | |
| | | | +8 | $H_2RuO_4$ (hyperuthenic acid) $HRuO_5^-$ (diperruthenate) $RuO_4$ (ruthenium tetroxide) | |
| | | Rhodium (Rh) | +1 | $Rh^+$ (hyporhodous) | +1 Species/+2, +3, +4, +6 Species; |
| | | | +2 | $Rh^{+2}$ (rhodous) | +2 Species/+3, +4, +6 Species; |
| | | | +3 | $Rh^{+3}$ (rhodic) | +3 Species/+4, +6 Species; |
| | | | | $Rh_2O_3$ (sesquioxide) | +4 Species/+6 Species |
| | | | +4 | $RhO_2$ (rhodic oxide) $Rh(OH)_4$ (hydroxide) | |
| | | | +6 | $RhO_4^{-2}$ (rhodate) $RhO_3$ (trioxide) | |
| | | Palladium | +2 | $Pd^{+2}$ (palladous) | +2 Species/+3, +4, +6 Species; |
| | | | | $PdO_2^{-2}$ (palladite) | +3 Species/ +4, +6 Species; |
| | | | +3 | $Pd_2O_3$ (sesquioxide) | +4 Species/ +6 Species |
| | | | +4 | $PdO_3^{-2}$ (palladate) $PdO_2$ (dioxide) $Pd(OH)_4$ (hydroxide) | |
| | | | +6 | $PdO_3$ (peroxide) | |

TABLE I-continued

Simple Anion Redox Couples

| GROUP | SUB GROUP | ELEMENT | VALENCE | SPECIES | SPECIFIC REDOX COUPLES |
|---|---|---|---|---|---|
| VIII | Period 6 | Iridium (Ir) | +3 | $Ir^{+3}$ (iridic) | +3 Species/ +4, +6 Species; |
| | | | | $Ir_2O_3$ (iridium sesquioxide) | +4 Species/ +6 Species |
| | | | | $Ir(OH)_3$ (iridium hydroxide) | |
| | | | +4 | $IrO_2$ (iridic oxide) | |
| | | | | $Ir(OH)_4$ (iridic hydroxide) | |
| | | | +6 | $IrO_4^{-2}$ (iridate) | |
| | | | | $IrO_3$ (iridium peroxide) | |
| | | Platinum (Pt) | +2 | $Pt^{+2}$ (platinous) | +2, +3 Species/ +4, +6 Species; |
| | | | +3 | $Pt_2O_3$ (sesquioxide) | +4 Species/ +6 Species |
| | | | +4 | $PtO_3^{-2}$ (palatinate) | |
| | | | | $PtO^{+2}$ (platinyl) | |
| | | | | $Pt(OH)^{+3}$ | |
| | | | | $PtO_2$ (platonic oxide) | |
| | | | +6 | $PtO_4^{-2}$ (Perplatinate) | |
| | | | | $PtO_3$ (perplatinic oxide) | |
| IIIB | Rare earths | Cerium (Ce) | +3 | $Ce^{+3}$ (cerous) | +3 Species/ +4, +6 Species; |
| | | | | $Ce_2O_3$ (cerous oxide) | +4 Species/ +6 Species |
| | | | | $Ce(OH)_3$ (cerous hydroxide) | |
| | | | +4 | $Ce^{+4}$, $Ce(OH)^{+3}$, $Ce(OH)_2^{+2}$, $Ce(OH)_3^+$ (ceric) | |
| | | | | $CeO_2$ (ceric oxide) | |
| | | | +6 | $CeO_3$ (peroxide) | |
| | | Praseodymium (Pr) | +3 | $Pr^{+3}$ (praseodymous) | +3 species/+4 species |
| | | | | $Pr_2O_3$ (sesquioxide) | |
| | | | | $Pr(OH)_3$ (hydroxide) | |
| | | | +4 | $Pr^{+4}$ (praseodymic) | |
| | | | | $PrO_2$ (dioxide) | |
| | | Neodymium | +3 | $Nd^{+3}$ | +3 Species/+4 Species |
| | | | | $Nd_2O_3$ (sesquioxide) | |
| | | | +4 | $NdO_2$ (peroxide) | |
| | | Terbium (Tb) | +3 | $Tb^{+3}$ | +3 Species/+4 Species |
| | | | | $Tb_2O_3$ (sesquioxide) | |
| | | | +4 | $TbO_2$ (peroxide) | |
| | Actinides | Thorium (Th) | +4 | $Th^{+4}$ (thoric) | +4 Species/+6 Species |
| | | | | $ThO^{+2}$ (thoryl) | |
| | | | | $HThO_3^-$ (thorate) | |
| | | | +6 | $ThO_3$ (acid peroxide) | |
| | | Uranium (U) | +6 | $UO_2^{+2}$ (uranyl) | +6 Species/+8 Species |
| | | | | $UO_3$ (uranic oxide) | |
| | | | +8 | $HUO_5^-$, $UO_5^{-2}$ (peruranates) | |
| | | | | $UO_4$ (peroxide) | |
| | | Neptunium (Np) | +5 | $NpO_2^+$ (hyponeptunyl) | +5 Species/+6, +8 Species; |
| | | | | $Np_2O_5$ (pentoxide) | +6 Species/+8 Species |
| | | | +6 | $NpO_2^{+2}$ (neptunyl) | |
| | | | | $NpO_3$ (trioxide) | |
| | | | +8 | $NpO_4$ (peroxide) | |
| | | Plutonium (Pu) | +3 | $Pu^{+3}$ (hypoplutonous) | +3 Species/+4, +5, +6 Species; |
| | | | +4 | $Pu^{+4}$ (plutonous) | +4 Species/+5, +6 Species; |
| | | | | $PuO_2$ (dioxide) | +5 Species/+6 Species |
| | | | +5 | $PuO_2^+$ (hypoplutonyl) | |
| | | | | $Pu_2O_5$ (pentoxide) | |
| | | | +6 | $PuO_2^{+2}$ (plutonyl) | |
| | | | | $PuO_3$ (peroxide) | |
| | | Americium (Am) | +3 | $Am^{+3}$ (hypoamericious) | +3 Species/+4, +5, +6 Species; |
| | | | +4 | $Am^{+4}$ (americous) | +4 Species/+5, +6 Species; |

TABLE I-continued

Simple Anion Redox Couples

| GROUP | SUB GROUP | ELEMENT | VALENCE | SPECIES | SPECIFIC REDOX COUPLES |
|---|---|---|---|---|---|
| | | | | $AmO_2$ (dioxide) | +5 Species/+6 Species |
| | | | +5 | $Am(OH)_4$ (hydroxide) $AmO_2^+$ (hypoamericyl) $Am_2O_5$ (pentoxide) | |
| | | | +6 | $AmO_2^{+2}$ (americyl) $AmO_3$ (peroxide) | |

TABLE II

Elements Participating as Heteroatoms in Heteropolyanion Complex Anion Redox Couple Mediators

| GROUP | SUB GROUP | ELEMENT |
|---|---|---|
| I | A | Lithium (Li), Sodium (Na), Potassium (K), and Cesium (Cs) |
| | B | Copper (Cu), Silver (Ag), and Gold (Au) |
| II | A | Beryllium (Be), Magnesium (Mg), Calcium (Ca), Strontium (Sr), and B |
| | B | Zinc (Zn), Cadmium (Cd), and Mercury (Hg) |
| III | A | Boron (B), and Aluminum (Al) |
| | B | Scandium (Sc), and Yttrium (Y) - (See Rare Earths) |
| IV | A | Carbon (C), Silicon (Si), Germanium (Ge), Tin (Sn) and Lead (Pb) |
| | B | Titanium (Ti), Zirconium (Zr), and Hafnium (Hf) |
| V | A | Nitrogen (N), Phosphorous (P), Arsenic (As), Antimony (Sb), and Bism |
| | B | Vanadium (V), Niobium (Nb), and Tantalum (Ta) |
| VI | A | Sulfur (S), Selenium (Se), and Tellurium (Te) |
| | B | Chromium (Cr), Molybdenum (Mo), and Tungsten (W) |
| VII | A | Fluorine (F), Chlorine (Cl), Bromine (Br), and Iodine (I) |
| | B | Manganese (Mn), Technetium (Tc), and Rhenium (Re) |
| VIII | Period 4 | Iron (Fe), Cobalt (Co), and Nickel (Ni) |
| | Period 5 | Ruthenium (Ru), Rhodium (Rh), and Palladium (Pd) |
| | Period 6 | Osmium (Os), Iridium (Ir), and Platinum (Pt) |
| IIIB | Rare Earths | All. |

16. The process of claim 15, wherein the adding energy comprises introducing an ultrasonic energy source and/or an ultraviolet energy source into the anolyte portion, promoting the formation of the hydroxyl free radicals, wherein the added energy comprises using ultrasonic energy and inducing microscopic bubble expansion and implosion for reducing in size individual second phase waste and/or inorganic materials volumes dispersed in the anolyte.

17. The process of claim 1, further comprising using the mediator oxidizing species that are found in situ in the waste and/or inorganic materials to be decomposed, by circulating the waste and/or inorganic materials-anolyte mixture through the electrochemical cell where in an oxidized form of an in situ reversible redox couple is formed by anodic oxidizing or reacting with an oxidized form of a more powerful redox couple added to or already present in the anolyte portion and anodically oxidized in the electrochemical cell, thereby destroying the biological and organic materials in the waste and/or inorganic materials.

18. The process of claim 15, further comprising using an alkaline electrolyte selected from a group consisting of NaOH or KOH and combinations thereof, with the mediator oxidizing species, wherein a reduced form of a mediator redox couple has sufficient solubility in said electrolyte for allowing desired oxidation of the biological and organic materials in the waste and/or inorganic materials.

19. The process of claim 1, wherein the oxidation potential of redox reactions of the mediator oxidizing species and the biological and organic molecules in the waste and/or inorganic materials producing hydrogen ions are inversely proportional to electrolyte pH, and thus with a selection of a mediator redox couple increasing the electrolyte pH reduces the electric potential required, thereby reducing electric power consumed per unit mass of the waste and/or inorganic materials destroyed.

20. The process of claim 15, wherein the electrolyte is an aqueous solution chosen from the group consisting of acids, alkalines and salt electrolytes and mixtures of salt and either acids or alkalines and combinations thereof.

21. The process of claim 15, further comprising interchanging the mediator oxidizing species without changing equipment, and wherein the anolyte and catholyte portions of electrolyte are independent of one another and comprise aqueous solutions selected from the group consisting of acids, alkali or salts or mixtures of salt and either acids or alkalines and combinations thereof.

22. The process of claim 15, wherein the oxidizing and destroying waste and/or inorganic materials comprises destroying and oxidizing solid waste and/or inorganic materials, comprises oxidizing and destroying liquid waste and/or inorganic materials, comprises treating and oxidizing gas waste and/or inorganic materials, comprises oxidizing and destroying a combination of liquids, solids, and gases in waste and/or inorganic materials.

23. The process of claim 15, further comprising requiring removing and treating precipitates resulting from combinations of the oxidizing species and other species released from the waste and/or inorganic materials during destruction and sterilization.

24. The process of claim 15, further comprising a catholyte portion of the electrolyte, and wherein the anolyte and catholyte portions of electrolyte are independent of one another, and comprise aqueous solutions selected from a group consisting of acids, alkali or salt or a mixture of salt and either acids or alkali and combinations thereof.

25. The process of claim 15, further comprising separating a catholyte portion of the electrolyte from the anolyte portion with a membrane, operating the electrochemical cell at a current density such that there is the possibility that metallic anions may leak through the membrane in small quantities, typically 0.5 amps per square centimeter of membrane or less, and recovering the metallic anions from the catholyte through a device such as a resin column, thus allowing a greater rate of destruction of waste and/or inorganic materials in the anolyte portion.

26. The process of claim 15, wherein the catholyte solution portion further comprises an aqueous solution and the electrolyte in the solution is composed of acids, alkali or salts, and further comprising adding oxygen to this the solution when $HNO_3$ or $NO_3$ can occur in the catholyte portion, controlling concentration of electrolyte in the catholyte to maintain conductivity of the catholyte portion desired in the electrochemical cell, providing mechanical mixing and/or ultrasonic energy induced microscopic bubble formation, and implosion for vigorous mixing in the catholyte solution for oxidizing the nitrous acid and small amounts of nitrogen oxides $NO_X$, introducing air into the catholyte portion for promoting the oxidizing of the nitrous acid and the small amounts of NOR, and diluting any hydrogen produced in the catholyte portion before releasing the air and hydrogen.

* * * * *